(12) United States Patent
Sam et al.

(10) Patent No.: US 11,938,081 B2
(45) Date of Patent: Mar. 26, 2024

(54) NEUROMUSCULAR ENHANCEMENT SYSTEM

(71) Applicants: Safavi-Abbasi Sam, Scottsdale, AZ (US); Brent Hartman, Scottsdale, AZ (US); Phillip Reyes, Tempe, AZ (US)

(72) Inventors: Safavi-Abbasi Sam, Scottsdale, AZ (US); Brent Hartman, Scottsdale, AZ (US); Phillip Reyes, Tempe, AZ (US)

( * ) Notice: Subject to any disclaimer, the term of this patent is extended or adjusted under 35 U.S.C. 154(b) by 337 days.

(21) Appl. No.: 17/178,060

(22) Filed: Feb. 17, 2021

(65) Prior Publication Data

US 2021/0259913 A1     Aug. 26, 2021

Related U.S. Application Data

(63) Continuation-in-part of application No. PCT/US2019/047134, filed on Aug. 20, 2019.
(Continued)

(51) Int. Cl.
*A61H 23/00*     (2006.01)
*A41D 13/12*     (2006.01)
(Continued)

(52) U.S. Cl.
CPC ......... *A61H 23/02* (2013.01); *A41D 13/1209* (2013.01); *A61B 90/36* (2016.02);
(Continued)

(58) Field of Classification Search
CPC ........ B25J 9/0006; A61B 90/60; A61B 90/36; A61B 2090/365; A61B 2090/36;
(Continued)

(56) References Cited

U.S. PATENT DOCUMENTS 7,918,808 B2 *   4/2011   Simmons .............. B25J 9/0006
                                                           600/590
8,734,369 B2 *   5/2014   Perry .................. A61H 9/0078
                                                           601/151
(Continued)

FOREIGN PATENT DOCUMENTS

WO     WO-2013033669 A2 *   3/2013   .............. A61F 2/50

OTHER PUBLICATIONS

Haines et al., New Twist on Artificial Muscles, Mar. 2018, www.pnas.org/cgi/doi/10.1073/pnas.1605273113; PNAS Mar. 13, 2018; vol. 115, No. 11.
(Continued)

*Primary Examiner* — Margaret M Luarca
*Assistant Examiner* — Tyler A Raubenstraw
(74) *Attorney, Agent, or Firm* — V Gerald Grafe

(57) ABSTRACT

A neuromuscular enhancement system comprising engineered textile structures is worn by a user to increase strength, preserve energy, and increase motion accuracy. The system can be used in surgery and interface with operating room technology, together providing the surgeon with the ability to perform surgery for longer hours and with increased accuracy. The enhancement system is a flexible structure, worn over the user's body, comprising engineered textile materials that apply forces to different areas of the user's body. The engineered materials can be activated in order to apply a force to a particular region of the body to assist in a desired user output. The engineered materials can be embedded with sensors to detect and monitor motion and other physical properties. The engineered materials can also be embedded with a communication system that conveys information between a computer system and the neuromuscular enhancement system and its various sensors and com-
(Continued)

ponents. The enhancement system here can be configured for use in applications other than surgery.

19 Claims, 78 Drawing Sheets

Related U.S. Application Data

(60) Provisional application No. 62/719,761, filed on Aug. 20, 2018.

(51) Int. Cl.
*A61B 90/00* (2016.01)
*A61B 90/60* (2016.01)
*A61H 23/02* (2006.01)
*B25J 9/00* (2006.01)

(52) U.S. Cl.
CPC .............. *A61B 90/60* (2016.02); *B25J 9/0006* (2013.01); *A41D 2400/322* (2013.01); *A41D 2500/00* (2013.01); *A61B 2090/365* (2016.02); *A61H 2201/01* (2013.01); *A61H 2201/1207* (2013.01); *A61H 2201/165* (2013.01); *A61H 2201/50* (2013.01)

(58) Field of Classification Search
CPC .......... A41D 13/1209; A41D 2400/322; A41D 2500/00; A61H 23/02; A61H 1/008; A61H 2201/50; A61H 1/0274; A61H 2201/01; A61H 2201/1207; A61H 2201/165; A61H 23/00; G09B 23/00; G09B 9/00
See application file for complete search history.

(56) References Cited

U.S. PATENT DOCUMENTS

| | | | | |
|---|---|---|---|---|
| 9,503,681 | B1* | 11/2016 | Popescu | G06F 40/169 |
| 9,956,092 | B1* | 5/2018 | Theobald | A61H 9/0078 |
| 10,124,484 | B1* | 11/2018 | Barnes | B25J 9/0006 |
| 10,307,272 | B2* | 6/2019 | Herr | B25J 9/1075 |
| 10,532,000 | B1* | 1/2020 | De Sapio | A63B 24/0062 |
| 2004/0091845 | A1* | 5/2004 | Azerad | G09B 23/283 |
| | | | | 434/263 |
| 2005/0181342 | A1* | 8/2005 | Toly | G09B 23/30 |
| | | | | 434/262 |
| 2005/0249917 | A1 | 11/2005 | Trentacosta | |
| 2008/0177284 | A1* | 7/2008 | Lee | A61B 34/35 |
| | | | | 606/130 |
| 2013/0040783 | A1 | 2/2013 | Duda | |
| 2014/0370475 | A1* | 12/2014 | Bova | G09B 23/285 |
| | | | | 434/267 |
| 2016/0058644 | A1* | 3/2016 | Cheatham, III | A61B 5/4836 |
| | | | | 601/84 |
| 2016/0139666 | A1* | 5/2016 | Rubin | A63F 13/212 |
| | | | | 345/633 |
| 2016/0317383 | A1* | 11/2016 | Stanfield | A61H 23/0236 |
| 2017/0229044 | A1* | 8/2017 | Benson | G09B 23/285 |
| 2018/0012416 | A1* | 1/2018 | Jones | G06F 3/017 |
| 2018/0042810 | A1* | 2/2018 | Nguyen | A61H 23/02 |
| 2018/0056104 | A1* | 3/2018 | Cromie | A61H 3/00 |
| 2018/0078034 | A1* | 3/2018 | Savall | A47B 21/03 |
| 2018/0092791 | A1* | 4/2018 | Alper | A61H 1/008 |
| 2018/0153638 | A1* | 6/2018 | Paixao Correia | A61B 90/60 |
| 2018/0168352 | A1* | 6/2018 | Richardson | A47C 7/00 |
| 2018/0177670 | A1* | 6/2018 | Shim | B25J 9/0006 |
| 2018/0243163 | A1* | 8/2018 | Choudhury | A61H 23/02 |
| 2018/0249151 | A1* | 8/2018 | Freeman | A61B 5/6803 |
| 2018/0303575 | A1* | 10/2018 | Nardo | A61B 90/60 |
| 2018/0338806 | A1* | 11/2018 | Grubbs | A61B 34/30 |
| 2019/0005848 | A1* | 1/2019 | Garcia Kilroy | G09B 23/28 |
| 2019/0015233 | A1* | 1/2019 | Galloway | B25J 15/12 |
| 2019/0015287 | A1* | 1/2019 | Witte | A61H 3/00 |
| 2019/0194843 | A1* | 6/2019 | Alexander | D01F 1/106 |
| 2019/0247650 | A1* | 8/2019 | Tran | A61N 1/3704 |
| 2019/0307419 | A1* | 10/2019 | Durfee | A61B 8/14 |
| 2019/0318640 | A1* | 10/2019 | Goel | A61B 90/36 |
| 2020/0008583 | A1* | 1/2020 | Gunura | A47C 9/10 |
| 2020/0015598 | A1* | 1/2020 | Hondori | B25J 13/02 |
| 2021/0283001 | A1* | 9/2021 | Von Zitzewitz | A61B 5/7282 |

OTHER PUBLICATIONS

Yang et al., Soft Fabric Actuator for Robotic Applications, Oct. 2018, 2018 IEEE/RSJ International Conference on Intelligent Robots and Systems (IROS) Madrid, Spain, Oct. 1-5, 2018.
International Search Report in parent application PCT/US2019/047134, dated Oct. 15, 2019.

* cited by examiner

Magnification

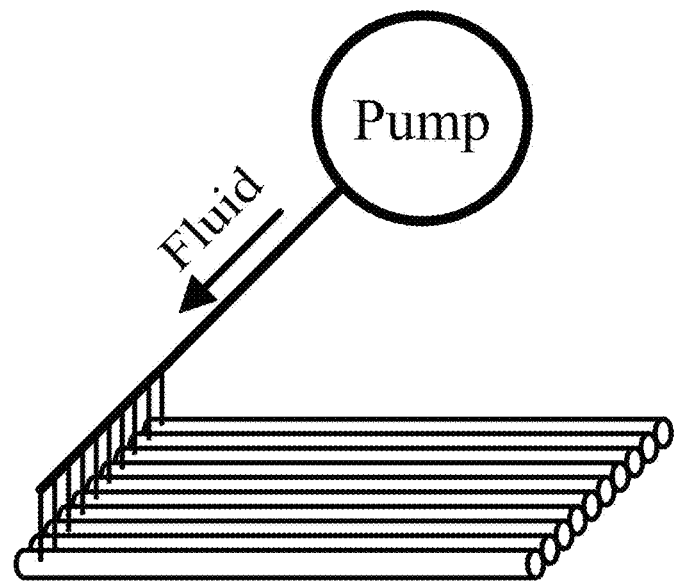
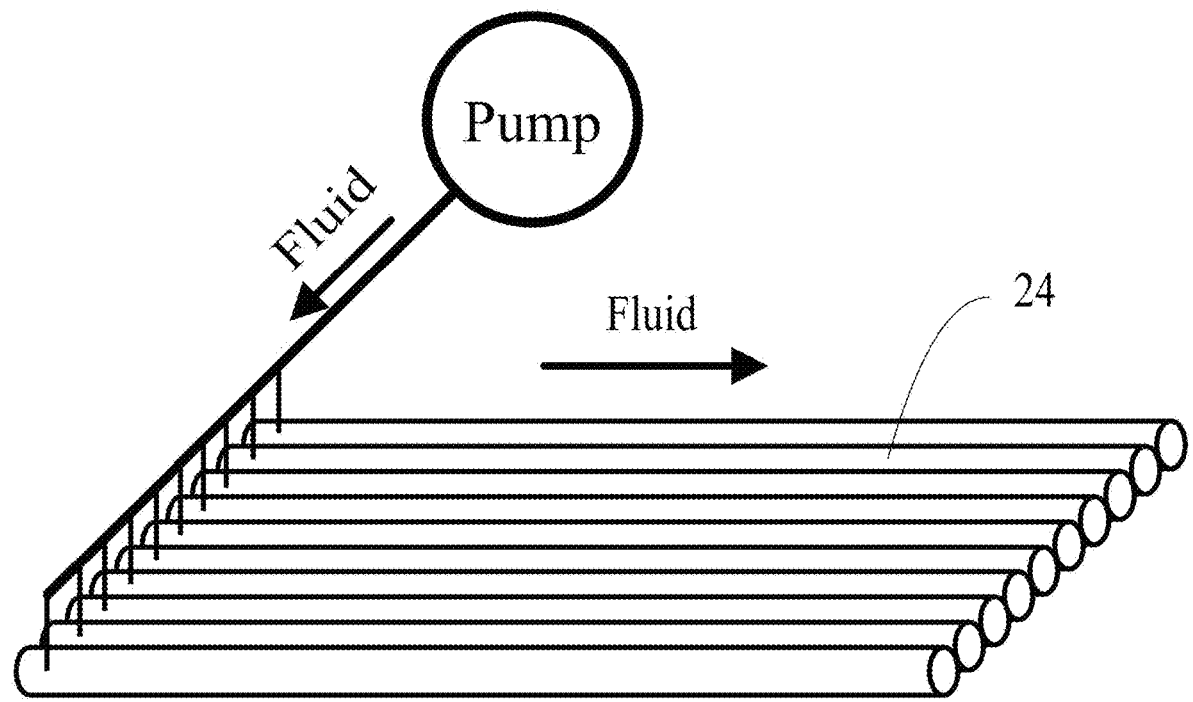
FIG. 14

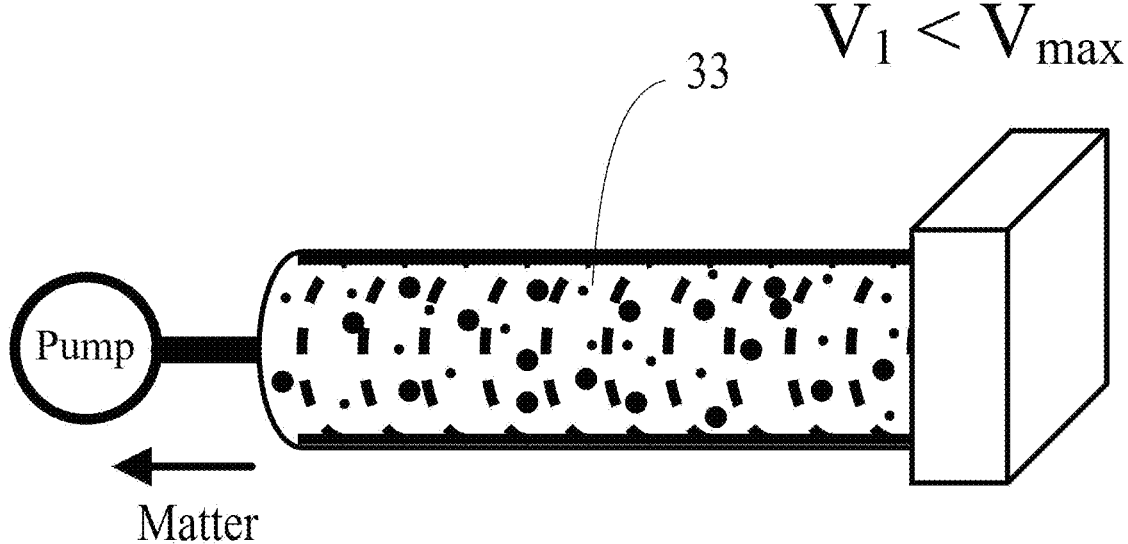
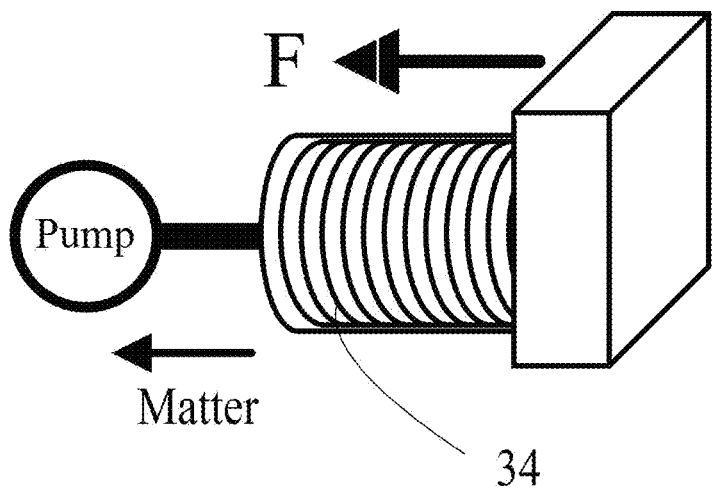
FIG. 19

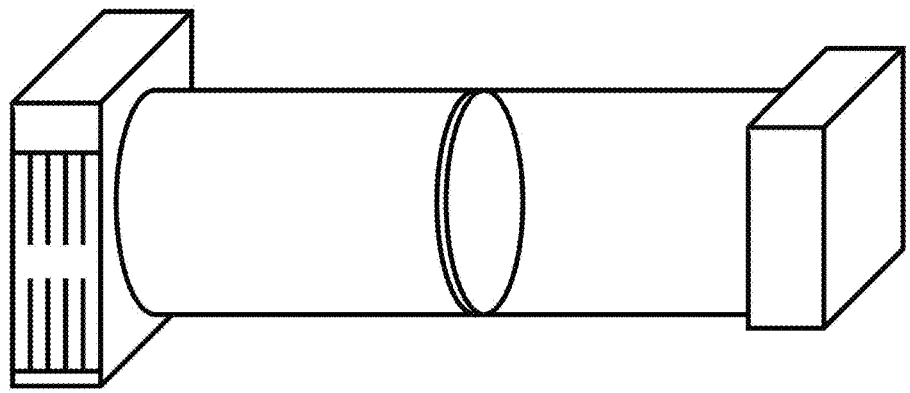
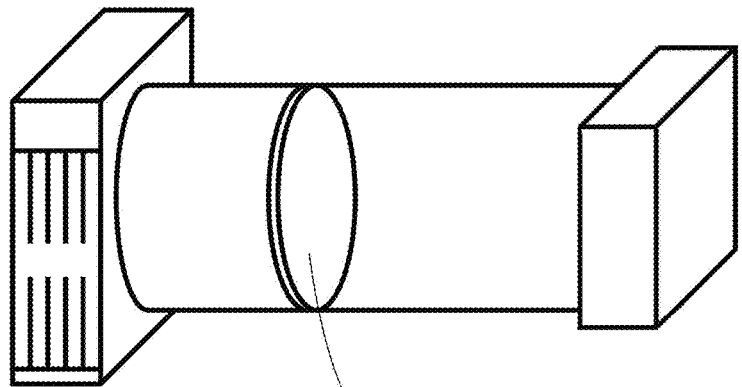
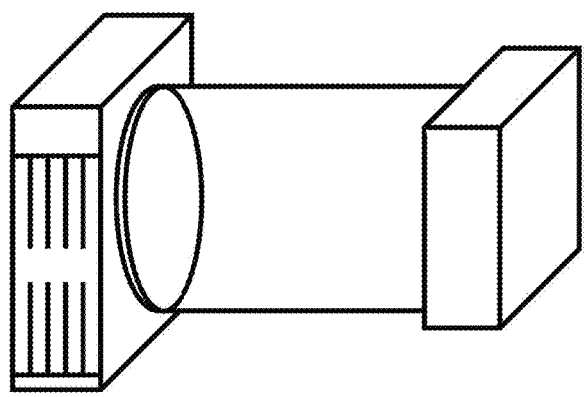
FIG. 22

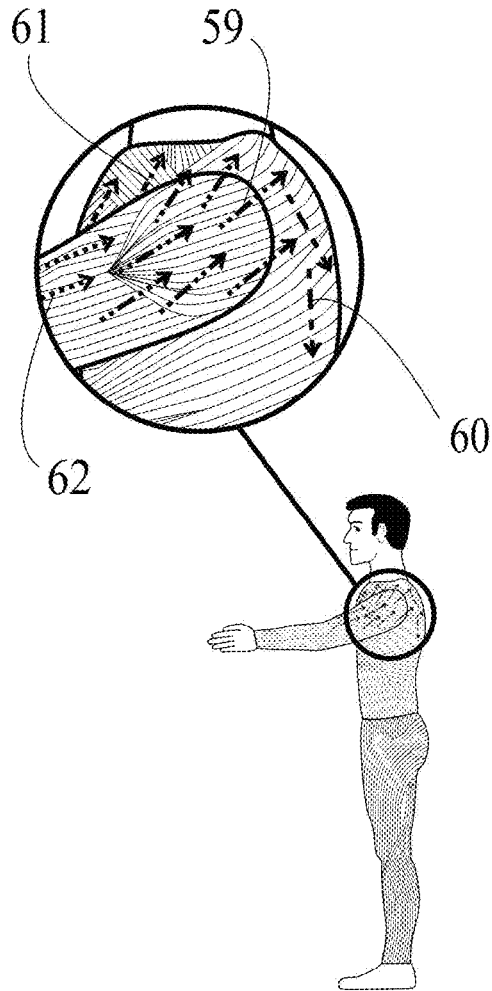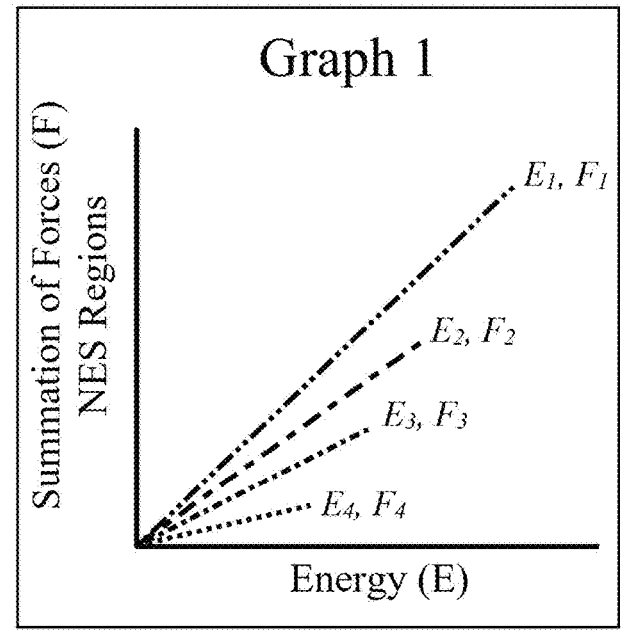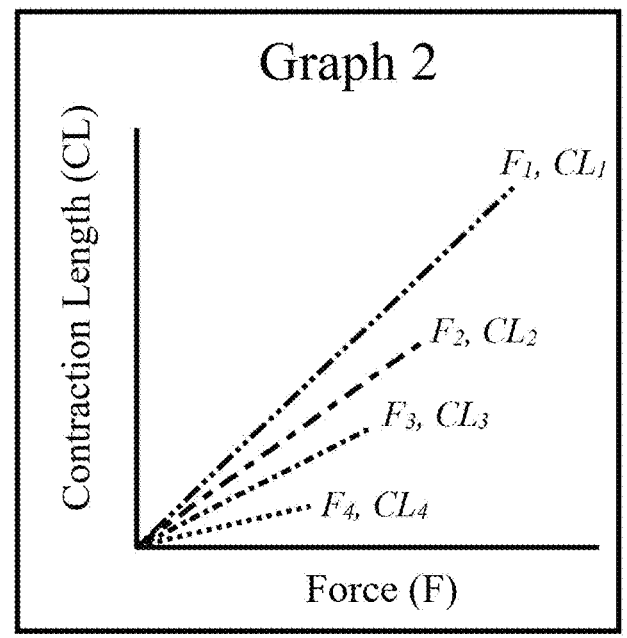
Subscript Key: Major Muscle Groups and their Corresponding NES Regions
1 = Anterior Deltoid
2 = Teres Major / Subscapularis
3 = Pectoralis Major
4 = Biceps
FIG. 29

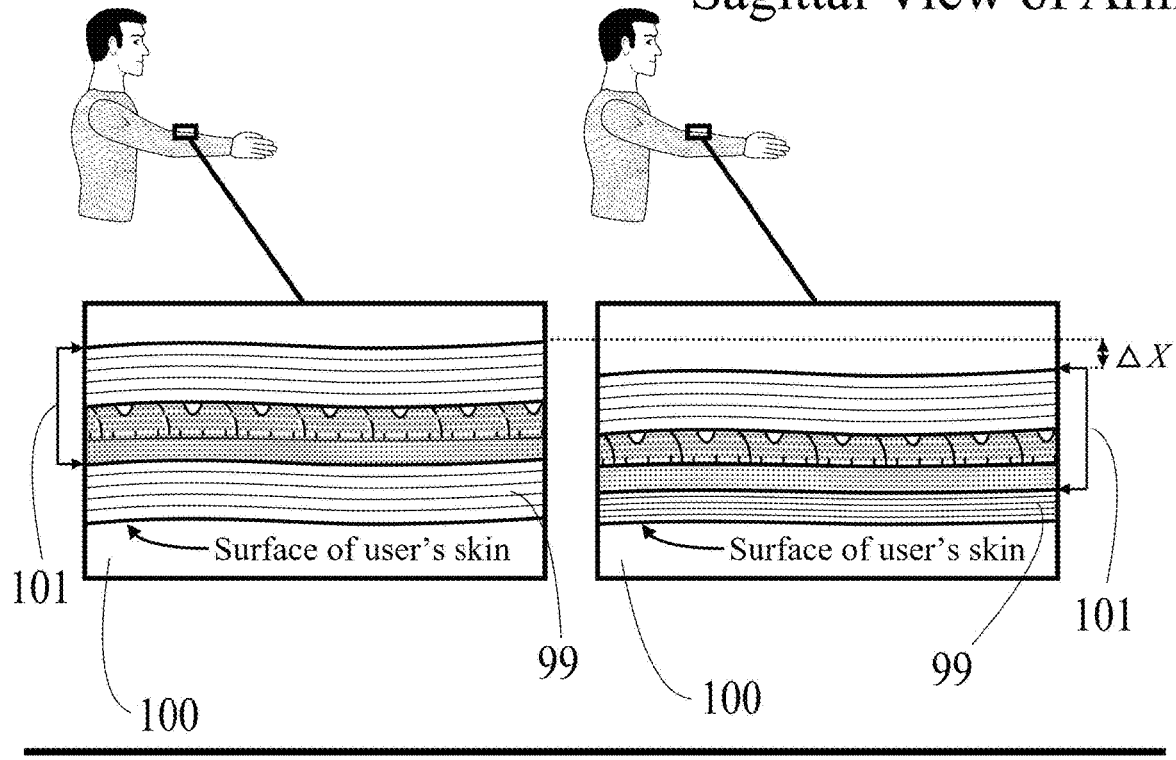
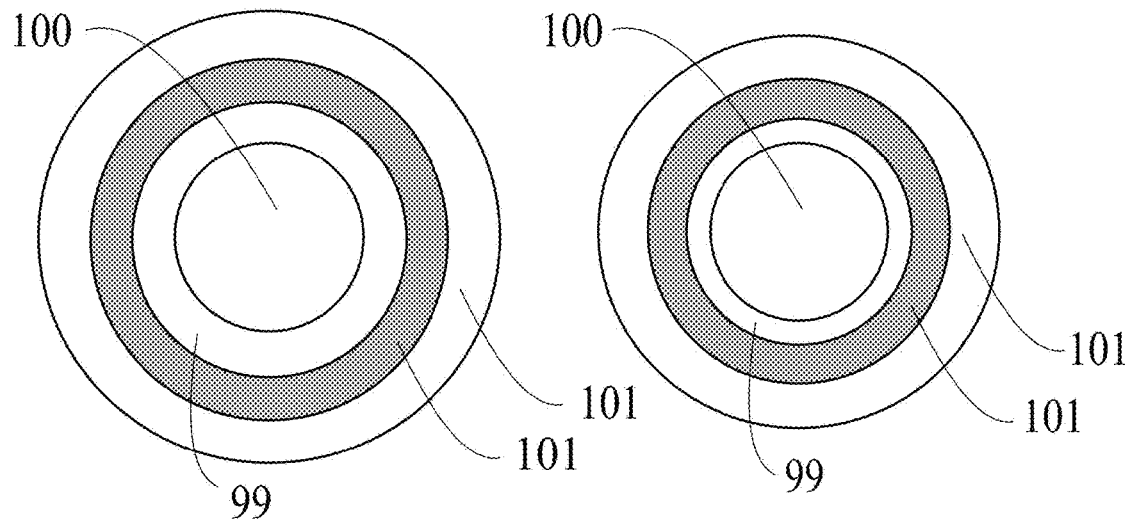
FIG. 38

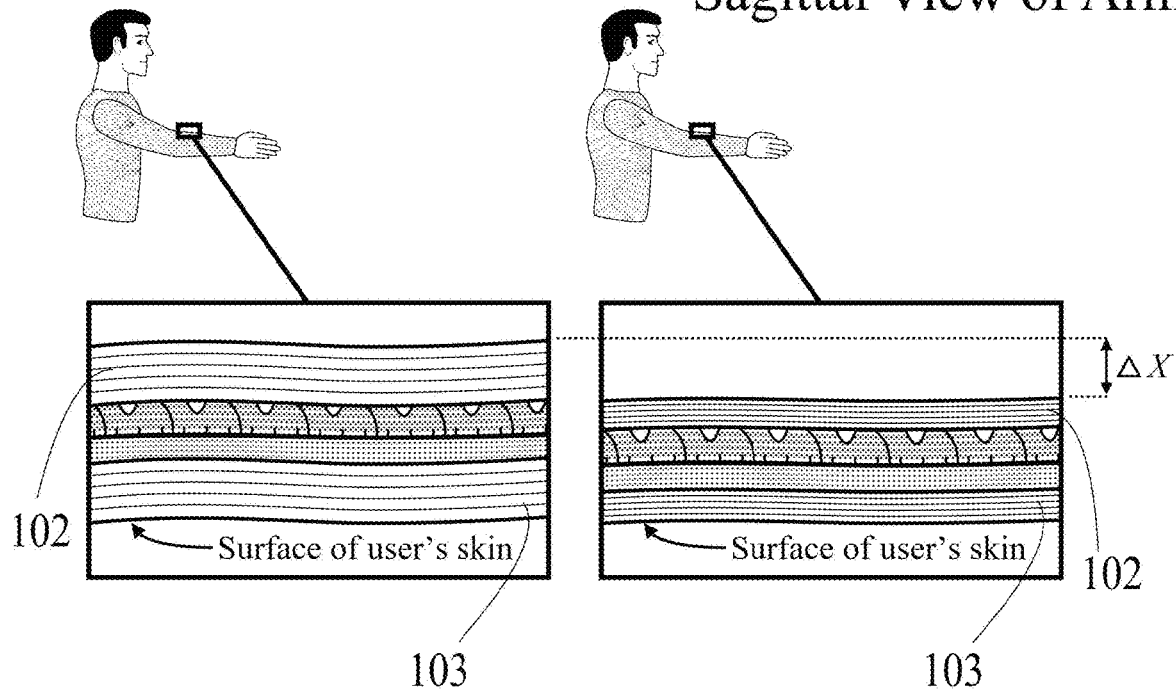
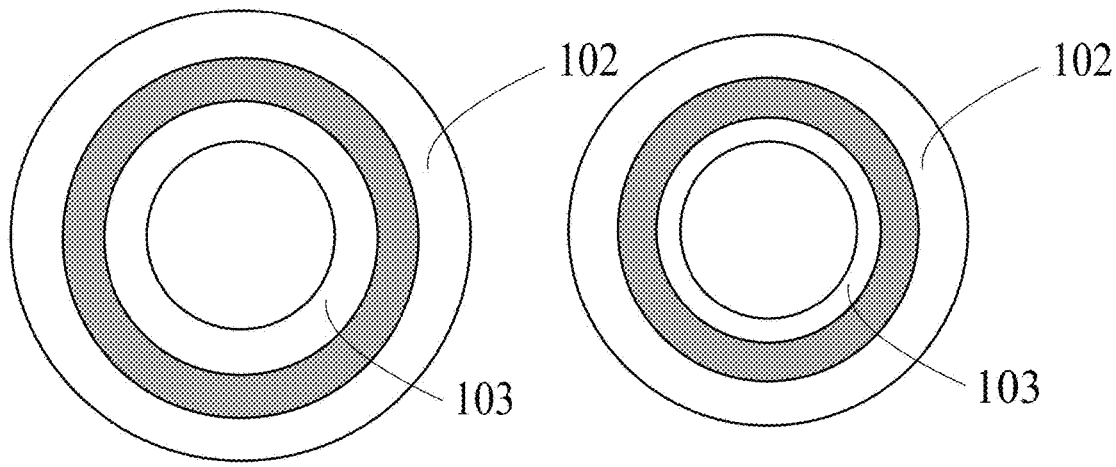
FIG. 39

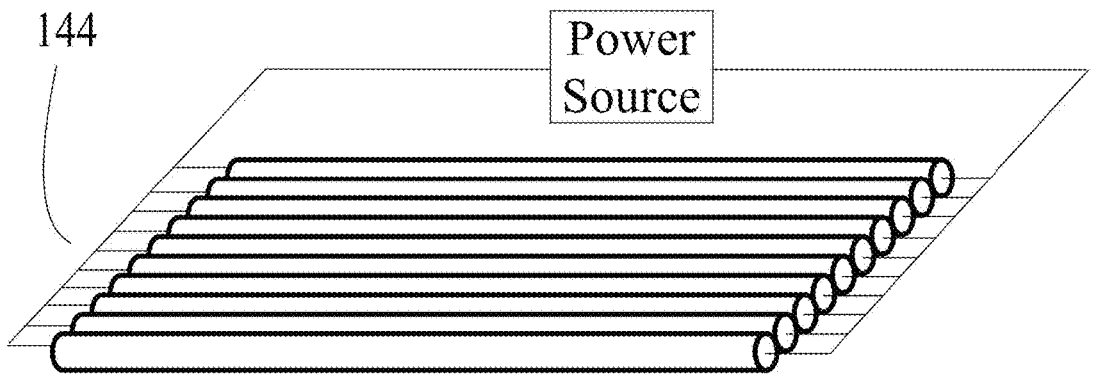
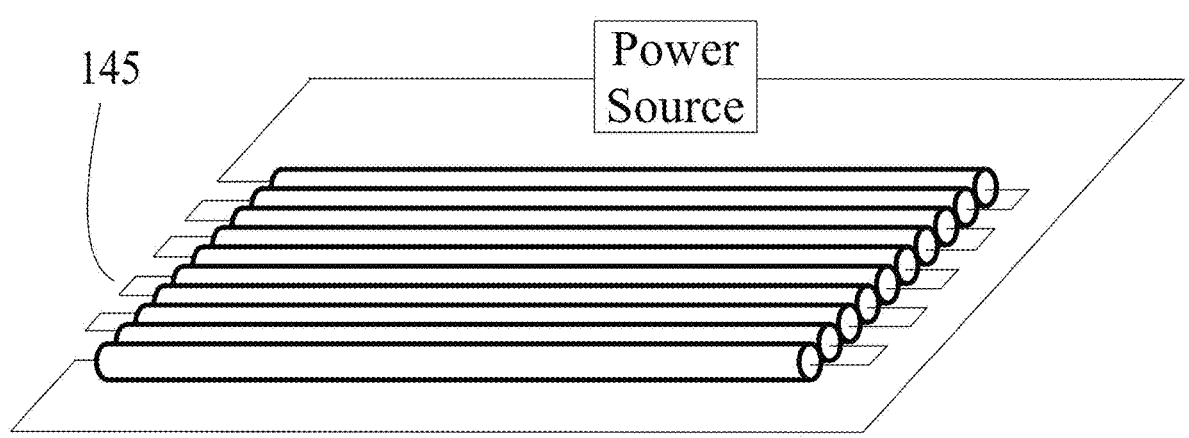
FIG. 56

$P_d$ = Positional Data
$C_c$ = Computer Command $P_d$ = Positional Data
$C_c$ = Computer Command

NEUROMUSCULAR ENHANCEMENT SYSTEM

CROSS REFERENCE TO RELATED APPLICATIONS

This application claims priority as a continuation in part of PCT/US2019/047134, filed 20 Aug. 2019, and thence to U.S. provisional 62/719,761, filed 20 Aug. 2018. Each of the foregoing is incorporated herein by reference.

TECHNICAL FIELD

The subject invention relates to the field of wearable items configured to assist an individual in performing actions such as surgery.

BACKGROUND ART

Extensive physical exertion is used by a surgeon in order to perform surgery. While standing or sitting, the surgeon uses several muscles to perform surgery—neck, back, arm, and leg muscles, to name a few. The long hours of standing or sitting and leaning over an operating table lead to an increase in muscle fatigue as the day progresses. The effect of the surgeon's fatigue on the patient can vary in its level of severity. Due to fatigue, a surgeon might make a mistake that could lead to serious harm to the patient or even death. While fatigue might not always lead to a mistake that is detrimental to the patient, it can be the cause for a reduction in the quality of treatment the surgeon is able to provide or the decisions being made. Fatigue can also result in the surgeon not being able to take on as many cases as he or she would desire, due to the surgeon requiring more time between procedures for physical and mental rest. A reduction in caseload also occurs as the surgeon ages and is less physically capable of spending prolonged hours in the operating room.

Various systems have been developed attempting to advance surgical technology by improving surgical accuracy, patient outcomes, and reduce surgeon burnout. One invention, the surgical procedure chair, is a simple solution to mitigate fatigue during surgery. These chairs allow the surgeon to sit during surgery while offering leg and back support. Depending on the chair model, the chair can also allow the surgeon to rest his or her arms on arm rests while performing surgery. One limitation of these chairs is that they are limited in the number of areas of the body they can support, while a surgical procedure requires the contribution of strength and coordination from several parts of the surgeon's body. These chairs also limit the surgeon from being physically independent. For example, the arm rests are stationary and require the surgeon to rest his or her arms on the arm rests in order to take full advantage of the arm-resting feature. This limits the full range of motion of the surgeon's arms to freely move around during surgery. The surgeon is required to sit in order to rest his or her legs and, therefore, is not able to walk or reposition his or her body relative to the patient, when needed, without moving the chair.

Perhaps the most well-known surgical robotic system is the da Vinci Surgical System. Since its inception, surgical robotic systems have advanced in their technological abilities. They now offer the surgeon a wider range of procedures that can be performed with increased accuracy and efficiency. The da Vinci Surgical System offers the ability for the surgeon to perform minimally-invasive surgery by using the robotic arms in real time and with increased accuracy while the surgeon controls the robotic arms from a console. Other robotic systems provide the surgeon the ability to pre-plan an operation using medical imaging technologies such as CT scans or x-rays of the patient's anatomy to pinpoint particular anatomical areas of interest and guide the robotic system's arms to a location where a surgical instrument can be used, or a medical device can be implanted. Both types of systems, while offering some advantages over a non-robot assisted surgery, lack the direct up-close interaction within the operative field that a surgeon has when performing surgery without a surgical robotic system. Also missing from these systems is the true haptic feedback that the surgeon has with the general environment he or she is working within, and specifically with the instruments and patient. Complex and time-consuming registration of the robotic system, with respect to the spatial relationship of the patient's anatomy, is another limitation of current robotic surgical technologies.

Other inventions not as technologically advanced as a surgical robotic system have been created to provide rigid support structures for the surgeon while he or she is standing. The support structures are strapped onto the surgeon's legs and allow the surgeon to distribute upper body weight through the support structures while the surgeon is in a half-standing, half-sitting posture. While inexpensive and simple, this system does not provide support to other areas of the body where physical exertion is occurring, for example, the back and neck. It does not provide the surgeon the capabilities that a surgical robot provides, such as precision guidance. As is the case with the surgical chair, this technology also limits the surgeon from freely walking or repositioning his or her body relative to the patient, when needed.

Exoskeletal systems, used for human physical enhancement, have become more popular in recent years as a means to maximize physical efficiency in various fields. Some areas in which they are being developed for use are the automotive industry, military, and human rehabilitation. These exoskeletal systems frequently consist of a series of pulleys, rigid structures, and motors to assist the wearer with movement by providing support, stability, and increased strength. Two characteristics of such systems is that they are heavy and bulky. Another characteristic is that they do not provide the same haptic feedback to the wearer that a person not wearing the system would have when coming in physical contact with objects. This limits the wearer's ability to interact with the environment in a complete and seamless way. Exoskeletal systems are able to provide assistance to a wearer needing to make medium to large sweeping actions such as walking or lifting heavy objects. However, they are limited in their ability to assist a wearer with making fine motor movements that require precision such as surgery. They can be limited to movement in only major planes of biomechanical motion. Adding degrees of freedom to joints, such as to the shoulder, increases the complexity and bulkiness of the exoskeletal system.

Surgical support structures and surgical robotic systems are two types of technologies that have been developed to assist a surgeon during surgery. While beneficial, they can be limited in the problems they address. Embodiments of the present invention fuse the benefits that these two technologies provide with a new type of exoskeletal technology that is not bulky and heavy in nature. Most importantly, this new type of technology seamlessly integrates with the user's motion and greatly enhances surgery in a more comprehensive way. The core technology can also be used in fields other than surgery.

DESCRIPTION OF INVENTION

Neuromuscular Enhancement Systems such as those described herein; embodiments of which are referred to herein as an NES, can be described using any of the following names: Actuating control system, Actuating enhancement surgical system, Actuating robotic system, Actuating surgical robotic system, Actuating wearable surgical robotic guidance system, Advanced material enhancement system, Advanced material surgical guidance system, Advanced textile surgical system, Exo-muscle, Guided surgical muscle system, Innovative surgical stabilizing technology, Limb precision and fortification system, Microsurgery precision enhanced system, Microsurgery support console, Muscle armor, Muscle assist device, Muscle enhancement system, Muscle suit, Muscle surgical assist system, Neuromuscular Enhancement System, Neuromuscular garment enhancement system, Smart enhancement fabric, Smart enhancement textile, Smart textile surgical system, Smart wearable surgical system, Soft enhanced robotics, Soft robotic surgical assist, Soft robotics guided surgery, Soft surgical robotic assist system, Soft surgical robotics technology, Surgeon limb support system, Surgery accuracy and support console, Surgery accuracy and support skeleton, Surgery support console, Surgical accuracy and support enhancement scaffold, Surgical accuracy and support enhancement suit, Surgical enhanced precision system, Surgical garment enhancement system, Surgical reinforcement console, Surgical stabilization technology and innovative interface, Surgical stabilization technology and innovative machine-human interface, Surgical stabilization technology and innovative navigation systems, Surgical stabilization technology and innovative robotic interface, Technology for surgical stabilization innovations, Wearable actuating control system, Wearable actuating enhancement system, Wearable robotics, Wearable surgeon assist system, Wearable surgical guidance, Wearable surgical robotics.

BRIEF DESCRIPTION OF DRAWINGS

FIGS. 14-16 provide schematic illustrations of various embodiments of actuating units that allow for the pumping of matter through the embodiments.

FIG. 19 is a schematic illustration of an embodiment of an actuating material contracting due to the removal of matter.

FIGS. 21-22 provide schematic illustrations of various embodiments of actuating materials that contain magnetically controlled regions.

FIG. 29 is a schematic illustration of actuating materials with graphs depicting their contribution made to raise an arm.

FIGS. 38-40 provide schematic illustrations of the actuating materials exhibiting the ability to provide snugness.

FIGS. 48-56 provide schematic illustration of various embodiments in which power is supplied.

MODES OF CARRYING OUT THE INVENTION AND INDUSTRIAL APPLICABILITY

Figure 1:
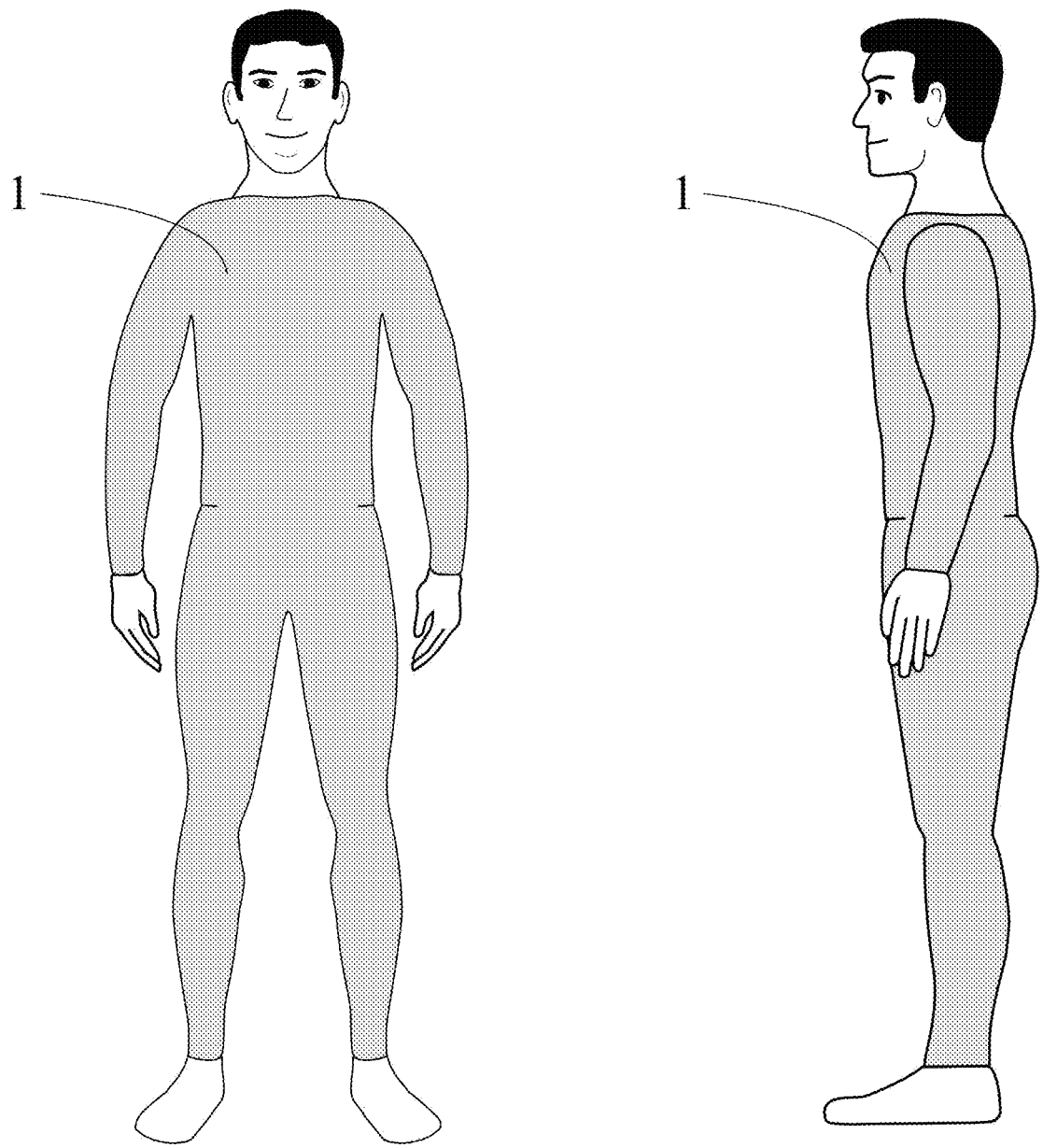
FIG. 1 is a schematic illustration of the embodiment.

Embodiments of the present invention can enhance a user's ability to perform activities for longer hours and with increased accuracy. The invention, referred to as the Neuromuscular Enhancement System, or NES, is composed of engineered textile material fabric structures that contour to the user's body FIG. 1. These structures 1 impart forces, through changes in their geometric configuration, against the user's own body to induce a desired outcome. Examples of desired outcomes include the ability to generate motion, provide stability, and enhance the user's strength. The NES is embedded with various sensor technologies that assist in making the desired outcome occur.

Methods for Actuation: The term actuating will be used to describe the actions carried out by the engineered textile material fabric structures, sometimes called engineered fabrics. The engineered textile material fabric structures will be defined as the following: actuating materials. These materials carry out their actuating features through changes in their geometric configuration. Through these changes, they provide the forces needed by the NES to induce a desired outcome. For example, an actuating material can contract and apply a tensile force when it is activated with energy. Conversely, an actuating material can induce a desired outcome by expanding and providing a pushing force or tensile force onto another object. An actuating material can apply its force by becoming rigid in nature. It can also be composed of hybrid materials and or structures that produce a force upon actuation.

Controlling Actuating Materials: An NES can comprise one or more than one layer of actuating materials. It can be embedded, within these layers, with sensors that serve various purposes to assist in the function of the NES. For example, position sensors can be employed to provide information about the position of the NES or portions of it. They can also be used to detect the desired motion of the user and, therefore, assist in affecting outputs of the NES based on the anticipated motion of the user.

Characteristics of the NES Fabric: The materials that comprise the NES have the pliability of clothing and the ability to wrap around the contours of the user's body. This ability to contour around the user's body will be defined as contourability from this point forward. The NES contours around the body of the user in a manner similar to a swimmer's wetsuit. It is flexible in nature and does not add significant weight to the user.

Component Embodiments of the NES: The NES can cover a user's entire body or sections of the user's body. Other embodiments of the NES exist as component pieces of a complete NES that cover only certain portions of the body. These various embodiments allow a user to only enhance certain regions of the body instead of the entire body, if the user wishes to do so.

Supplying Power to the NES: Various methods exist to supply power to the NES and to all its components. The units that store the power can be modular in shape as well as portable. They can connect to the NES so that the NES is not tethered to one particular location for it to receive power. The power can also be supplied from a stationary location that requires the NES be connected through a cable or a tube at all times.

Information Processing of the NES: The NES can be equipped with various sensors to collect information about the NES and its surroundings and to assist in its function. The data collected is processed with a computer system, referred to as the NES computer or the control system from this point forward. The control system can comprise a general purpose computer, an embedded computer, a computing system such as in contemporary smart phones, special purpose electronics such as ASICs or FPGAs, a microcontroller, a computer remote from the NES and communicating with the NES via a wired, optical, or wireless communications facility, or combinations of the foregoing or other processing and control systems known in the art. The computer system is used to operate the NES in a feedback loop. Other systems such as medical imaging equipment can exist within this feedback loop. Using the data that it collects, the NES can operate in a semi-autonomous or fully-autonomous state. It can also employ principles of artificial intelligence.

Hybrid Embodiments: The NES is capable of interfacing with exoskeletal systems or components of exoskeletal systems. Embodiments of the NES can also be composed of components that are used to construct and operate an exoskeletal system, for example, rigid structures, pulleys, and motors. This hybrid construction can further enhance the capabilities of the NES.

The NES used in Surgery: The NES can be used by a surgeon to increase his or her stamina and ensure better outcomes for the patient. A number of technologies can be used in combination with the NES during surgery to improve accuracy and ensure optimal delivery of care. For example, imaging systems and navigation systems can seamlessly pair with the NES to provide the most advanced surgical care.

Other Applications for Neuromuscular Enhancement Systems and or Technologies: In addition to surgery, the NES can be used in a variety of industries, each of which have an array of applications within the industry. The NES technology as a whole, the NES as a stand-alone embodiment, or the fundamental engineered textile materials can be used in these industries.

I—Methods for Actuation

Figure 2:
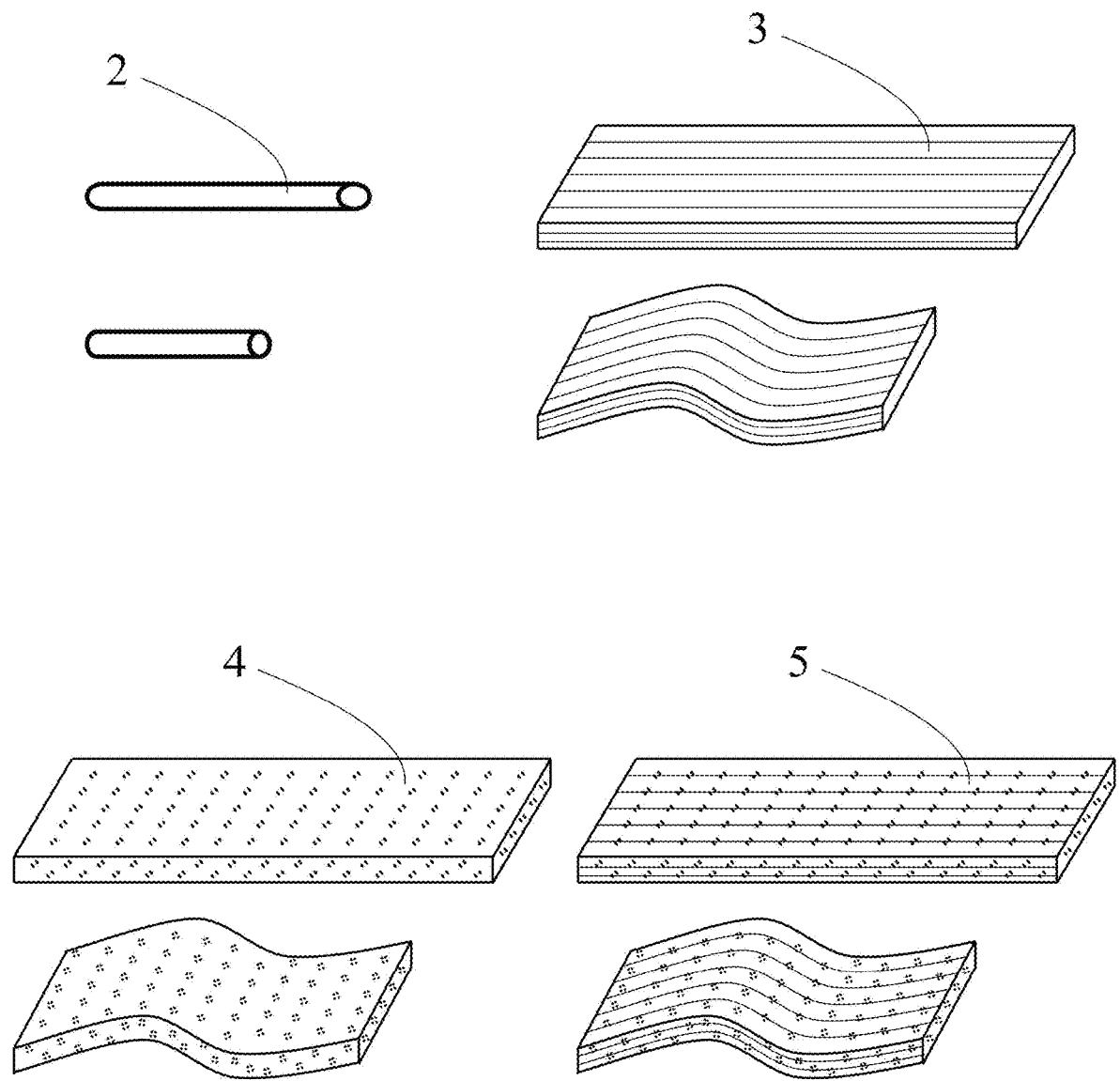
FIG. 2 is a schematic illustration of actuating materials.

Embodiments of an actuating material structure can take various forms: an actuating textile substructure, a continuous piece of textile material that actuates without the aid of an actuating textile substructure or substructure, a continuous piece of textile material that actuates due to the actuating substructure or substructures within it, and a continuous piece of textile material that actuates on its own and or with the aid of an actuating substructure or substructures contained within it. Due to their actuating nature, these textile materials FIG. 2 will be referred to, respectively, as: an actuating substructure 2, continuous actuating material 3, non-continuous subactuating material 4, combination actuating material 5. When referring to these materials in a general sense, without needing to distinguish between any of the four embodiments just described, the term actuating material will be used. Other materials from which the NES is composed can be non-actuating materials that consist of sensors and or other components, and regular textile materials. Embodiments of the NES can consist of one or more of these materials.

Figure 3:
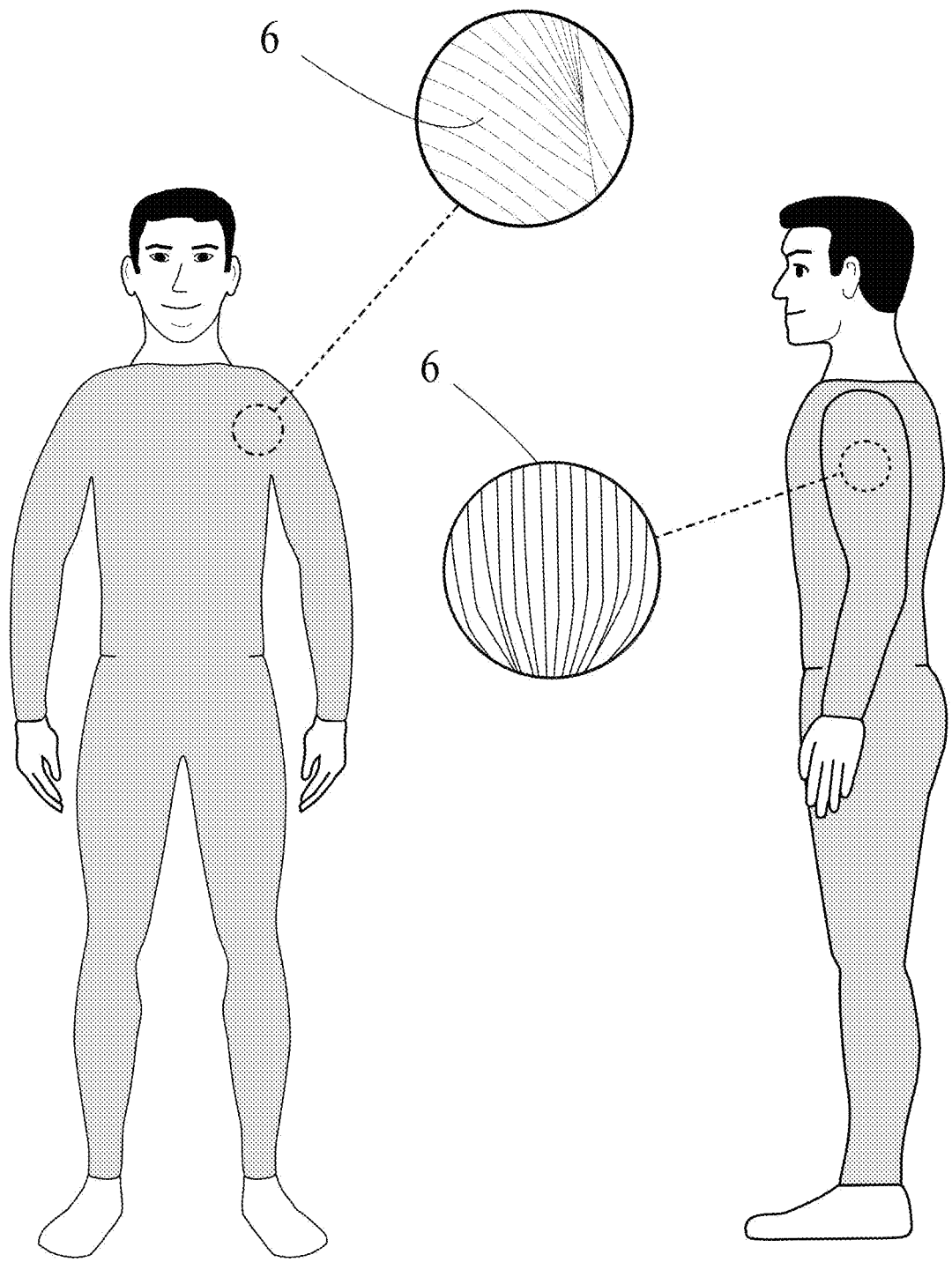
FIGS. 3-4 are schematic illustrations of actuating material configurations.
Figure 4:
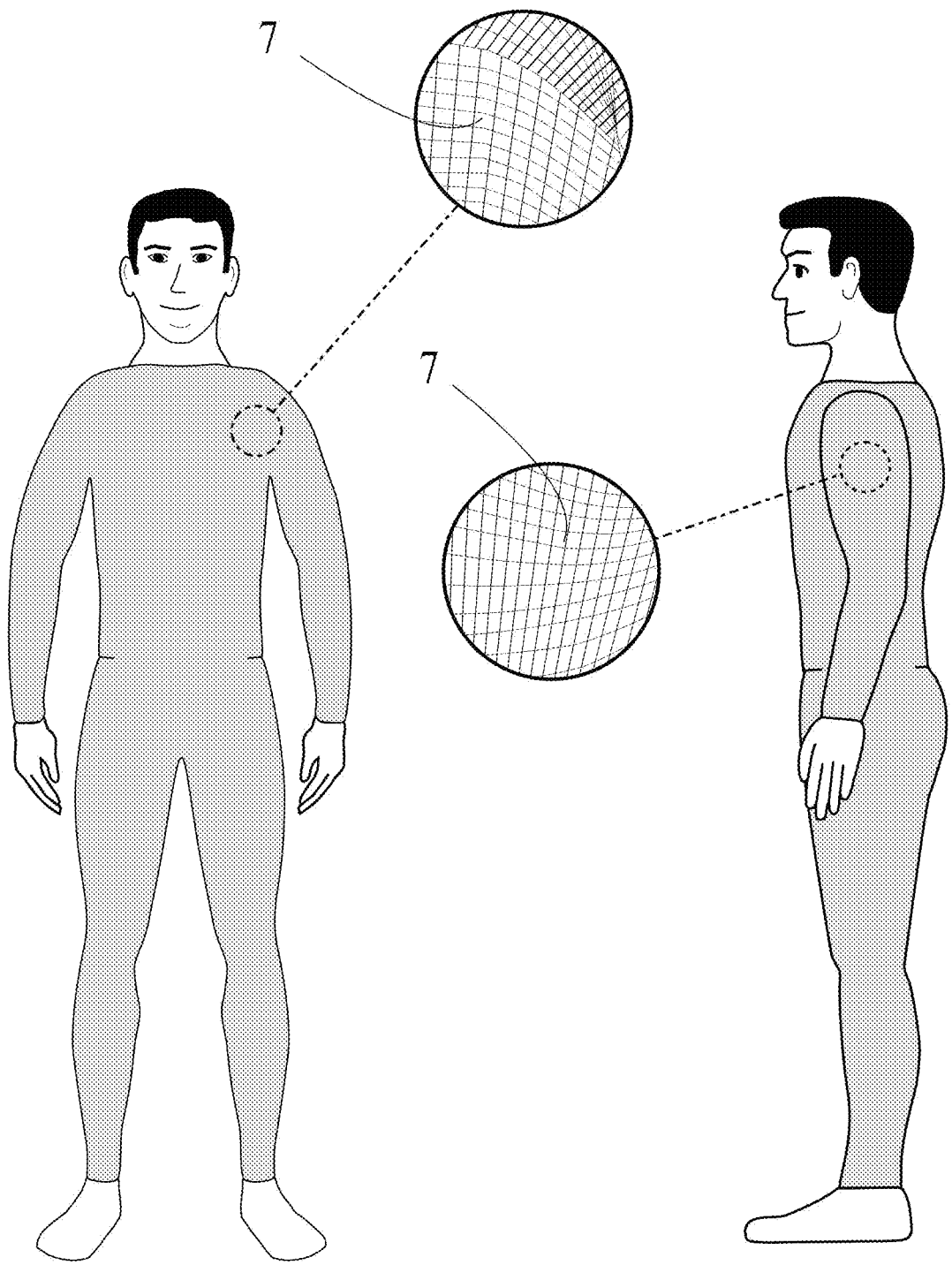

Actuating Geometries: The actuating material can exist within its layer, as shown in FIG. 3, positioned side by side in a longitudinal pattern along the length of a given area of the user's body 6, or perpendicular to the long axis of any given area of the body. Or, as shown in FIG. 4, it can be a lattice of actuating materials that crisscross each other 7. These layers of actuating materials will impart the forces required to achieve the desired motion or to maintain a desired position by the user.

Any pattern or geometric configuration found in nature, such as the shape of a snowflake, can be modeled after and manufactured into actuating material to provide mechanical power when used in the NES. The patterns can also be based on geometric configurations that are used in the construction of buildings, bridges, and or other structures. These structures can also be a combination of actuating material patterns that include a multitude of distinct patterns. An example of a pattern is a lattice of interconnected shapes containing centralized nodes. When activated, a node or group of nodes, can apply forces to an adjacent node or group of nodes to pull the node or nodes in a certain direction, and thus apply a desired force. One embodiment of the centralized node pattern is that of a snowflake pattern. In this embodiment, each node controls and applies forces to arm-like structures extending from the node and connected to other nodes. Another embodiment uses the concept of a McKibben muscle. In this muscle model, a textile mesh encompasses a tube that can be filled with air. When the tube expands, the mesh contracts, as its circumference expands. An embodiment that consists of McKibben muscles in the shape of a hexagon, or other geometric configurations, can be used to actuate in various directions with the control of the McKibben muscles. Any actuating material, such as an electroactive polymer, can be used in place of the McKibben muscle. In another embodiment, a dome structure is used where the increase in the height of the dome causes the contraction of the supporting dome structures, thus inducing a force on an adjacent object. Actuating materials can lie side by side in a linear fashion and actuate along their long axis. Other embodiments of the actuating material can consist of electroactive polymers, electroactive elastomers, photoactive polymers, and McKibben muscles that actuate and provide a force to an adjacent object.

Figure 5:
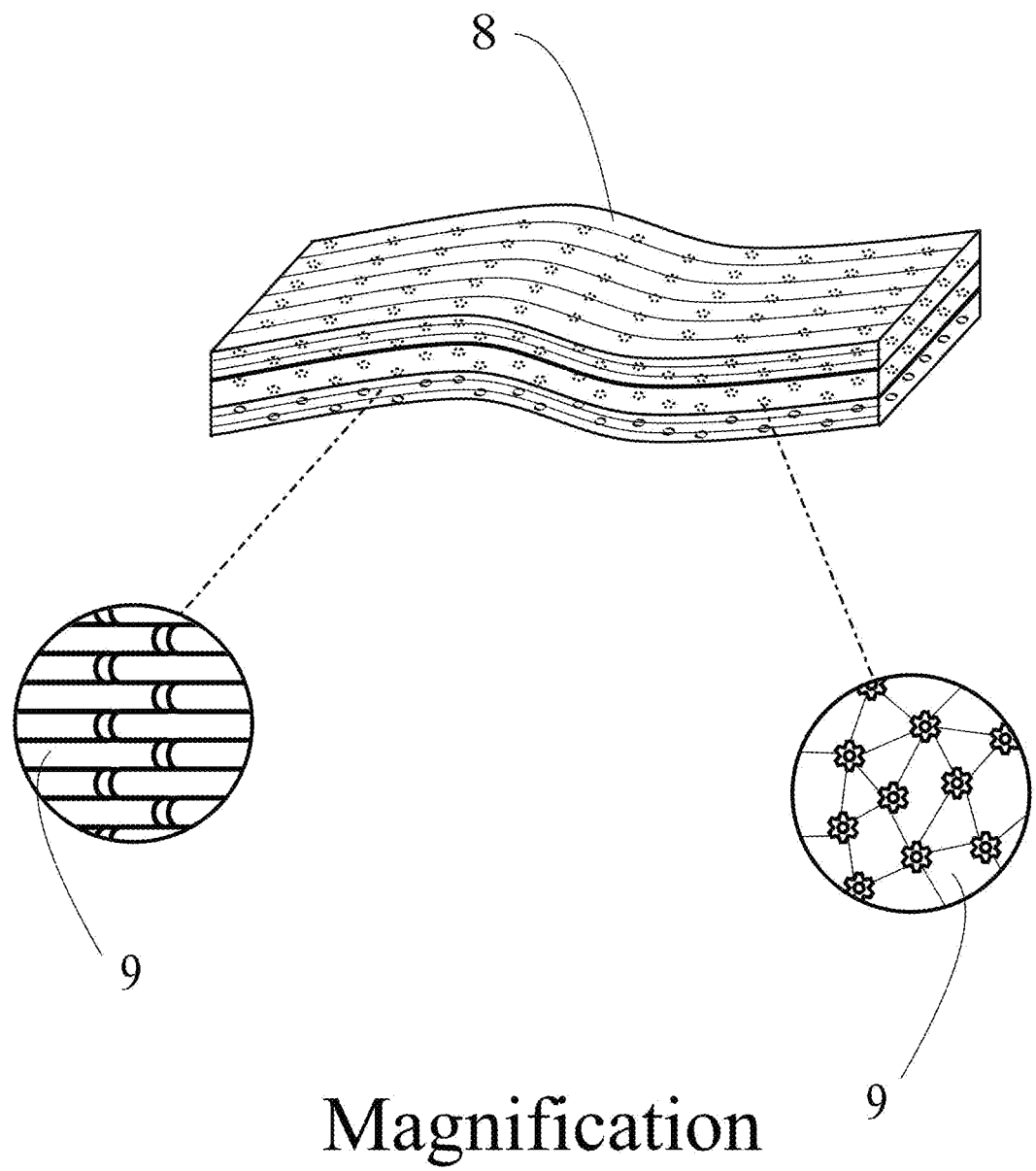
FIG. 5 is a schematic illustration of actuating substructures within an actuating material.
Figure 6:
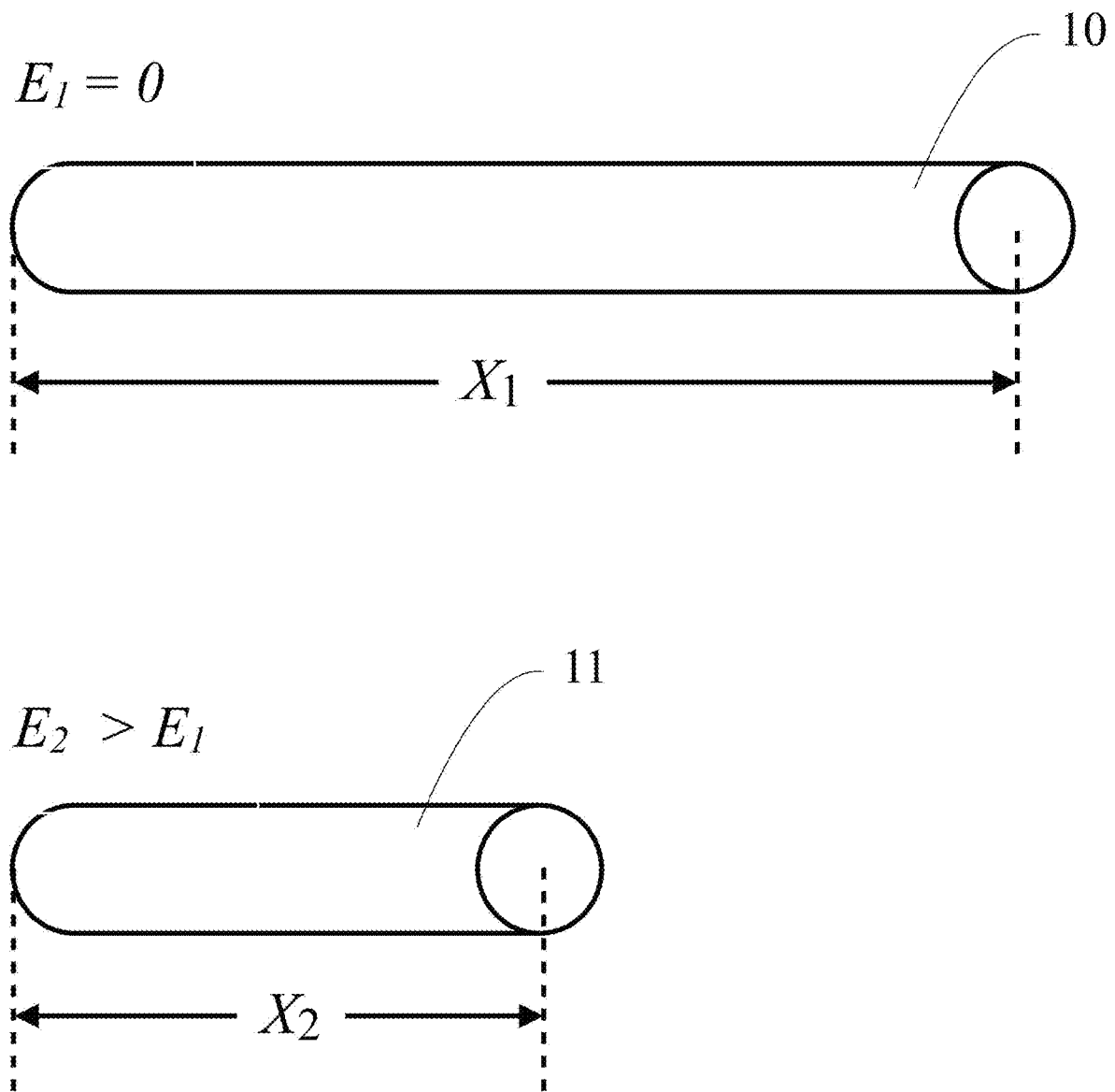
FIG. 6 is a schematic illustration of an actuating material in a relaxed state and an actuated state.
Figure 7:
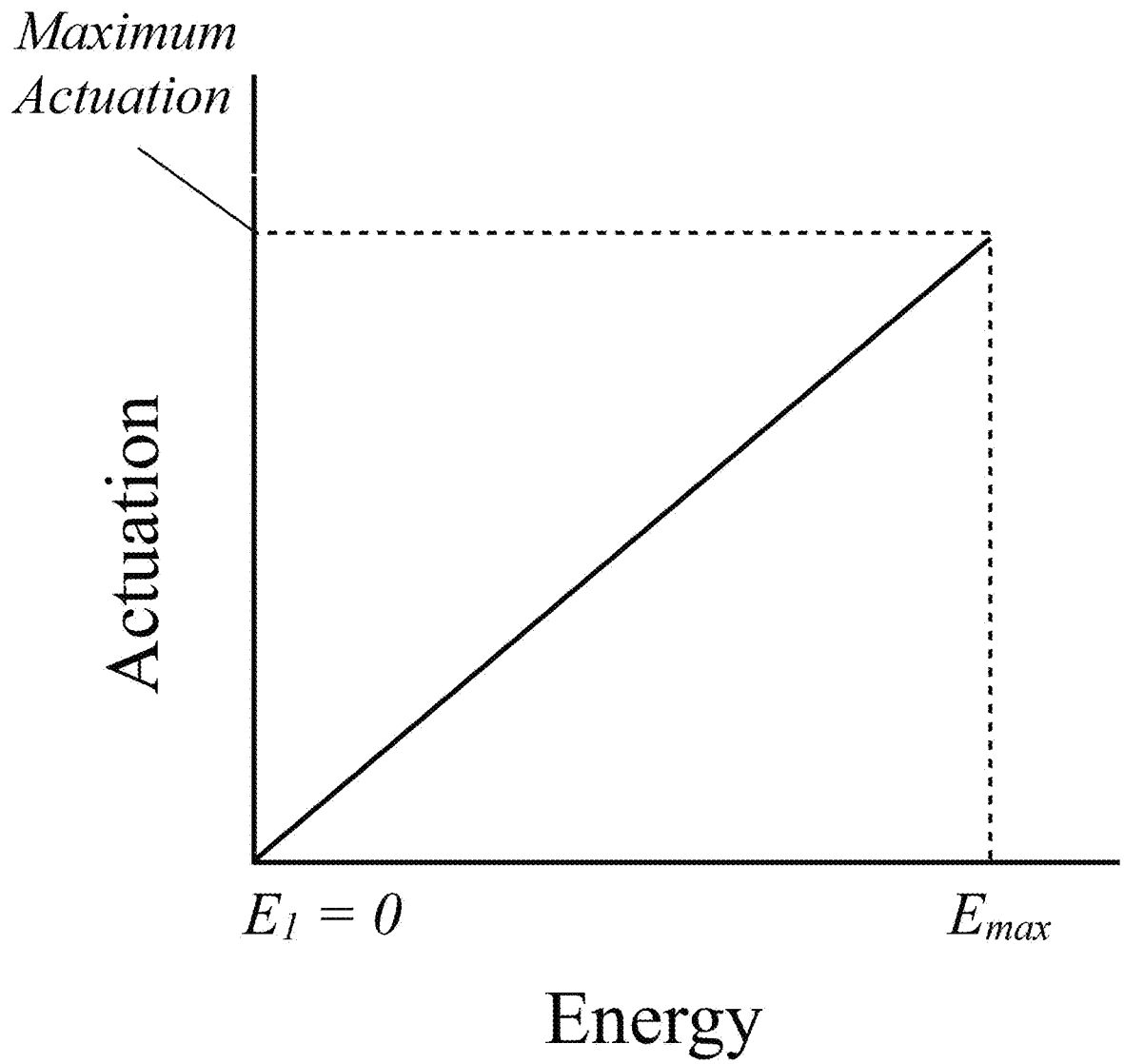
FIG. 7 is a schematic illustration of actuations as a function of energy.
Figure 8:
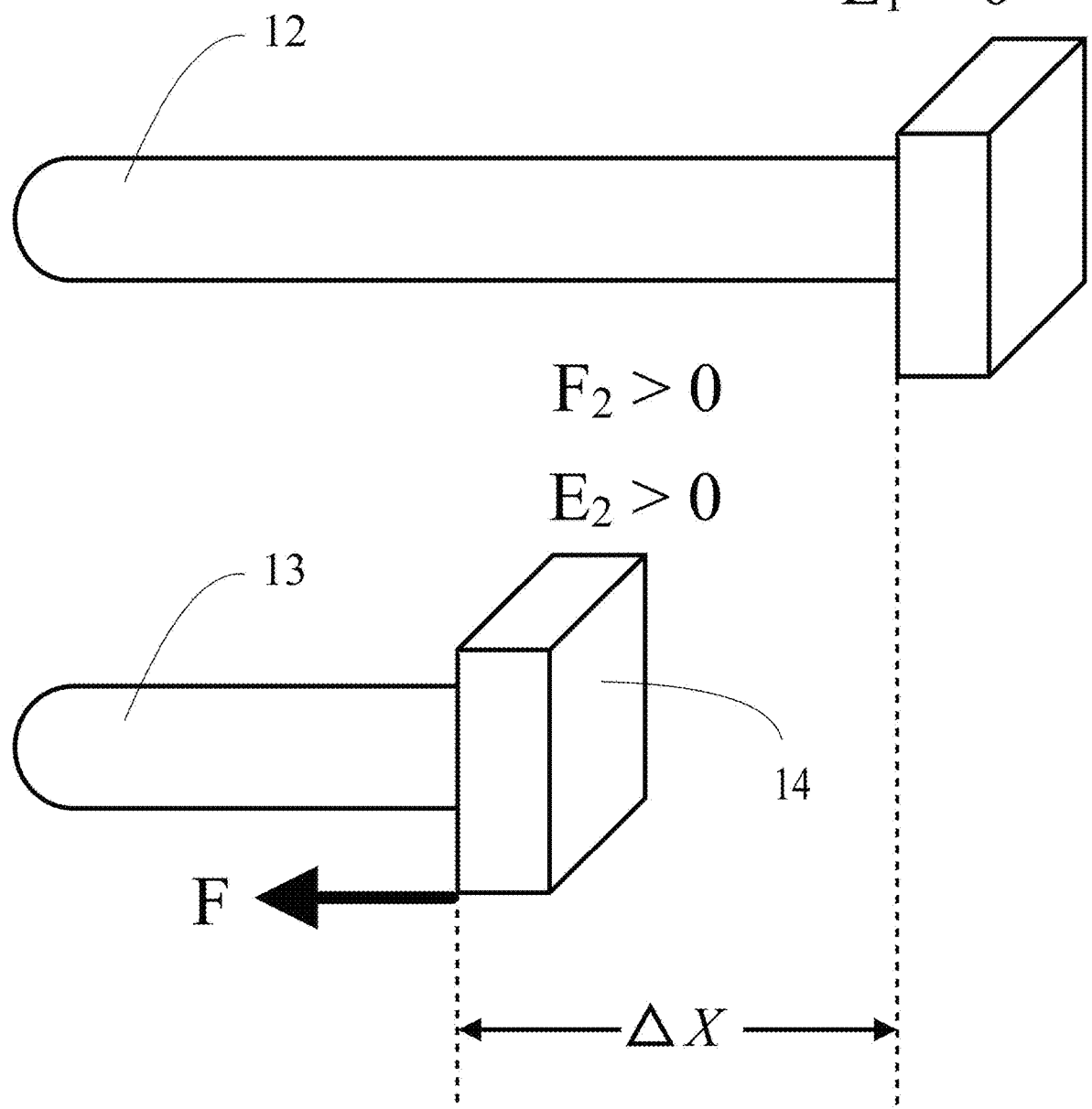
FIG. 8 is a schematic illustration of an actuating material actuating and applying a force to an adjacent object when energy is applied to the actuating material.

Actuation of the Actuating Materials: An NES provides physical assistance to the user through layers, as shown in FIG. 5, of actuating materials 8. Within the layers of actuating materials can exist actuating substructures 9. An actuating material, as shown in the embodiment of FIG. 6, exists in a relaxed state 10 and actuates 11 when energy is applied to it. The relationship in the amount of actuation vs. energy can exist in a directly proportional way as shown in FIG. 7. The energy that actuates the actuating material can be in the form of electricity, magnetism, temperature gradients, electromagnetic radiation, fluid pressure, or any other form of energy. When an actuating material is in a relaxed state 12, as shown in FIG. 8, and then actuates through the application of energy 13, it changes its geometric configuration and imparts a force to an adjacent actuating material or object 14. The amount of change is based on the amount of energy introduced, and the amount of energy introduced in based on the desired output from the actuating material.

When the actuating material is not in an actuating state, it is relaxed and is able to return to a baseline geometric configuration. This relaxed state means that little to no force is being applied to adjacent actuating materials or objects. Physiologically speaking, these actuating materials act in a way similar to muscle fibers in that they have the ability to apply forces when activated with energy and relax when energy is removed. Mechanically speaking, these materials perform in a way similar to a mechanical power unit that imparts motion, such as a motor. The user, in essence, will be wearing a muscular system. The system will use the user's own body in a manner similar to the way skeletal muscles use the skeletal system to induce a desired outcome: by applying forces to the skeletal system.

Activating the Actuating Material Through Various Means

Physical changes of actuating material can be initiated through the application of energy to it. The type of energy that initiates changes in the materials can be from a variety of different types of energy. For instance, the application of electricity, magnetism, temperature gradients, electromagnetic radiation, fluid pressure, or any other form of energy imparted onto an actuating material can initiate a change in it.

The actuating materials of an NES can comprise any number of materials that exhibit a change in their characteristics or properties through the introduction of various types of energy stimuli. They can comprise any of the following materials, a combination of the following materials, or a material not listed here: piezoelectric materials, shape-memory polymers, magnetostrictive materials, magnetic shape-memory alloys, smart inorganic polymers, temperature-responsive polymers, ferrofluid materials, dielectric elastomers, magnetocaloric materials, thermoelectric materials, hydraulic response materials, pneumatic response materials, soft robotics materials.

Figure 9:
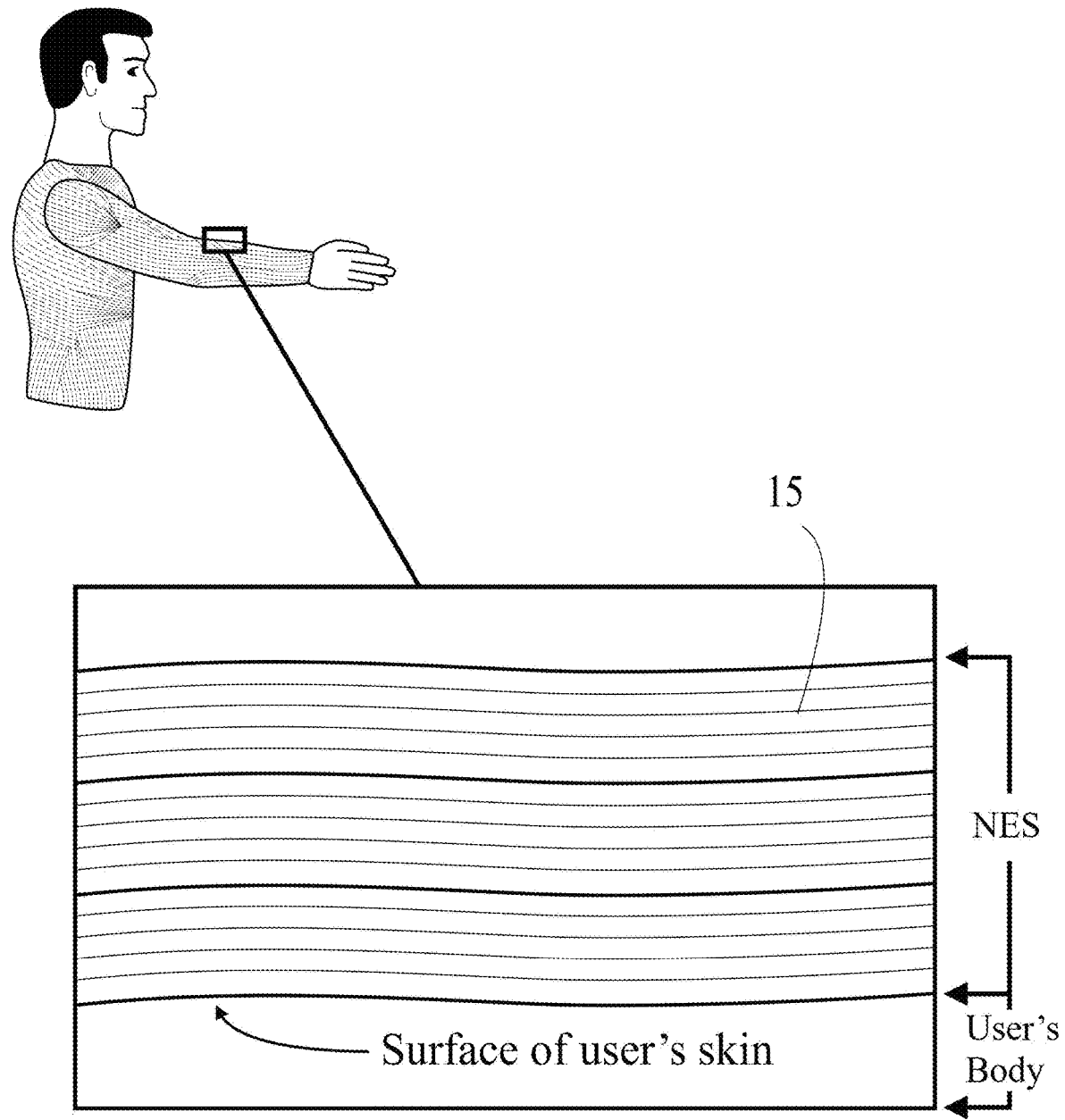
FIGS. 9-11 provide schematic illustrations of various embodiments of actuating materials.
Figure 10:
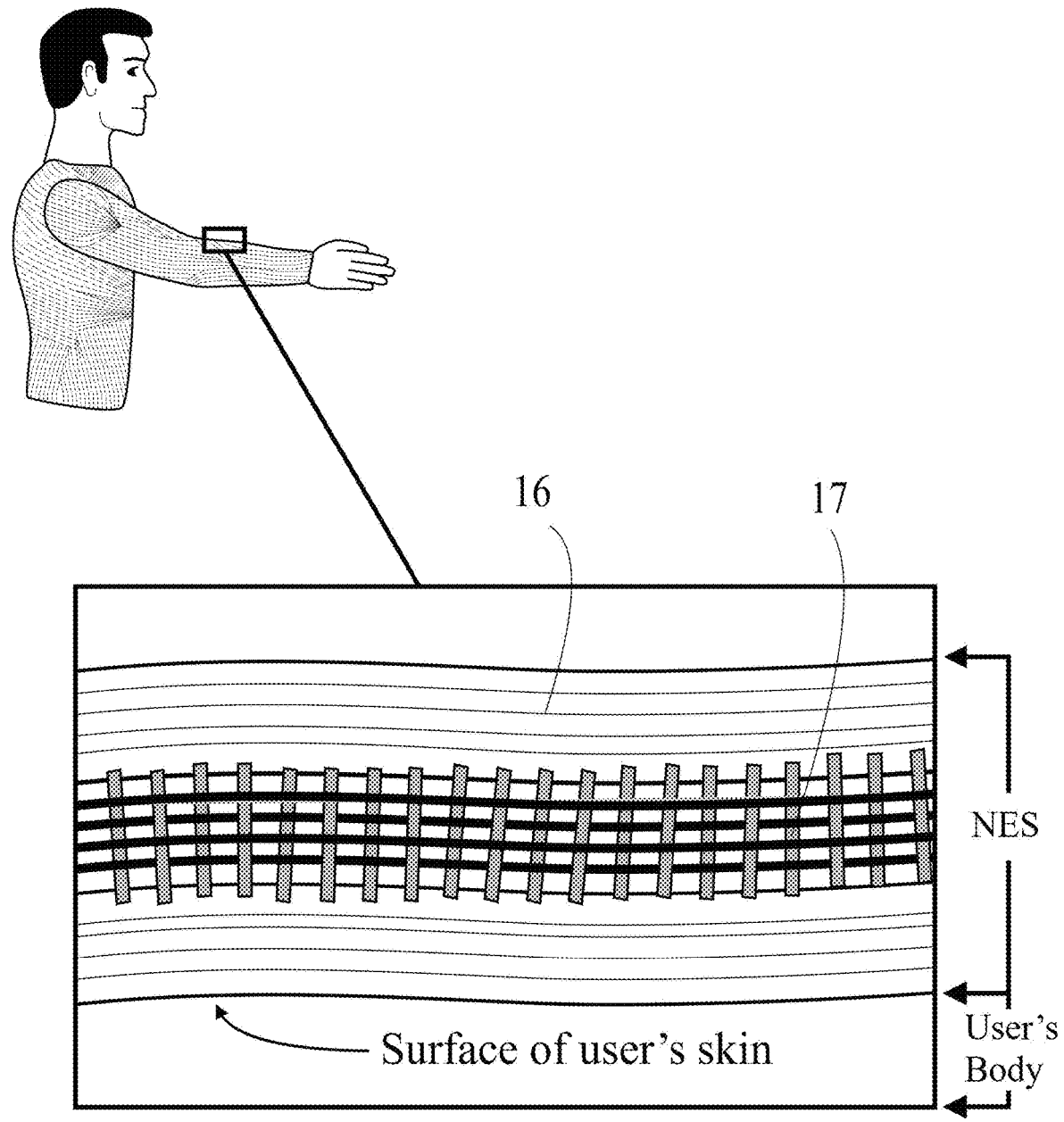
Figure 11:
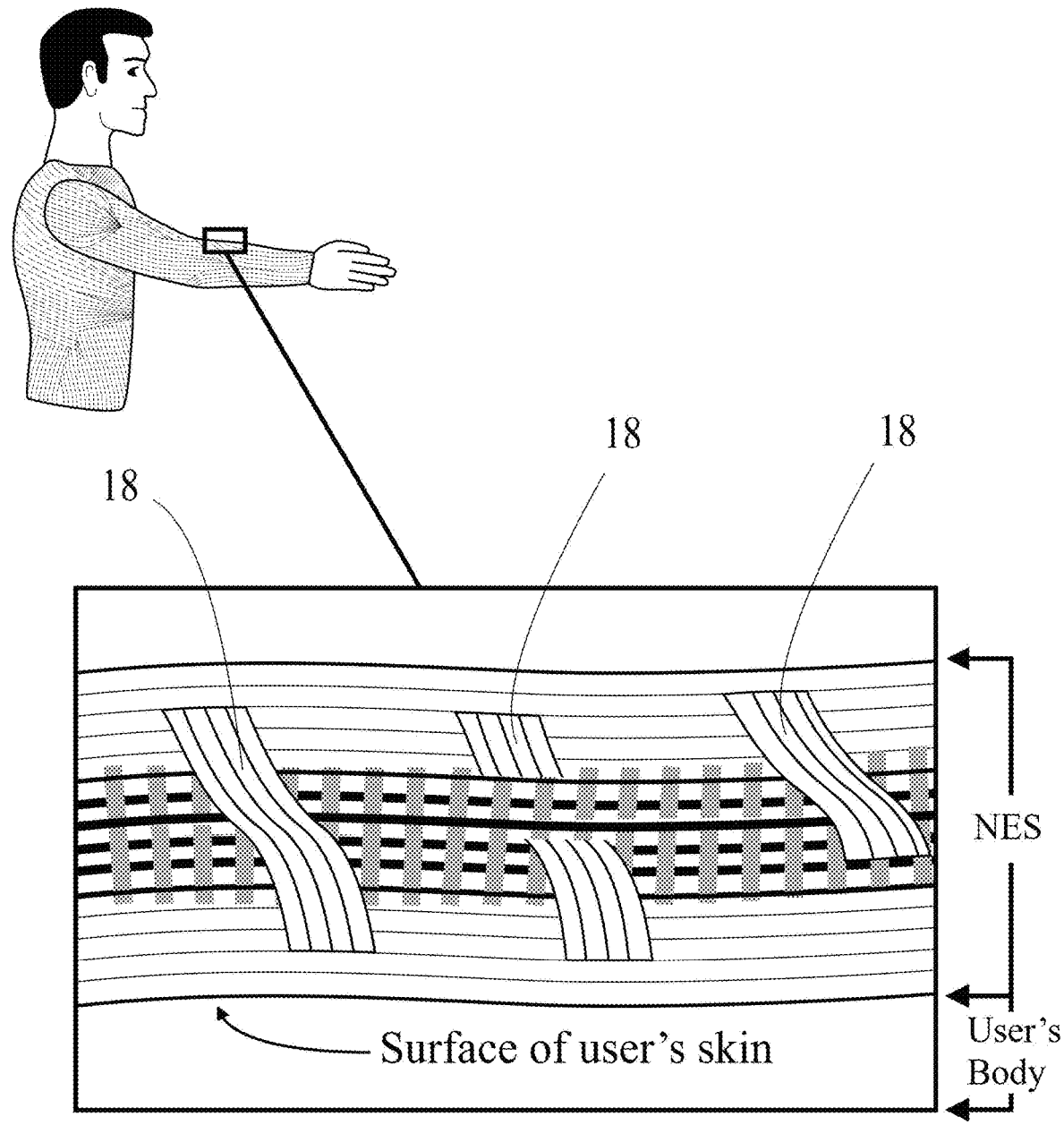

The actuating materials of an NES, as shown in FIG. 9, can be composed entirely of actuating substructures 15, or exist as a network, as shown in FIG. 10, of actuating substructures 16 and materials that do not change when an energy stimulus is applied 17. These layers, as depicted in the figure, exist in a continuous uninterrupted manner through the extent of the entire layer while not crossing into other layers. The layers, as shown in FIG. 11, can also be intertwined with other layers. In other words, the layer can cross into one or more than one other layer of the NES 18.

Figure 12:
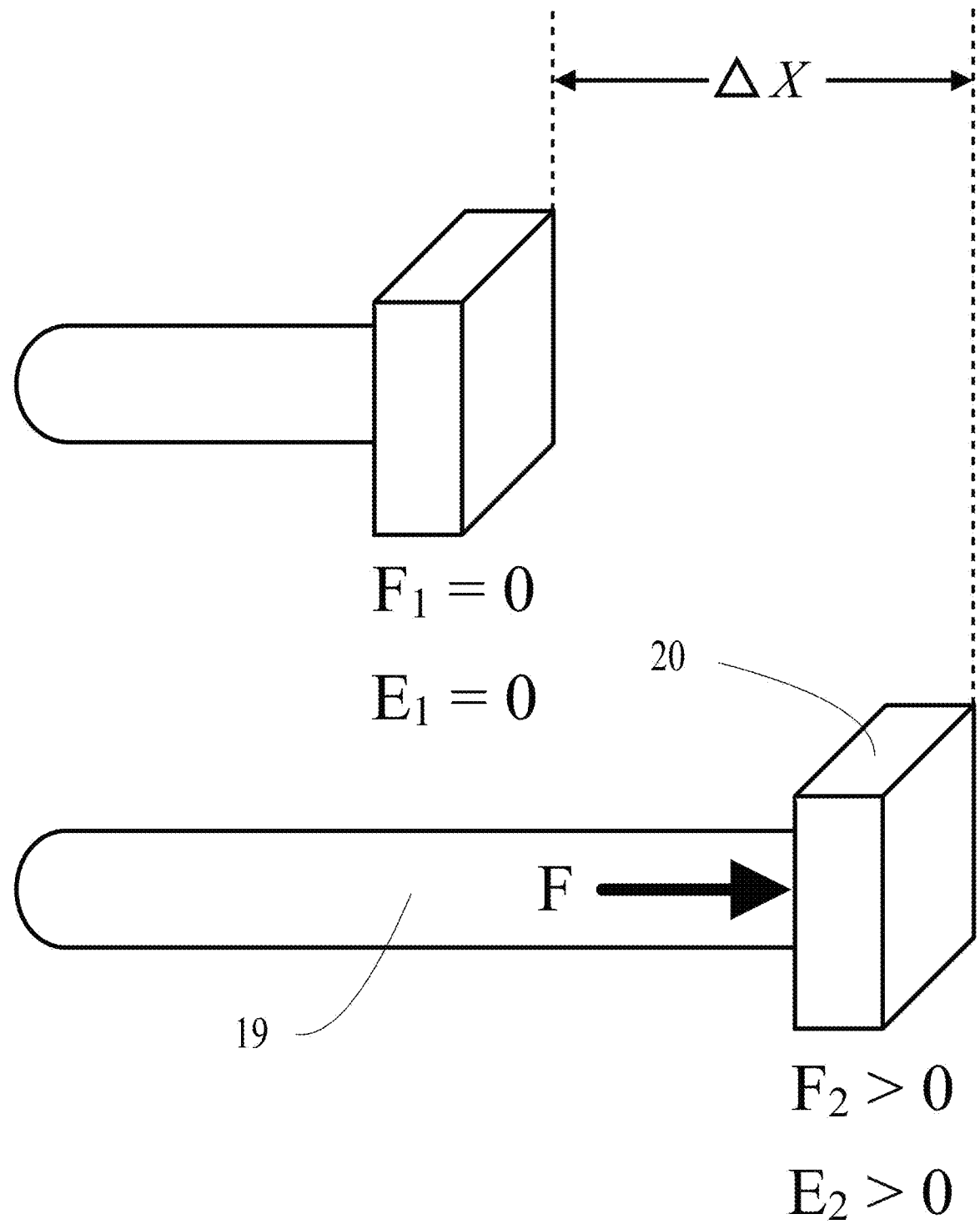
FIG. 12 is a schematic illustration of an actuating material actuating and applying a force to an adjacent object when energy is applied to the actuating material.

As previously mentioned, the actuating material will apply its force through the change in its geometric configuration. This change will impart a force upon whatever object is attached to it. When in a resting state, the actuating material will return to its baseline geometric configuration exhibiting little to no force on adjacent actuating materials or objects. It may return to its baseline shape without the application of energy, or with the application of energy. The type of energy required to return the actuating material to its normal baseline geometric configuration, if energy is needed to do so, could be any of the forms of energy previously described. Or it could be through the normal movement of the user and would require very little force, on the part of the user, to return it to its baseline shape. In another embodiment, represented by FIG. 12, the actuating material can expand 19 to achieve the same application of force to an object 20 connected to it through an increase in its volume through the methods previously described.

Figure 13:
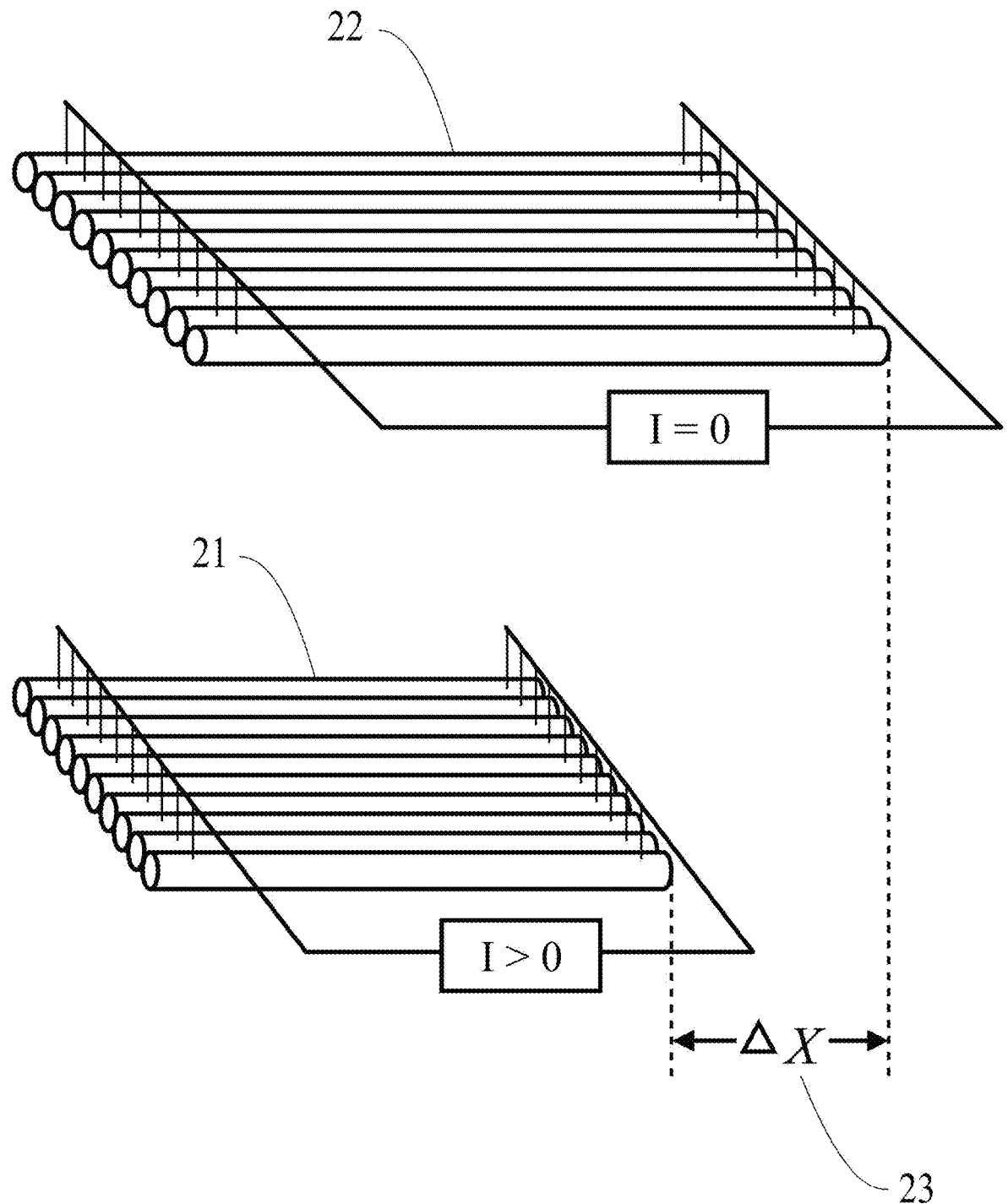
FIG. 13 is a schematic illustration of actuating materials contracting under the application of energy.

Electricity: In an embodiment, a change in the geometric configuration of an actuating material can be achieved through the application of an electrical current to the actuating material, as shown in FIG. 13. To achieve this change, a group of actuating material can have an electrical current applied to them 21 in order to make them contract, for instance. To return to a relaxed state, the actuating material can have the electrical current reduced or completely removed 22. The amount of change exhibited by the actuating material 23 can be directly proportional to the amount of current applied to it. The force imparted by the actuating material can be a function of the changes in the material.

Pressure Through the Introduction of Matter: Various embodiments of actuating material allow for the flow of matter through them. The geometric configuration of the actuating material can change with the flow of matter within it. The matter that can be used to flow within an actuating material causing a change in its geometric configuration is not limited to one type of matter. A multitude of types of matter can be used to flow through an actuating material to cause changes in its geometric configuration.

Figure 15:
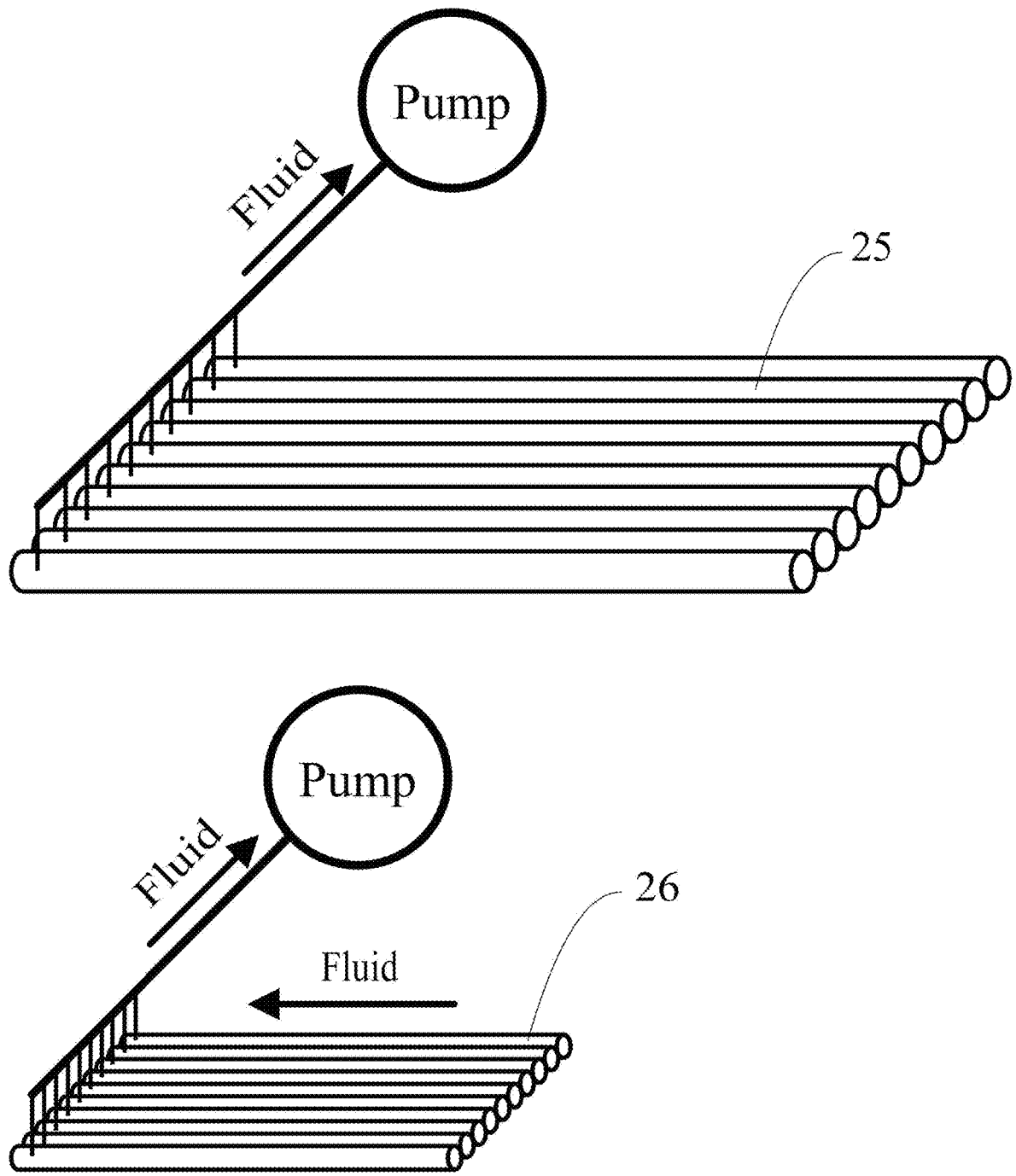

The phase in which a type of matter exists can be from its entire spectrum of phases and can also have varying degrees of rheological properties. For example, in one embodiment, as depicted in FIG. 14, a fluid such as air or water can be used to change the geometric configuration. A fluid can be pumped into a group of actuating units by the NES user, an assistant, or by a mechanical or automated means to increase the volume of the actuating material. This can lead to a change in the compressive force, for example, exhibited by the actuating material 24 on an object connected to it. A paste, as an example of a material that lies on the more viscous end of the rheological spectrum, can cause the same outcome on the actuating material by having it pumped into the actuating material. When the paste is extracted from the actuating material, the pressure within the actuating material decreases, causing a change in the amount of force being applied by the actuating material to an object connected to it. The opposite can also be true, as shown in FIG. 15. The normal state of the actuating material, not exhibiting tension 25, can be changed with the subtraction of matter causing the volume of the actuating material to decrease and thus the tension exhibited by the actuating units to increase 26.

The system contains safety features to prevent the leakage of fluid to critical circuitry that can damage the system or cause injury to the user or others by electric shock. If there were a breach in the actuating material and fluid could come into contact with critical circuitry or potentially harm the user or others, a fail-safe feature is triggered that immediately cuts power to the system. Another measure of safety is that low-voltage power can be used to power the system, ensuring that the user is not harmed if such a fluid breach were to occur.

Figure 16:
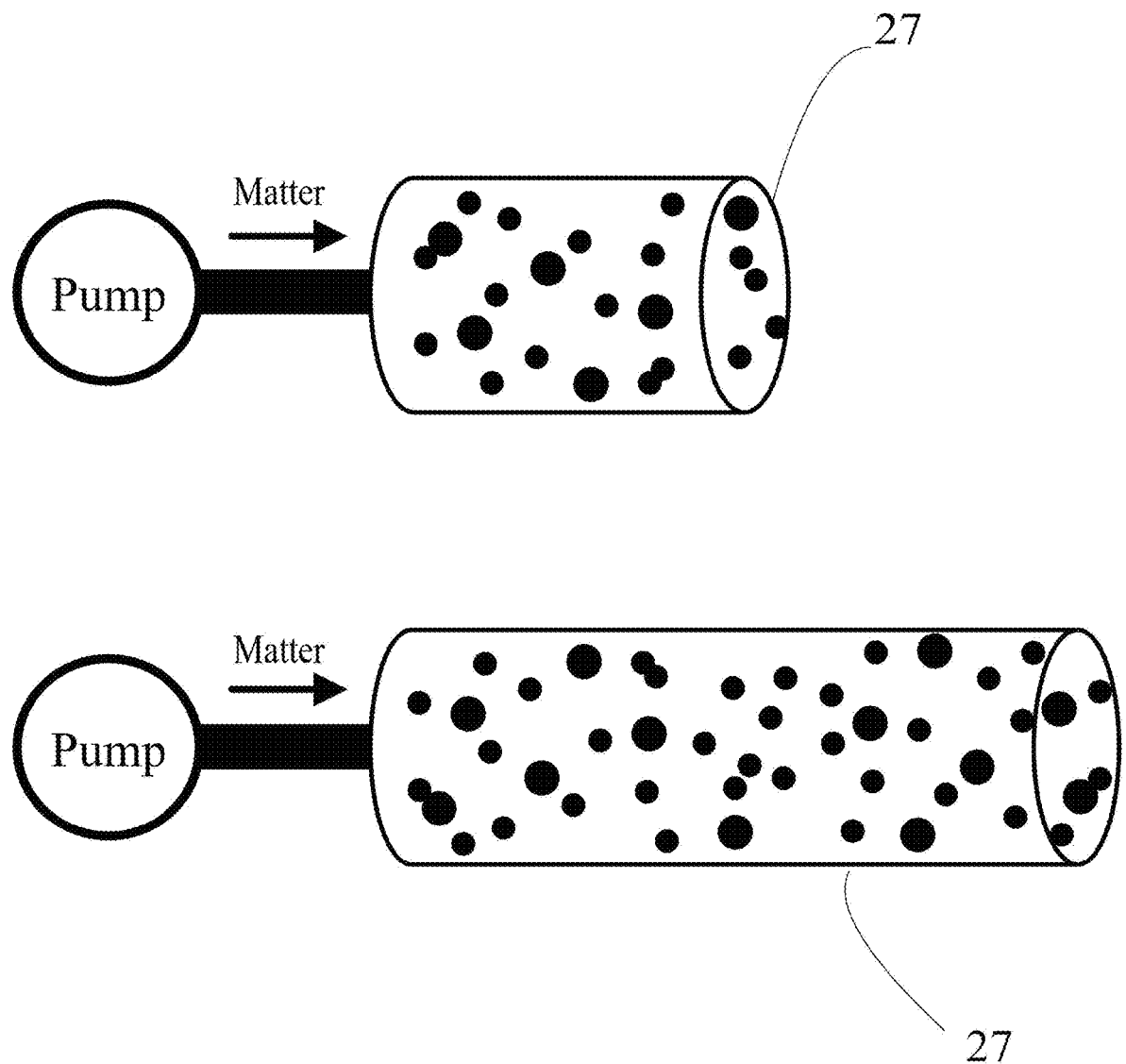
Figure 17:
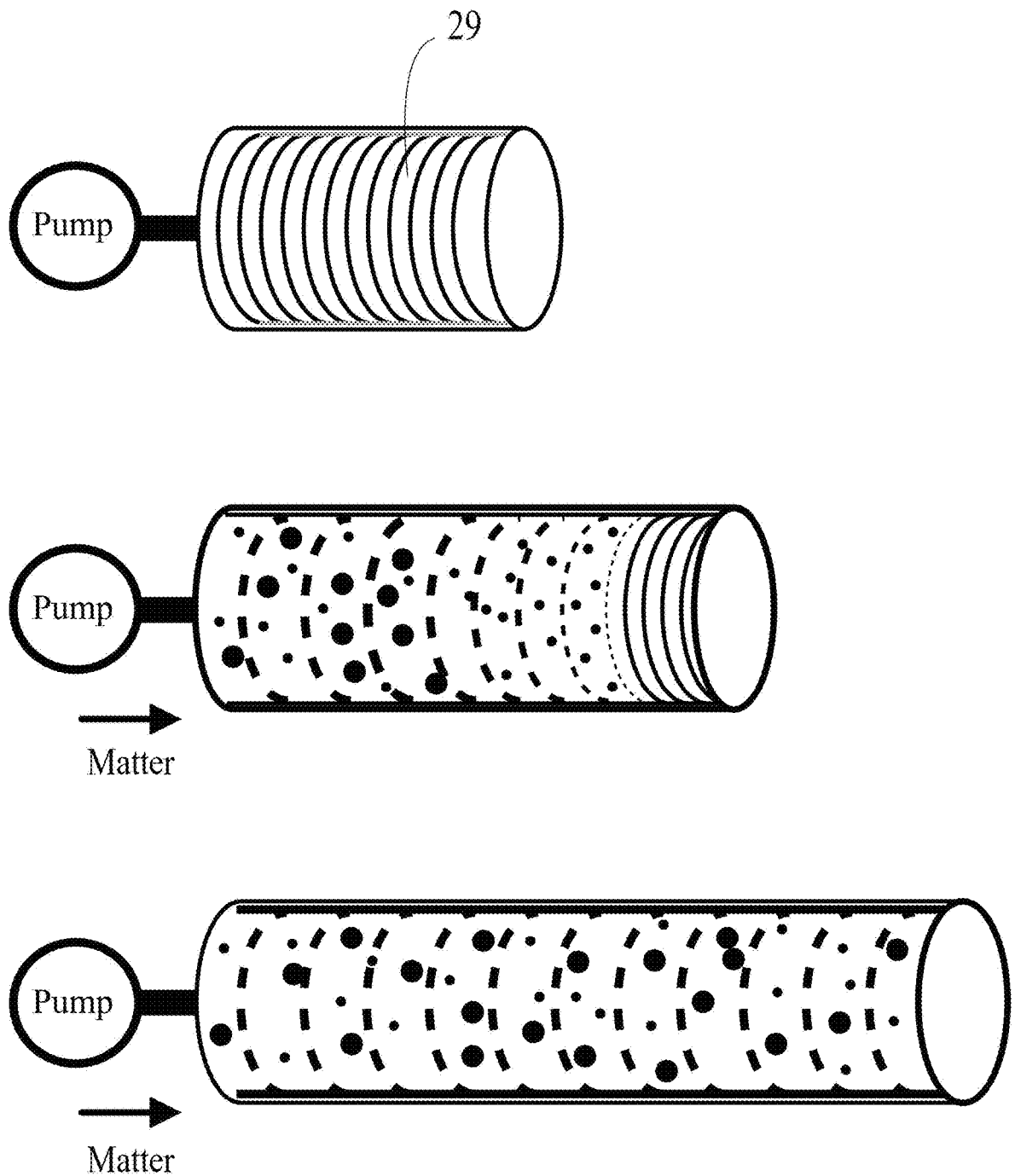
FIG. 17 is a schematic illustration of an embodiment of an actuating material that contains permeable cells and can have matter flow within it.
Figure 18:
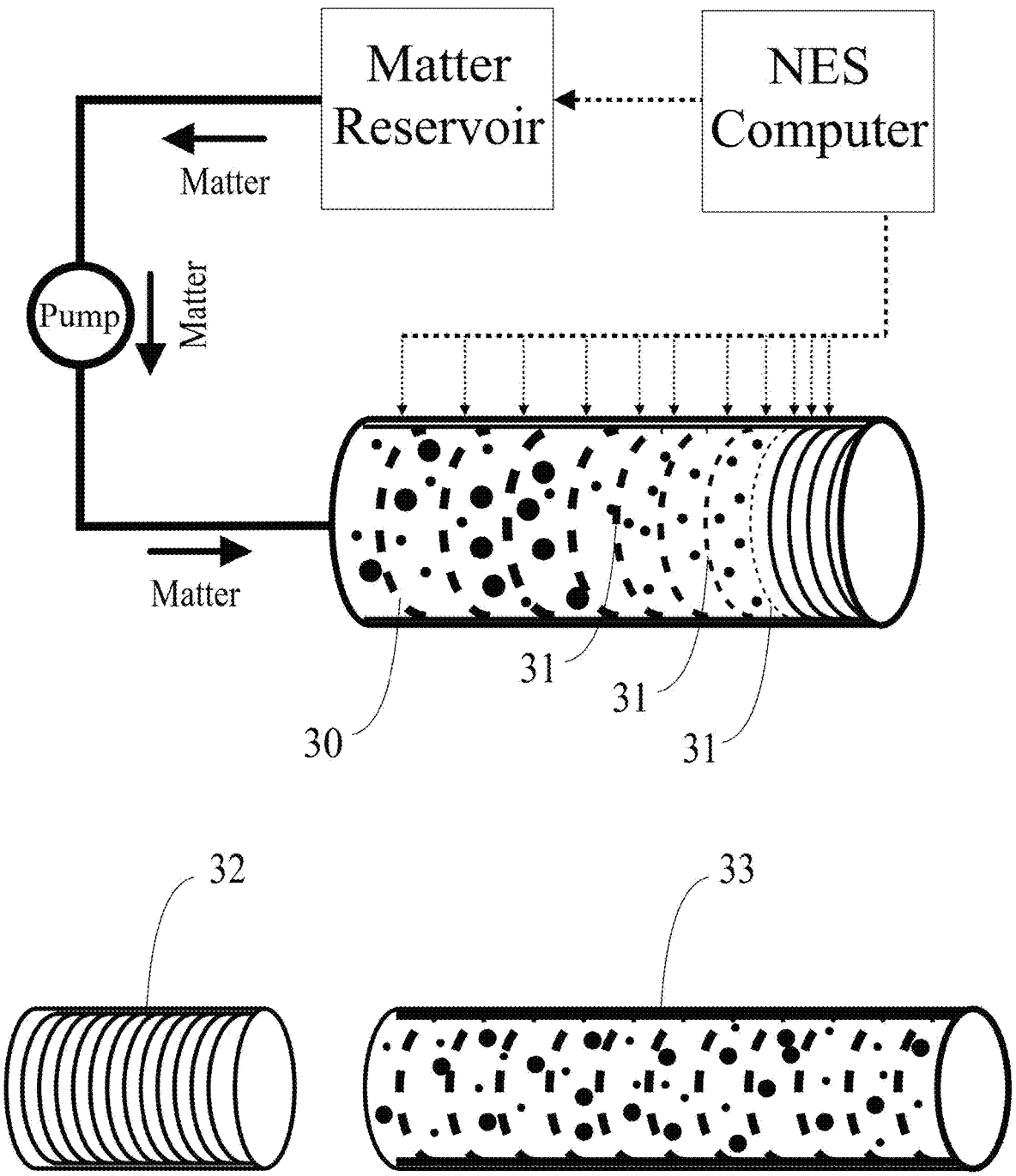
FIG. 18 is a schematic illustration of an embodiment of actuating material that contains cells whose permeability is controlled by a computer.

FIG. 16 depicts an embodiment of an actuating material that is hollow 27, allowing for matter 28 to flow through its inner lumen. FIG. 17 depicts an embodiment of an actuating material that contains a series of cells 29 that can increase or decrease in volume, depending on the amount of matter inside of them. The amount of matter inside a cell is a function of the force requirements. In another embodiment, these cells, as shown in FIG. 18, can change in permeability. This change in permeability can be controlled by the NES computer. The amount of cellular permeability is dependent on the needs of the NES user. One end of the actuating unit allows matter to flow into the first cell 30 while adjacent cellular permeability increases 31 allowing more matter to enter into the cells, thus expanding the actuating material from its initial state 32 when it was not permeable to a state 33 of permeability that allows each cell to expand to their maximum volume. In another embodiment, as shown in FIG. 19, the initial state of the actuating material exists at its maximum volume. A decrease in volume through the removal of matter results in an increase in tension exhibited by the actuating material and an increase in force imparted on an object connected to it 34. For example, when an increase in tension is needed, the permeability of the cells can remain high, allowing for more matter to flow out of the cells, thus decreasing their volume.

Figure 20:
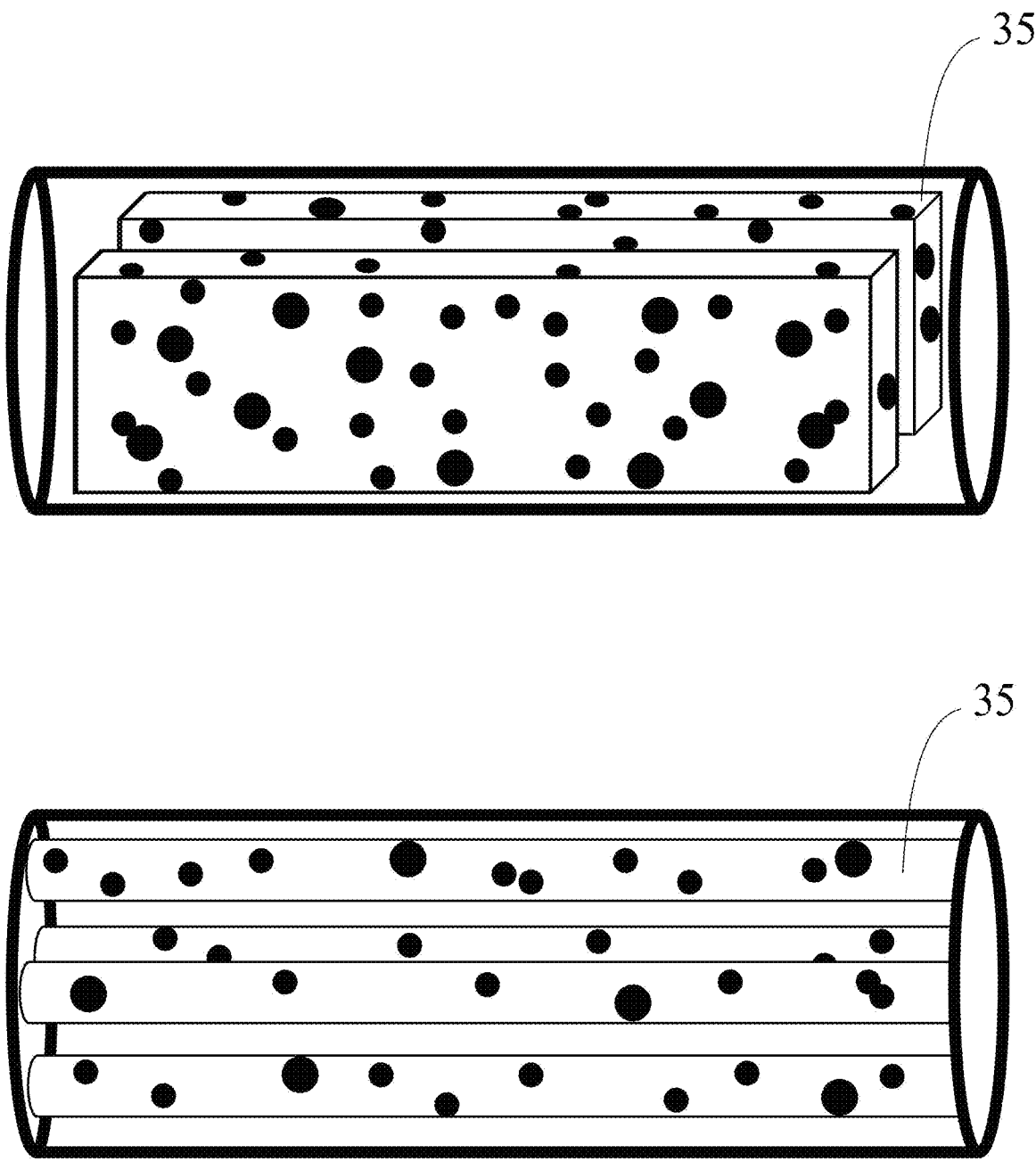
FIG. 20 is a schematic illustration of an embodiment of an actuating material that contains a network of channels for matter to flow.

In another embodiment, an actuating material is impermeable to matter, as shown in FIG. 20, but contains a network of channels 35 that allow matter to flow within the channels. The injection or removal of the matter can be carried out through a system of automatically-controlled pumps, or through a system as simple as a hand pump that can be controlled by the surgeon or an assistant, for example.

Figure 21:
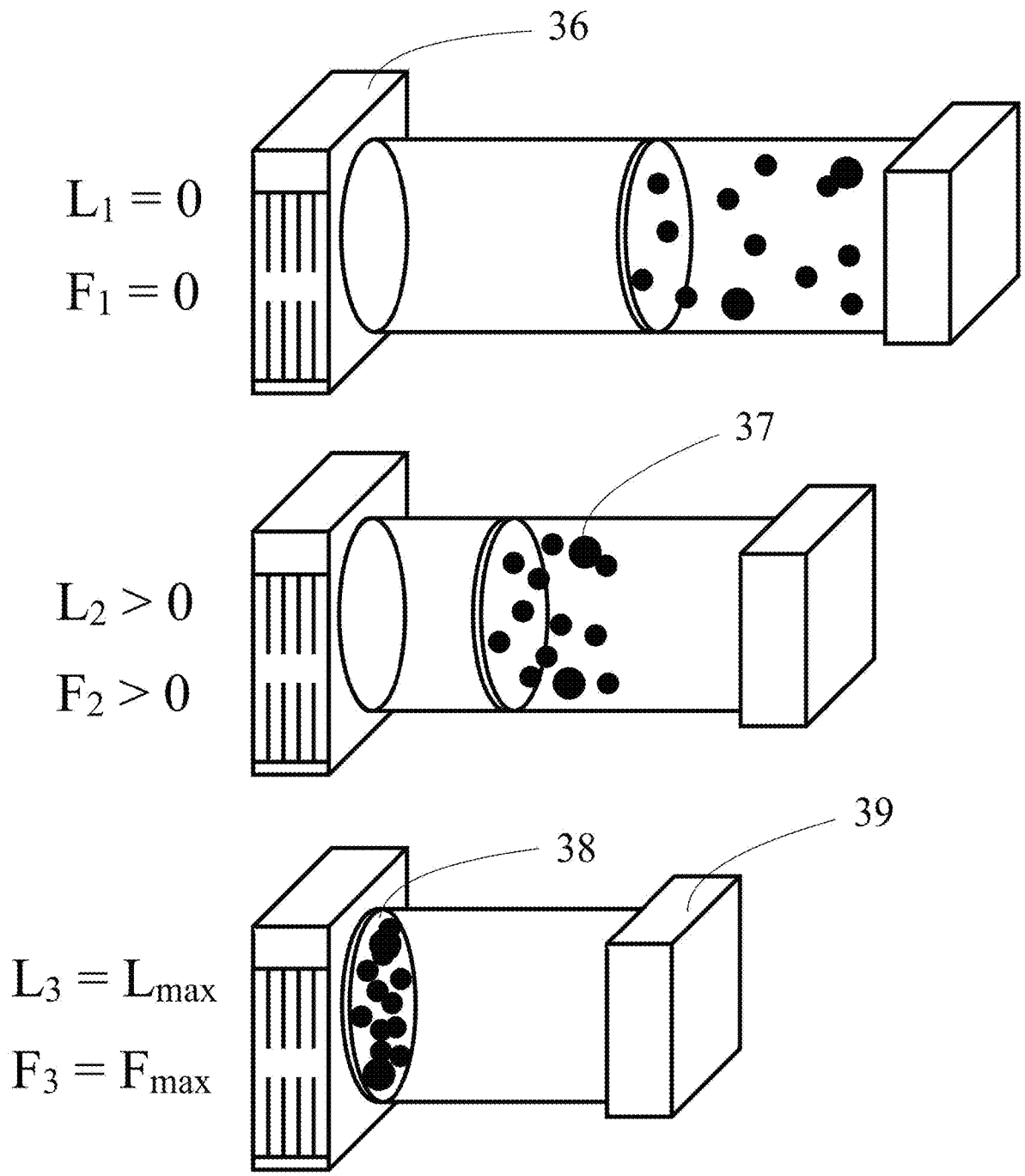

Magnetism: Matter flowing inside an actuating unit can also have properties that are affected by a magnetic field. Magnetically-controlled regions, as shown in the embodiment of FIG. 21, located at the base of an actuating unit 36 create a magnetic field that aligns the fluid 37 to one side of the actuating material in a way that increases or decreases the volume of the actuating material by pushing on a plate 38, fixated to the inner wall of the actuating material, and that separates the two sides of the actuating material. This pushing action on the plate, as the magnetic field increases, moves the other end of the actuating material closer to the magnetically-controlled region and, therefore, increases the tension exhibited by the actuating material 39. Changes in volume and tension exhibited by the actuating material can occur without the need for magnetic fluid, as shown in the embodiment of FIG. 22. The same results can occur in this embodiment when the use of a ferromagnetic material 40 is strategically spaced within the actuating material and is attached to the inner circumference of the actuating material and moves one side of the actuating material closer to the other side of the actuating material. Matter flowing within the lumen or channels of the actuating material can also exhibit chemical reactions that can change the geometric configuration of an actuating material. Varying degrees of pressure from steam, for example, can also cause changes in actuating material's geometry.

II—Controlling Actuating Materials

An NES is considered as the overall apparatus that the user will wear. The term engineered textile material structures, herein, includes the various layers of materials that compose the NES: layers of actuating materials, layers of non-actuating materials, the communication network layer, the layer of embedded sensors, the layer that powers the NES, the combination of any of these layers, and any other layer or material required for the NES to perform as described herein. These layers work together as the neuromuscular enhancement system (NES) and can be fabric-like in its overall composition, it can be fabric-like in its physical characteristics, and it can wrap around the contours of the user's body.

Figure 23:
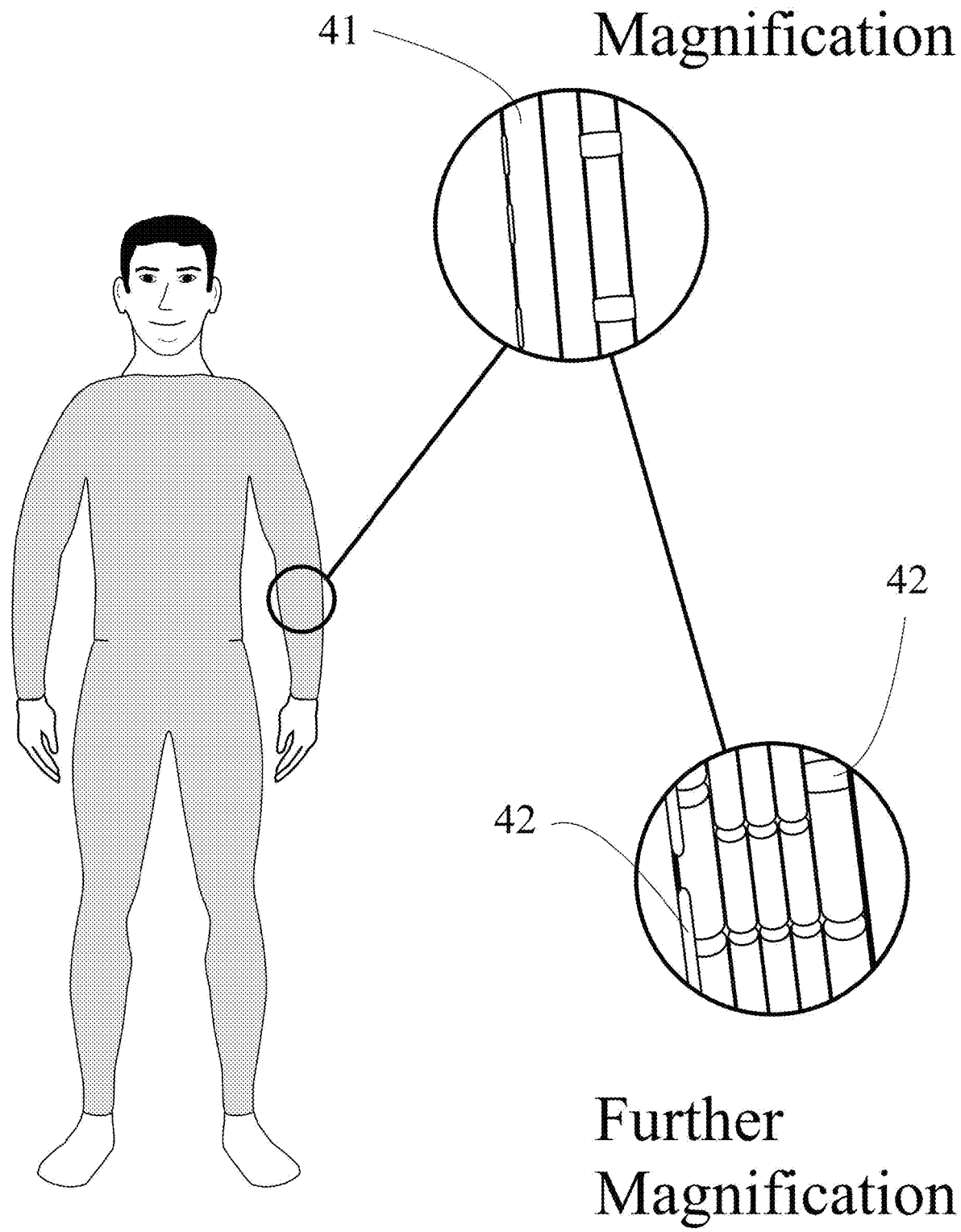
FIGS. 23-24 provide a schematic illustration of sensor technology embedded in the embodiment.

An NES, as shown in FIG. 23, can comprise one or more than one layer of actuating materials 41. The NES can be embedded, for various purposes within these layers, with sensors 42 in none, one, or a multitude of layers of actuating and non-actuating materials. These sensors can assist with the control of actuation of actuating materials or assist the NES in other capacities. For example, motion sensors can be employed to provide information about the position of the entire NES or portions of it. They can also be used to detect the desired motion of the user, and, therefore, assist in affecting outputs of the NES.

Figure 24:
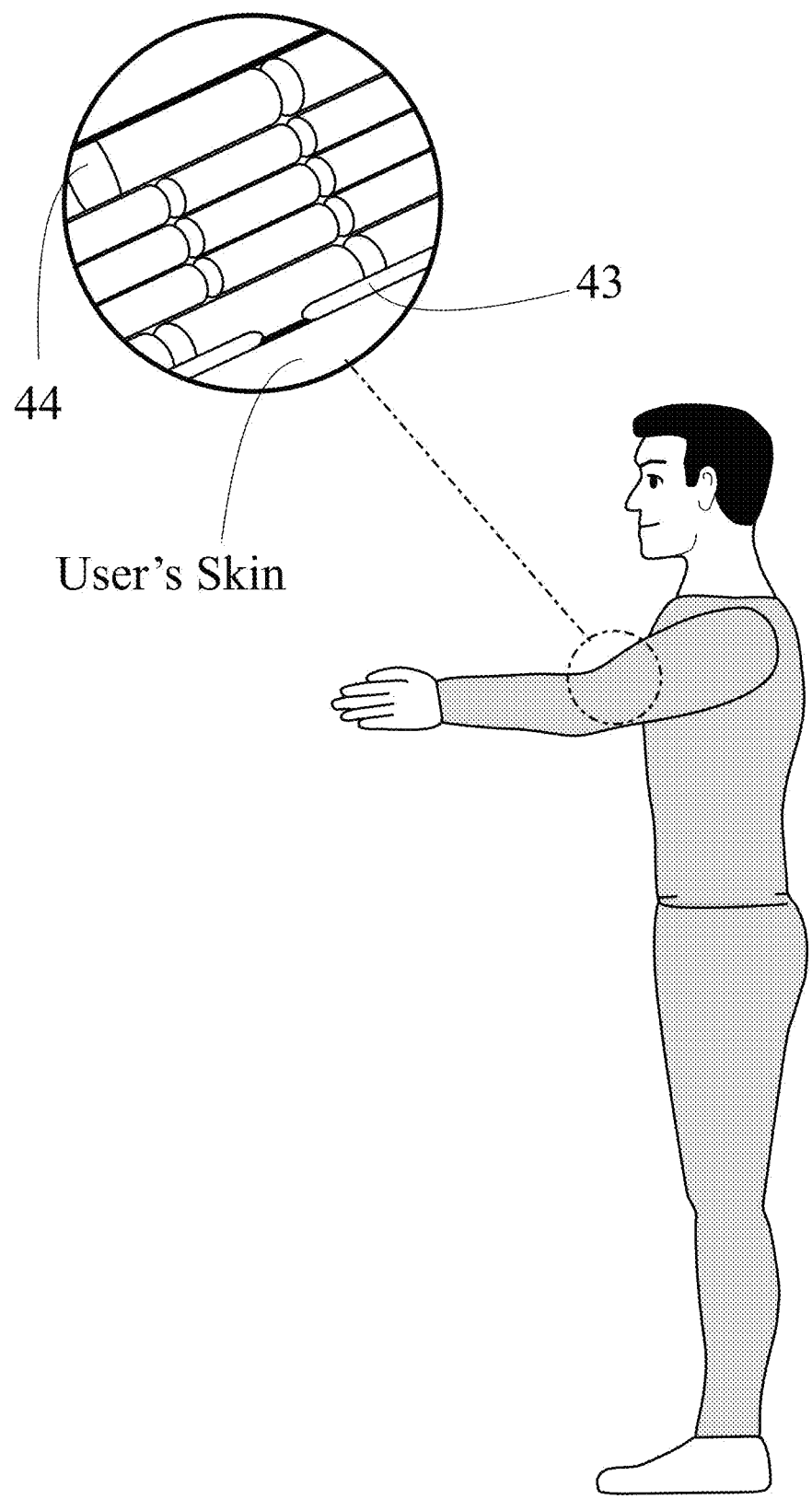

An embodiment of the system with embedded sensors, as depicted in FIG. 24, can utilize the sensors to detect and monitor the muscle activation of the user. These sensors 43 can be in contact with the user's skin to detect muscular activity. Another embodiment of the NES contains sensors that detect and monitor the position and motion of fixed points on the NES. This monitoring can be achieved through the use of inertial sensors 44, GPS sensors, or other types of sensor technology that can detect the position and or motion of fixed points on the NES. A camera monitoring system, residing on the NES, can also be employed to track fixed points on the NES and other objects in relation to the NES in real time. Motion monitoring technology, similar to the type used in movie production or surgical navigation, can also be used with the NES to track fixed points on the NES in real time.

Figure 25:
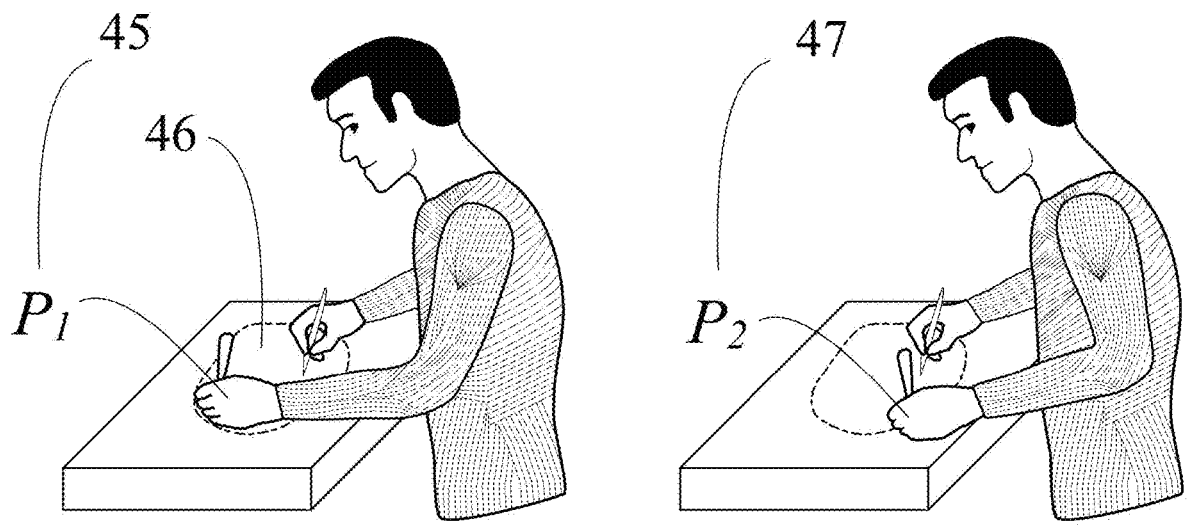
FIG. 25 is a schematic illustration of the embodiment with position technology being used to move a portion of the embodiment.
Figure 26:
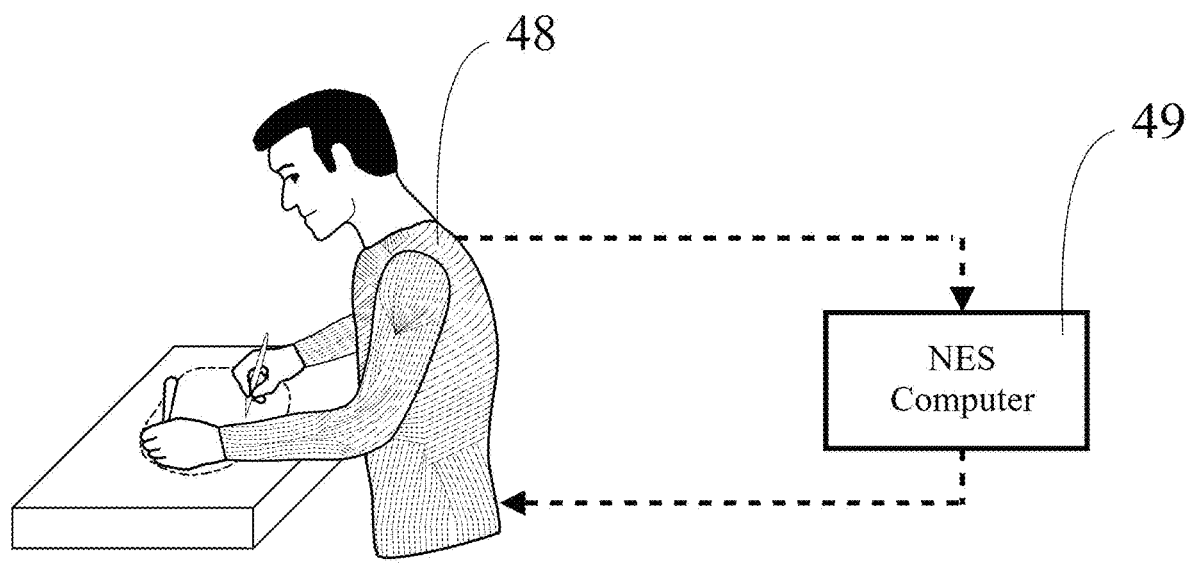
FIG. 26 is a schematic illustration of the embodiment and its computer working in a feedback loop.
Figure 27:
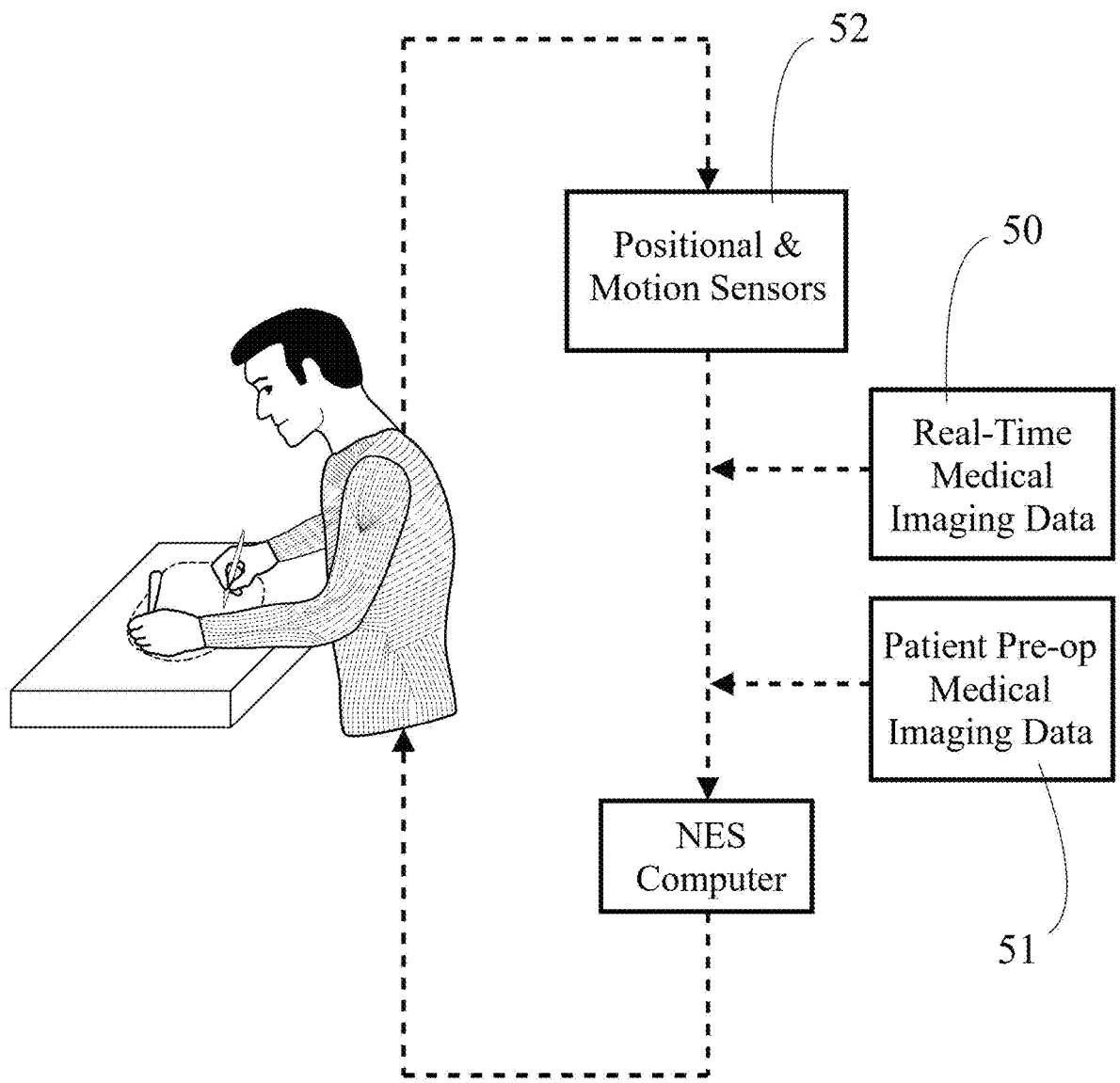
FIG. 27 is a schematic illustration of the embodiment, its computer, and medical imaging technology working in a feedback loop.

One purpose for position and motion monitoring is to provide position guidance and motion assistance to a surgeon during surgery. As shown in FIG. 25, for example, if the surgeon wishes to move his or her left arm from one position, P1 45, within the operative field 46 to another position, P2 47, the motion and position monitoring feature of the system combined with medical imaging technology can be employed with the actuating materials to assist the surgeon with moving his or her arm to a desired position determined prior to the surgery beginning. An example of where this is useful is in spine surgery, where anatomical landmarks of the spine are used as reference points for determining the location of where a screw, for instance, should be inserted into bone for spinal fixation. A feedback loop as shown in FIG. 26 that includes the NES 48 and the NES computer 49, can be employed to assist with the positioning of the surgeon's arms based on preoperative images acquired from the patient. In this depiction, the NES computer gathers position data using the position sensors to make adjustments to the actuating materials within the NES, thus providing continuous and seamless assistance with the surgeon's movements. A more comprehensive feedback loop, as depicted in FIG. 27, contains real-time patient image data captured using medical imaging technology (such as computed tomography (CT), magnetic resonance imaging (MRI), fluoroscopy, x-ray, etc.) 50, and stored information about the patient's anatomy gathered preoperatively from medical imaging technologies 51, and real-time position coordinates of the surgeon's arms in relation to the patient determined by position and motion sensors 52. With this added library of information, the NES computer is able to provide a more complete motion-assistance experience through the activation of the actuating materials while using detailed patient-specific information.

Figure 28:
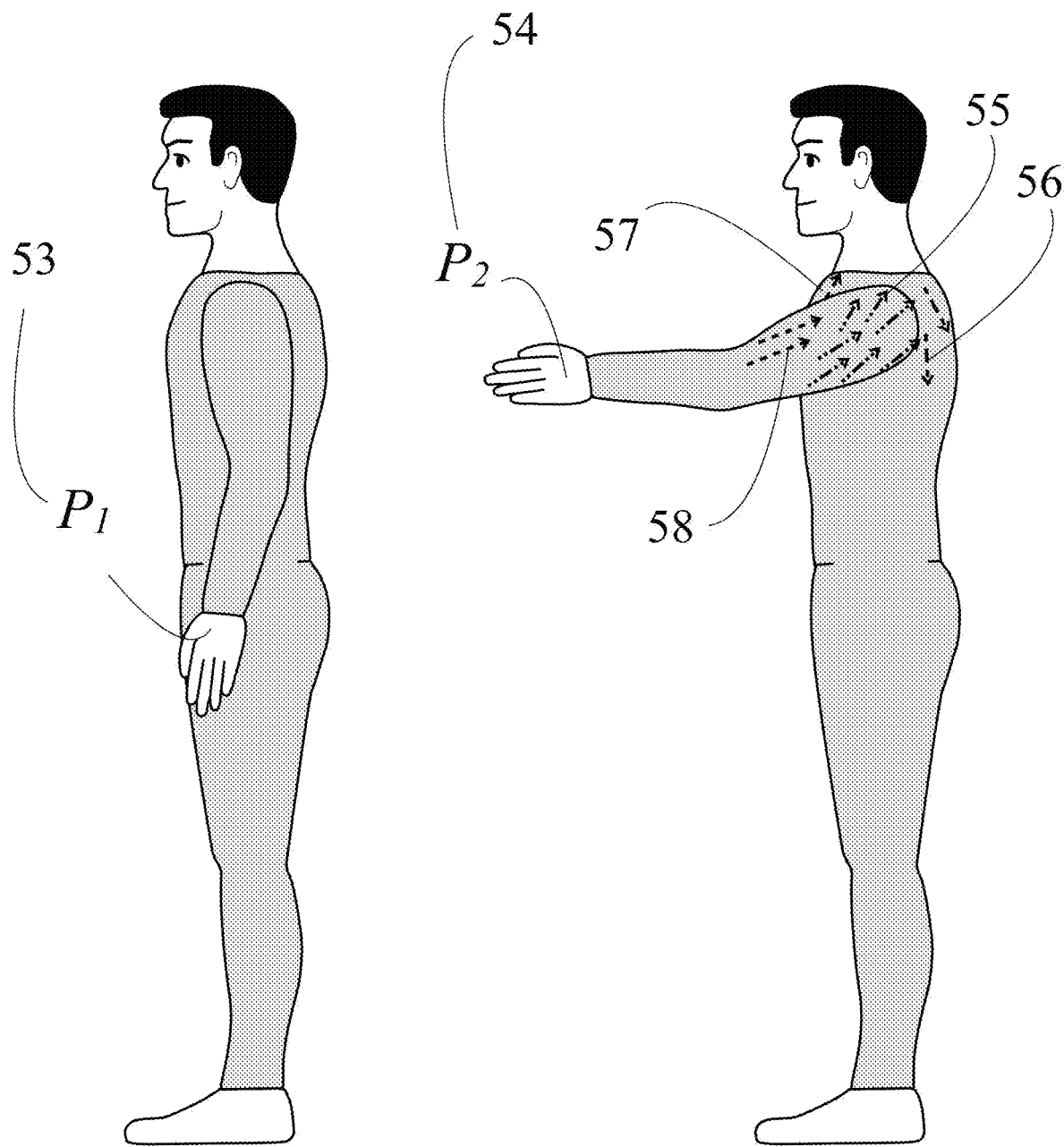
FIG. 28 is a schematic illustration of force contribution from different regions of the embodiment used to raise an arm.

Regions of Actuating Material, Force versus Energy Relationship: An NES can comprise actuating materials that can vary in the amount they actuate based on the amount of actuation needed for a particular region of the system and user. As shown in FIG. 28, for example, the user may wish to move his or her left arm from an initial position, P1 53, and hold it at a new position, P2 54. At the muscular level, a person not wearing an NES would need the contribution of force from the following four major muscle groups to achieve position P2: anterior deltoid, teres major/subscapularis, pectoralis major, and the biceps. The regions of NES material required to assist a user with the motion from P1 to P2 can overlay these same muscle group regions on the user and be named according to the muscle group that they assist to perform a movement or hold a position. The naming system employed for identifying different regions of the NES can follow the same anatomical naming system used for identifying muscle groups or other anatomy in the human body. For example, the NES regions used to assist in the motion depicted in FIG. 28 can be named the following: anterior deltoid 55, teres major/subscapularis 56, pectoralis major 57, and the biceps 58.

The amount of force and energy contribution, as illustrated in FIG. 29, from each of the four NES regions for this movement (anterior deltoid 59, teres major/subscapularis 60, pectoralis major 61, and the biceps 62) can vary throughout the range of motion and can be adjusted by the NES computer to achieve the desired position, P2, as shown in Graph 1. Directly related to the force required to achieve the desired position, P2, is the amount of actuating material actuating for a given region. The amount of actuation needed is also dependent on the amount of force output required by the actuating material to achieve the movement. The amount of energy required to cause this amount of actuation from the actuating material is also dependent on the amount of force needed to be imparted. These relationships are depicted in Graph 2.

Sensor Technologies

A number of sensors are used with the NES for a variety of reasons. Sensors that exist within the feedback loop of the NES and the NES computer are used to work in conjunction with the NES and the NES computer to actuate the actuation materials to assist the user with a task. Sensors are also employed to monitor the vitals of the user and to maintain the comfort level of the user. Various types of sensor technologies that are employed to enhance the NES are discussed here.

Haptic Sensors: Sensors embedded within the NES are used as part of a feedback loop to provide haptic information to the user about the surrounding physical environment. This feedback technology can improve the ability of the NES and the user to interact with the user's surroundings. In the case where the user is a surgeon, he or she is in essence the robotic system, and is able to perform surgery within the operative field with the same haptic interaction that the user would have if the user were performing surgery without the NES. By wearing the light weight and unencumbered NES, the surgeon will not have limitations in being able to work within the operative field and interact seamlessly with his or her environment.

Position Sensors: Position sensors can be embedded within an NES to provide real-time information about the location of any area of the NES in real-time. With this information the velocity and acceleration of an area of the NES can also be determined. This positional data can be collected by the NES computer and can be used for a variety of reasons.

Figure 30:
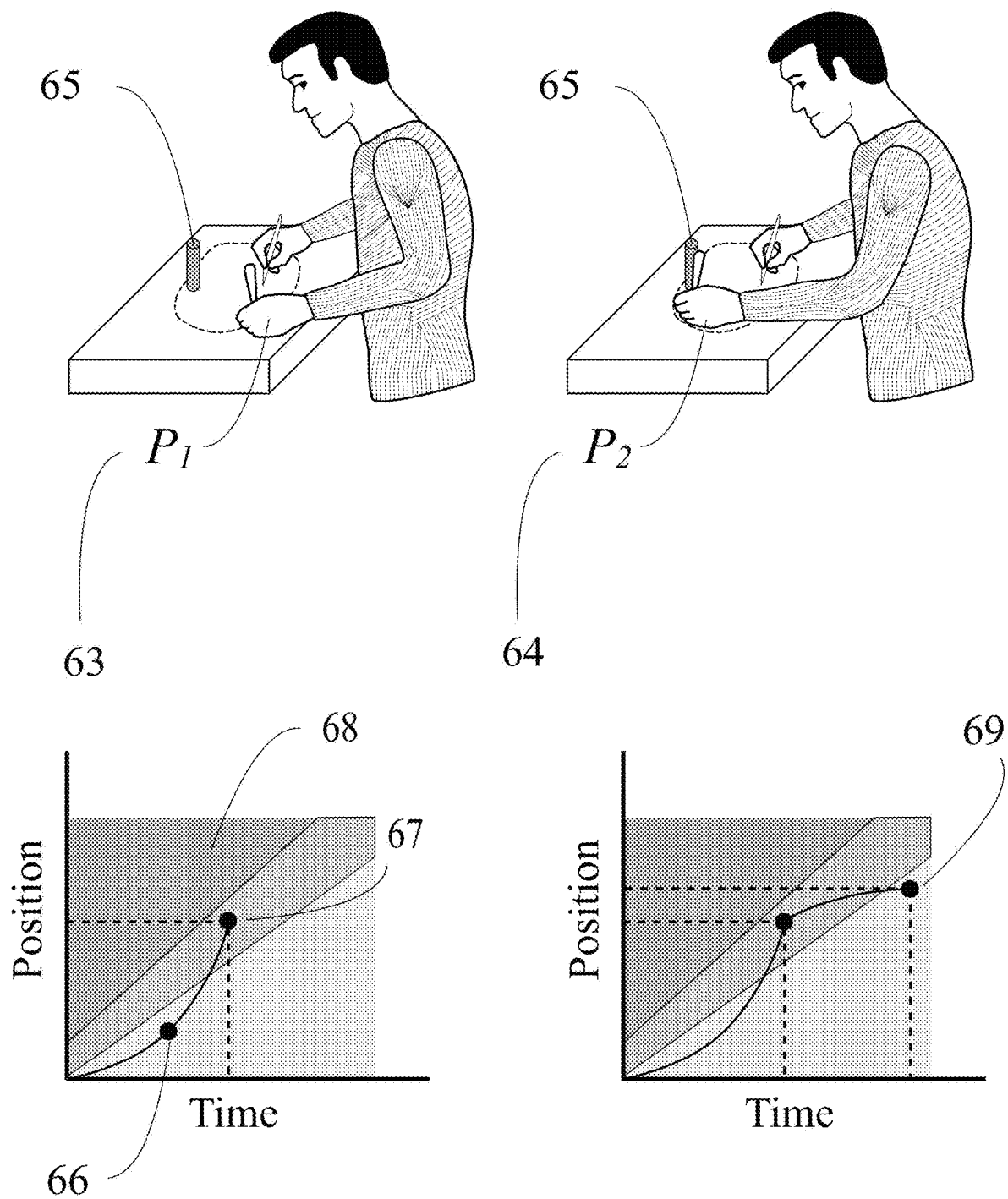
FIG. 30 provides a schematic illustration of safety measures employed by the embodiment.

The data collected from position sensors can be used to ensure the safety of the user and of others who are near the user. Positional data, along with medical imaging data of the patient (x-ray, CT scan, MRI, etc.), can allow the computer system to determine the relative location of the NES in relation to the patient or other objects. For example, as shown in FIG. 30, if a surgeon wearing the NES moves his or her left arm from position P1 63 to position P2 64 and the speed at which the user moves his or her arm toward an important anatomical structure 65 identified by the user, with or without the use of medical imaging, is at a speed that is recognized by the computer to be safe 66 but drifts toward a speed 67 that might approach a dangerous speed 68, then a correction algorithm in the computer system is initiated to change actuating material properties in the appropriate regions of the NES on or near the left arm to decrease the speed of the arm to a speed that is safe 69 or that stops the movement of the arm altogether. The same safety feature can be provided to monitor acceleration, or any other measurable characteristic, using position sensors or any other type of sensor technology.

Sensors Used for Safety Measures: In addition to the actions just mentioned that are employed by the NES computer to provide safety, the NES computer can also provide audible, visual, and haptic notifications to the user about the speed and position of areas of the NES in relation to the patient. For example, the NES computer can notify the user through an audible or visual cue that the speed or acceleration of the user/NES is about to exceed a safety threshold. A visual warning can be provided through a light signal or an audible warning through a speaker, or a combination of all these indicators can be provided. Feedback notifications can also take the form of an action or actions initiated by the NES computer and carried out by the actuating materials of the NES. This feedback can be a force provided by actuating materials and initiated by the NES computer that gently opposes the direction of motion of the user or squeezes the user's arm as in the example illustrated in FIG. 30. It can also provide feedback in the form of a vibration in certain regions of the NES that are exceeding a safety threshold.

Data from the position sensors can be compiled by the computer system and processed by the NES computer with stored patient data and or real-time patient data. With this library of information, consisting of position information and patient information, the user and NES can move based on the feedback loop in which they and all the subsystems reside. The NES would be able to make the appropriate adjustments in position and velocity that best meet the surgical requirements, all while maintaining safety and preserving the energy of the surgeon.

With real-time data about the position of the NES in relation to its environment and with preoperative data about the patient, the NES computer can calculate that an increase in speed or acceleration is within safe bounds. It can then signal for changes in actuating material that increase the speed of regions of the NES required to complete a certain task. In this situation, the time required to complete the surgery is reduced by optimizing the rate at which tasks are performed.

Electrical Myography Sensors: Skeletal muscles operate in antagonistic pairs. In a muscle pair system, when one muscle contracts the other relaxes. The quadriceps and hamstrings, for example, are the two main muscle groups in the thigh of the leg that work together for a person to walk by relaxing and contracting at the appropriate time: when the quadricep flexes and the hamstring relaxes, the leg flexes and moves forward. Electrical myography (EMG) sensors are sensors that detect the relaxation or tension in muscle fibers by detecting action potentials of skeletal muscle cells. An NES can use signals generated by muscles and detected by EMG sensors as part of a feedback loop that can direct specific actuating materials to activate when a particular motion, or assistance with a particular motion, is required.

Figure 31:
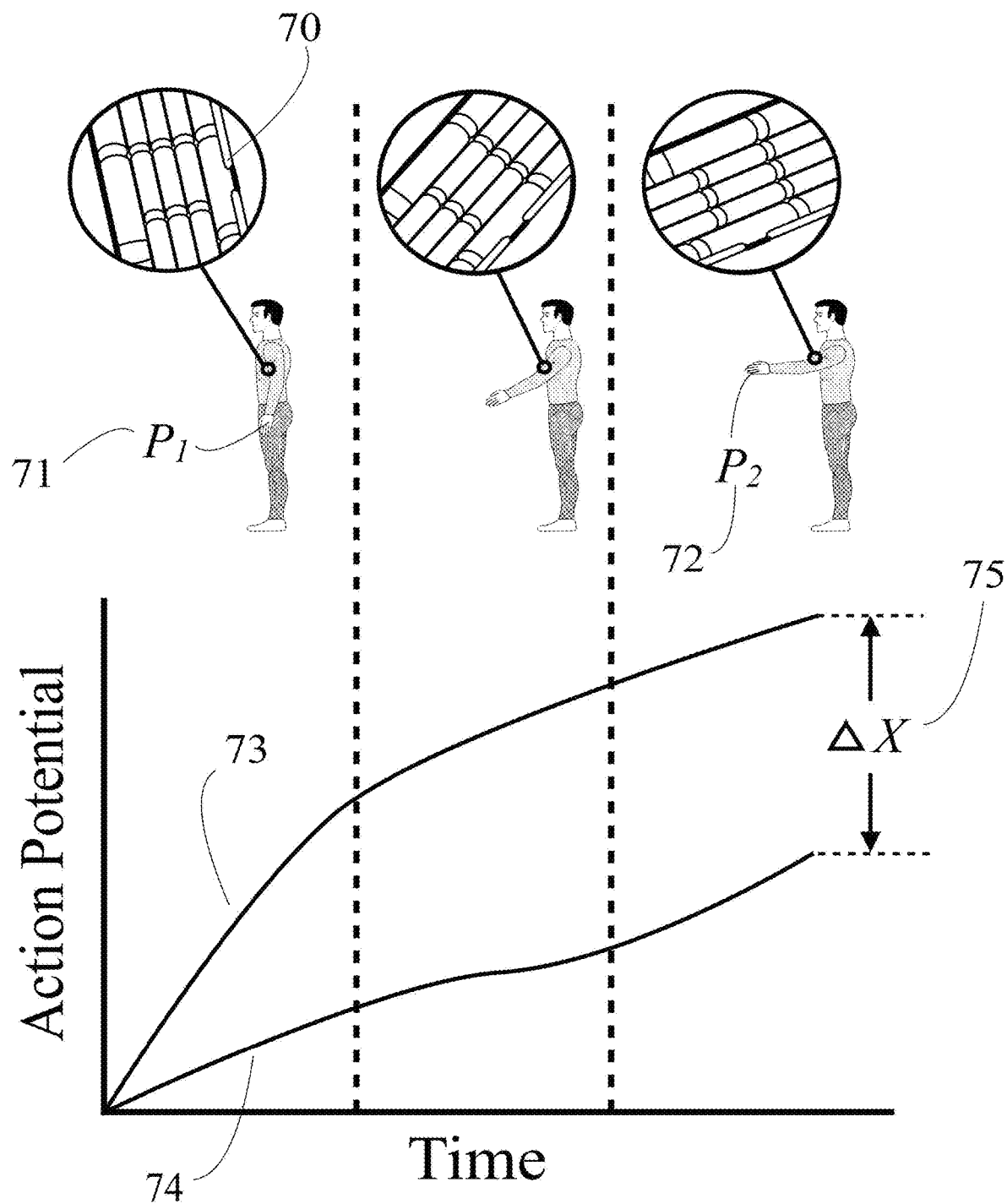
FIGS. 31-33 provide schematic illustrations of example embodiments in use with sensor technology.

The NES layer most proximal to the user's skin, as shown in FIG. 31, can be embedded with EMG sensors to detect skeletal muscular activity. These sensors can operate in a feedback loop that controls the NES. As an example, sensors embedded within the layer of the NES proximal to the surface of the left arm muscles and surrounding muscles 70 can detect muscle activity. If the user raises his or her left forearm from position P1 71, to another position P2 72, the EMG sensors lined across these muscles can detect a positive action potential indicating that the user is activating his or her muscles used to lift the left arm. The NES computer, through the signals received from the EMG sensors, can interpret action potential activity of these muscles and infer that the user wishes to move his or her arm to a new position. Through the instantaneous feedback loop of the NES, the computer can indicate to actuating materials in these muscle groups that the actuating materials from these areas are needed to assist in this movement. The actuating materials from these areas can create the actuation necessary to assist in the motion and, therefore, reduce the amount of energy the user needs to exert in order to move to the desired position. The difference in the amount of energy the user would exert if he or she were not using the NES 73, compared to if the user were using the NES 74, is represented by delta x 75. The amount of actuation needed in this situation can be set as a percentage of the amount of work required to complete the task. This percentage can be adjusted by the user. For example, if the user wishes to have the NES assist with 25% of the work required, the user can carry out the work using 75% of his or her own muscular activity and the NES can compensate for the remaining 25% that is needed to complete the work. The amount of assistance desired by the user from the NES can also be programmed to an automatic level. With a greater percentage of assistance provided by the NES, a lower percentage of muscle fiber recruitment from the user's body is necessary and, therefore, less physical exertion is required by the user.

EMG sensors used on the NES can be surface-contact type sensors that require only contact with the surface of the skin, or they can be minimally-invasive type sensors that detect action potentials with tiny electrodes that penetrate the skin, such as microneedles.

Figure 32:
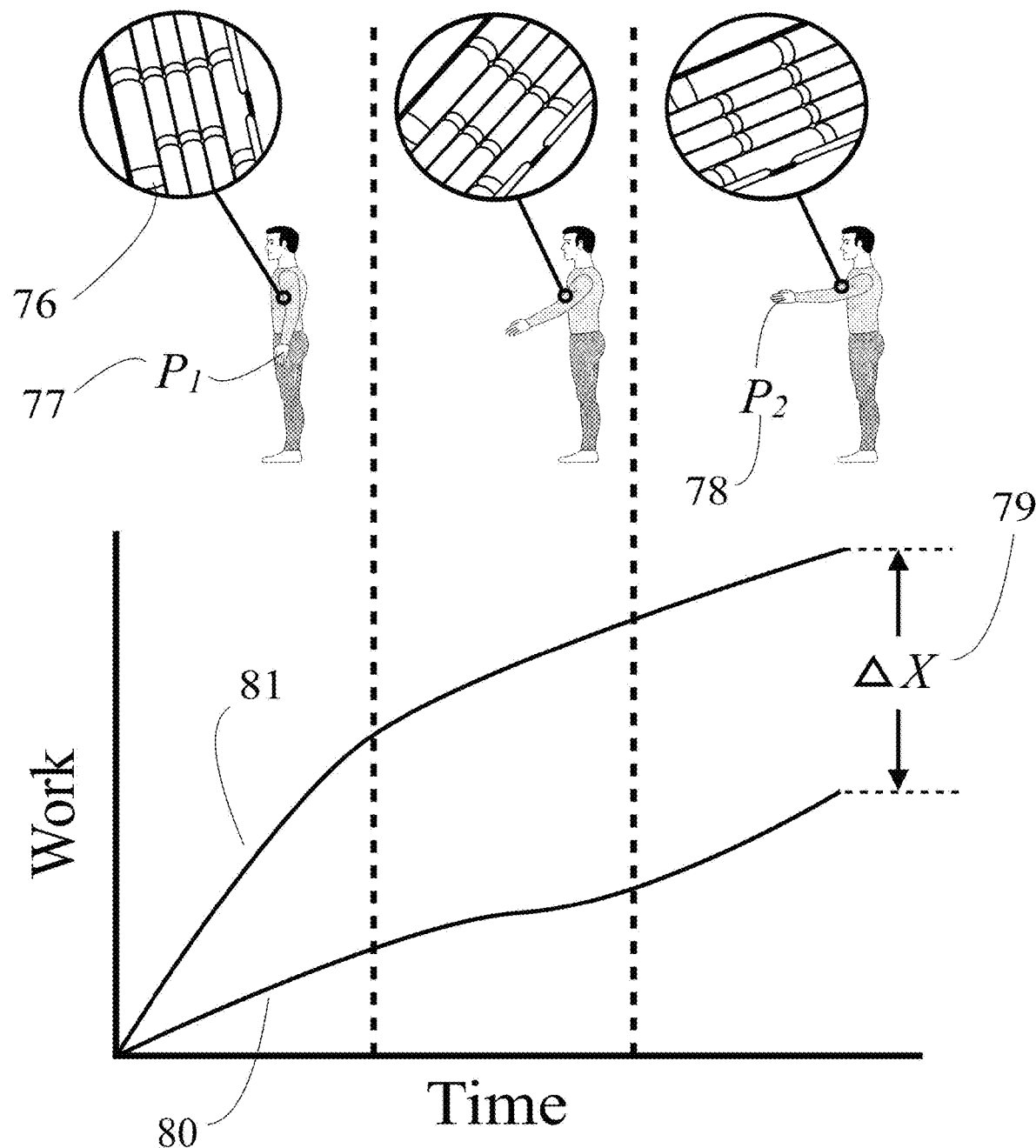

Position Sensors: As shown in FIG. 32, position sensors 76 can provide the same feedback information required to move the left arm from position P1 77 to position P2 78 (similar to the depiction of energy preservation in FIG. 31 with EMG sensors), and can provide the same user-energy-saving advantages 79 by wearing an NES 80 compared to not wearing an NES 81.

Other Types of Position Sensors: Position technology such as Global Positioning Systems or motion capture systems can be used to track the position of the NES. With a motion capture system, or performance capture system used for tracking finer movements, a set of cameras residing near the NES are used to capture the position of markers on the NES. GPS technology can be integrated into the NES or both GPS and motion-tracking technology can be used to track the NES.

Figure 33:
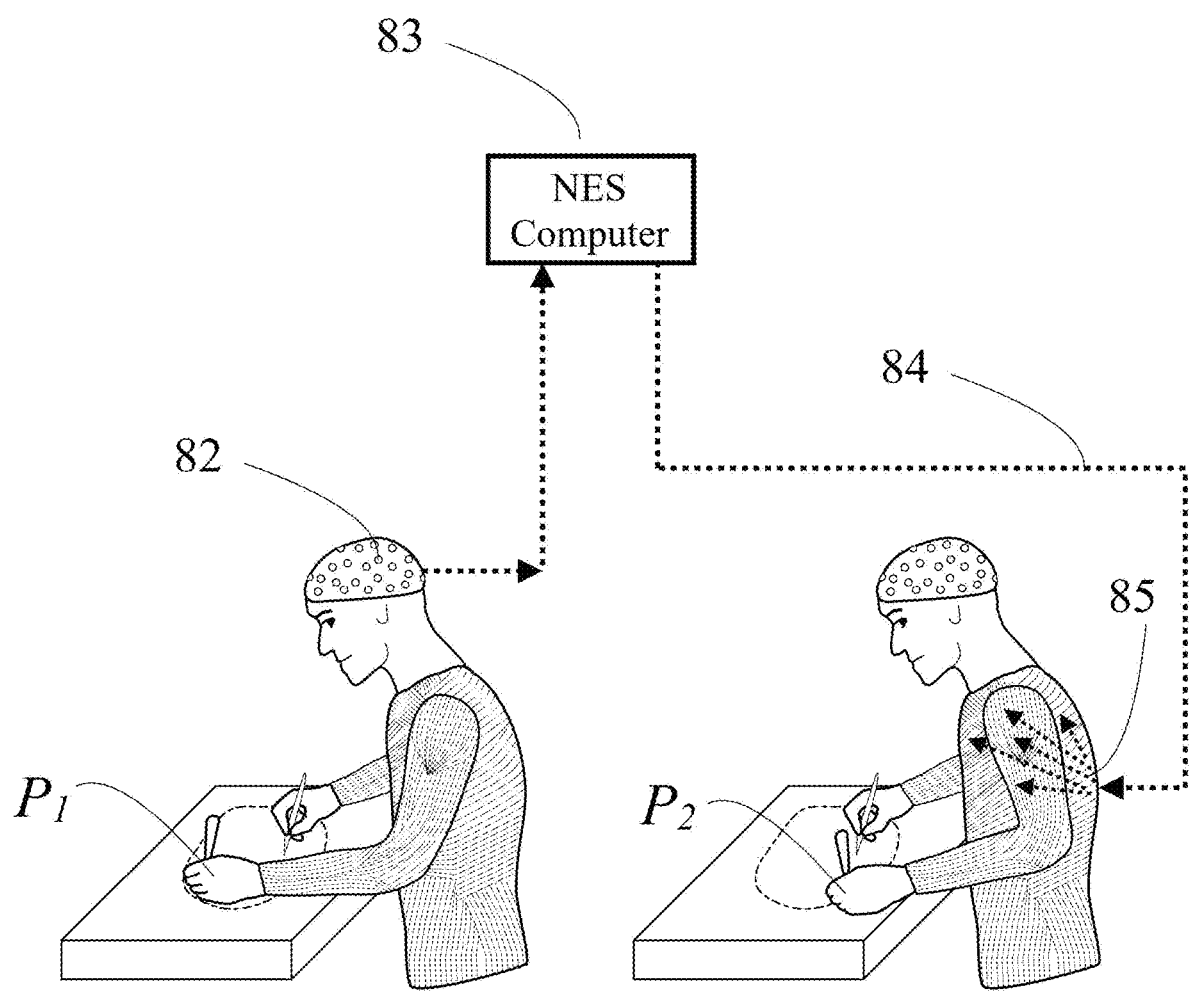

Electroencephalography Sensors: Electroencephalography (EEG) sensors can also be used as part of the control feedback loop of the NES, as shown in FIG. 33. EEG sensor technology is currently being used in exoskeleton research and prosthetic rehabilitation therapy for motion control. These sensors can be worn on the user's head 82 to detect brain waves. In an embodiment of the NES that uses EEG sensors, brain wave signals detected by the EEG sensors are sent to the NES computer 83 where the signals are analyzed and processed. The computer calculates the desired motion output of the user and determines which actuating materials are necessary to be recruited in the NES in order to assist with the motion. The computer then sends a signal back to the NES 84. The NES then sends signals to the regions of actuating materials that are required for assistance to complete the task. The signals arrive at the designated actuating material regions and initiate the actuation of the actuating materials 85.

Sensors Used for User Vitals and User Comfort: Additional sensors can be embedded into the NES to detect the vital signs of the user. For example, sensors that detect pulse rate, temperature, respiratory rate, and blood pressure can be used so that the user is aware of his or her own well-being.

III—Characteristics of the NES Fabric

Figure 34:
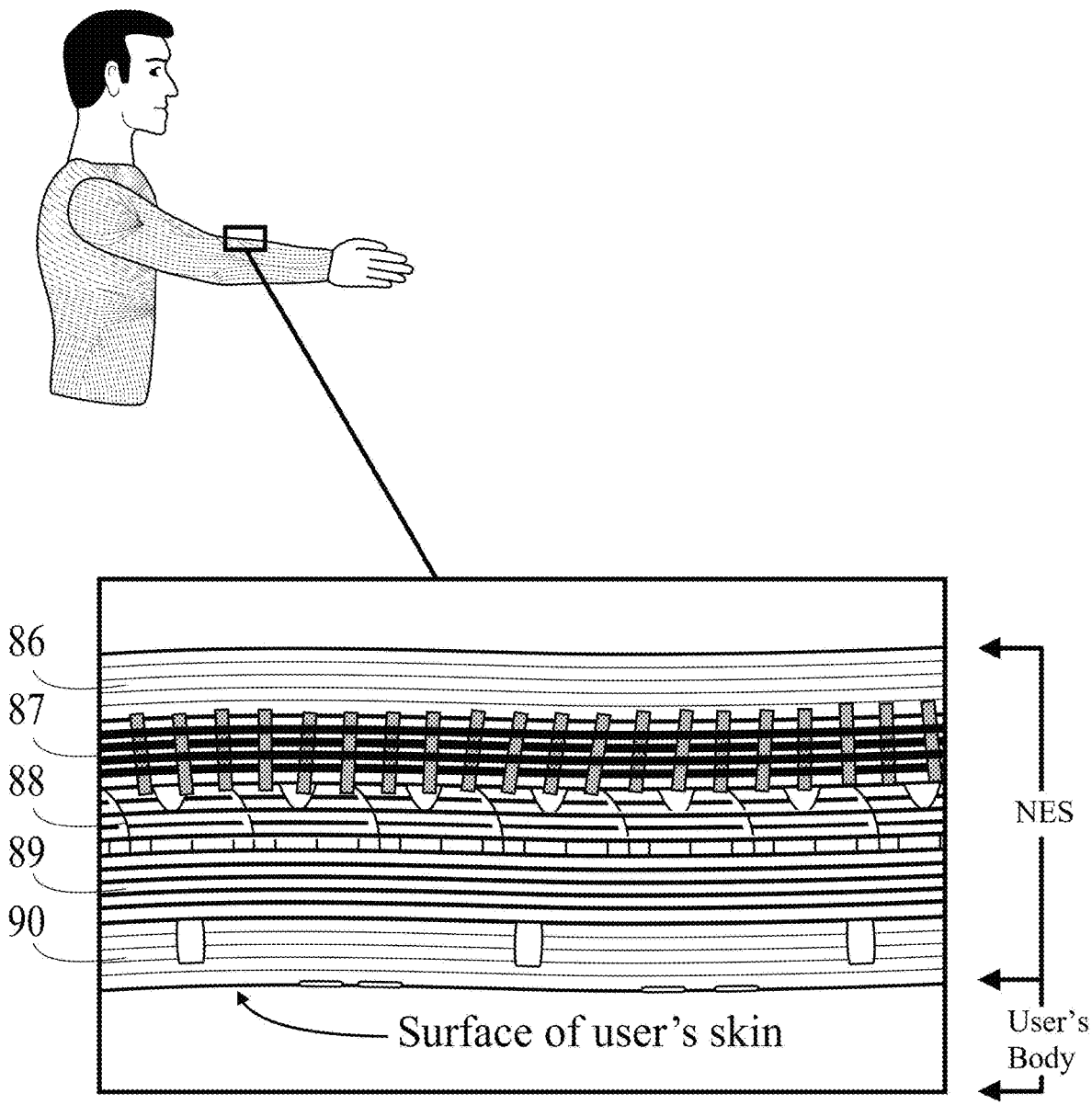
FIGS. 34-37 provide schematic illustrations of various embodiments of layers of the embodiment.
Figure 35:
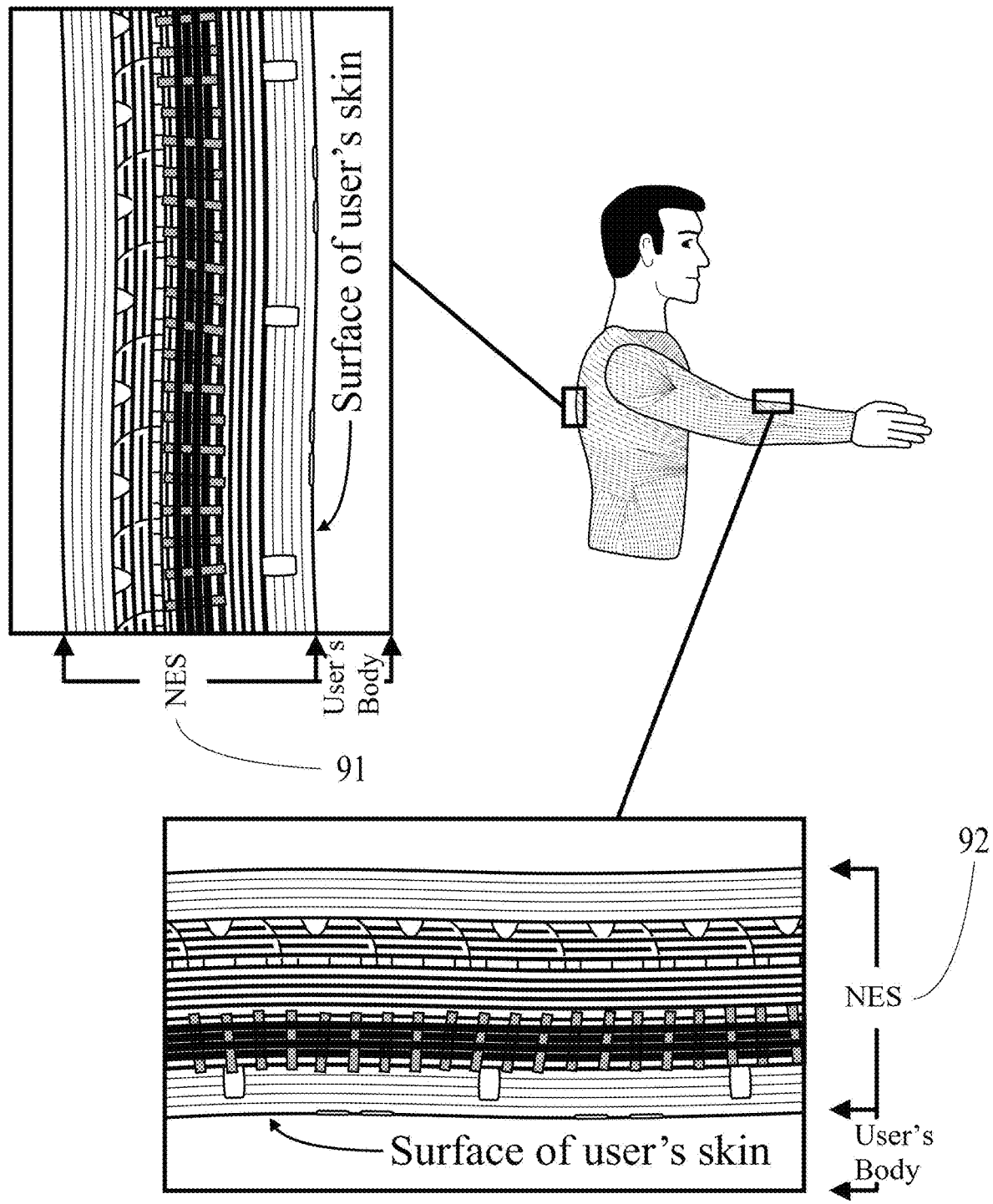

Contourability: An NES can comprise one or more than one of the following layers, as shown in FIG. 34: a layer of actuating material 86, a layer of non-actuating material 87, an electrical communication network layer 88, a layer that powers the NES 89, a layer of embedded sensors 90. The order in which these layers lie, with respect to the user's body, can be consistent throughout the said layers and through the entirety of the NES or it can branch off into different sections at different areas of the NES. As shown in FIG. 35, for example, the upper back region can be comprised of materials in the following order, starting with the layer most proximal to the user's skin 91: embedded sensors, power layer, non-actuating material, electrical communication, actuating material. The order of layers of materials, starting with the most proximal layer to the user's skin in the right forearm section of the NES can be 92: embedded sensors, non-actuating material, a layer that supplies power, electrical communication network layer, actuating material, or they can reside in an order not listed here.

Figure 36:
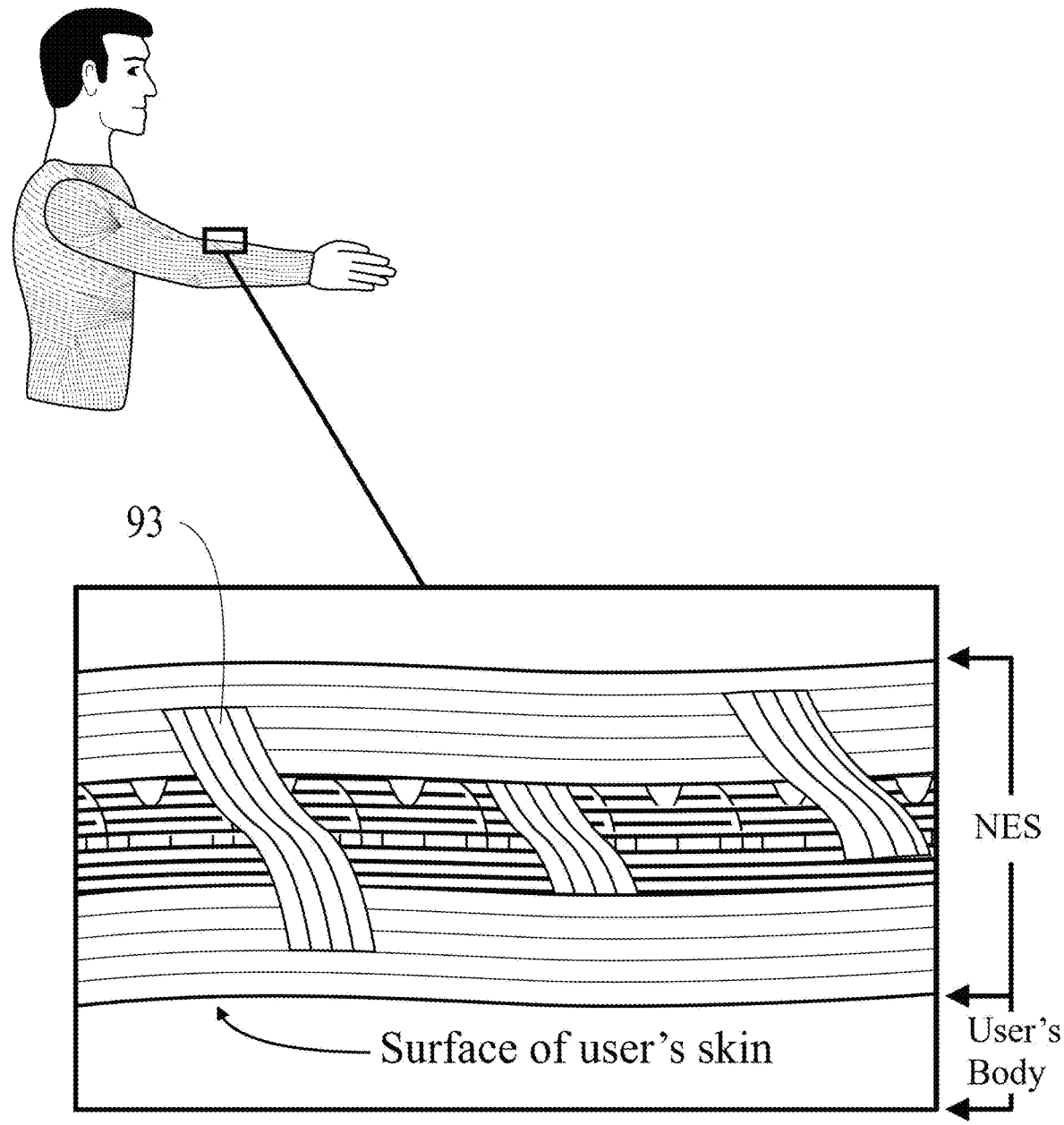
Figure 37:
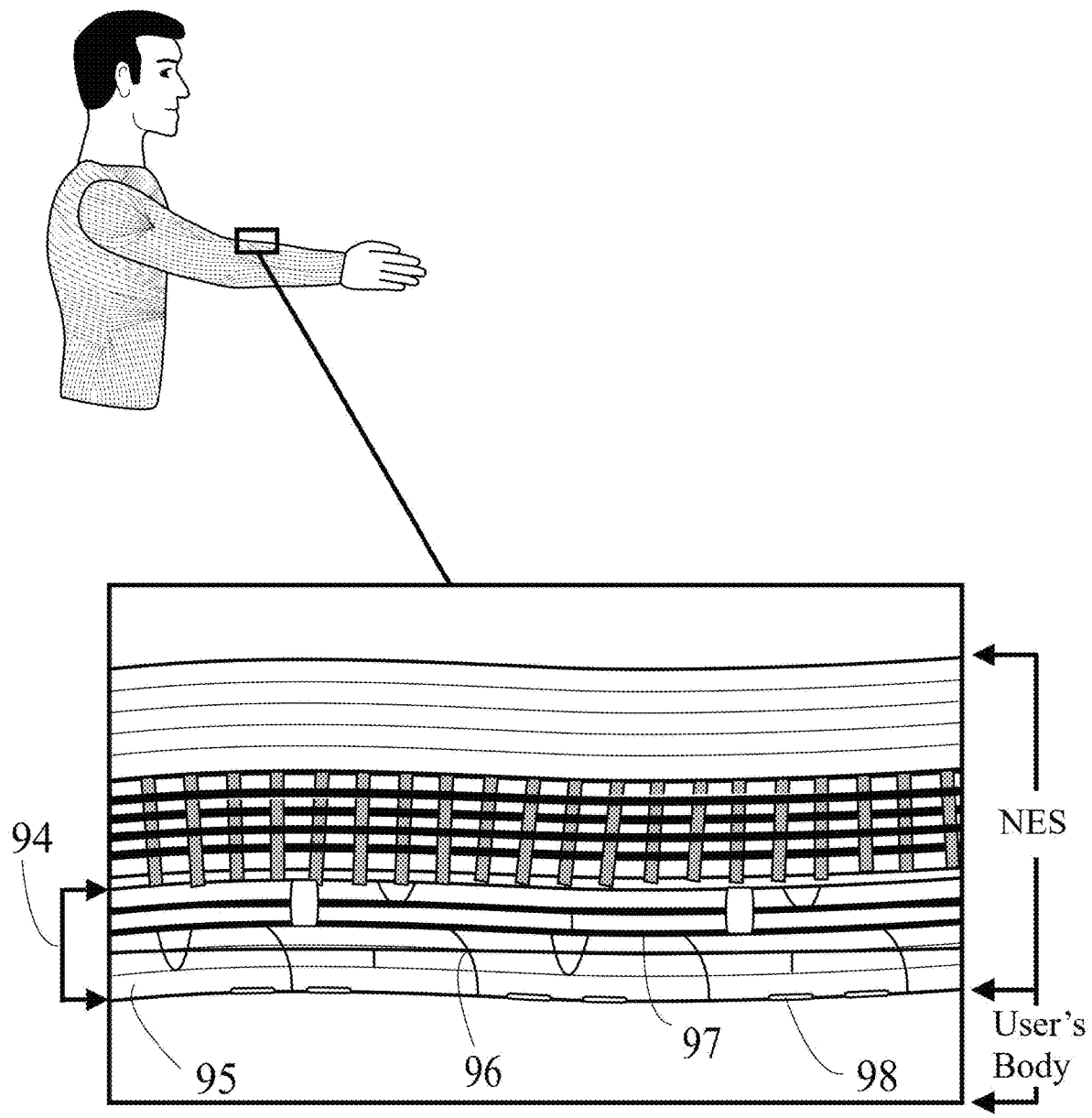

A layer can be distinct throughout its entirety or, as shown in FIG. 36, it can cross one or more than one of the adjacent layers 93. In other words, each layer is not restricted to one single type of layer material. For example, as shown in FIG. 37, one layer can possess properties of the following layer types 94: actuating properties 95, communication layer properties 96, power network layer properties 97, sensor layer properties 98.

System Snugness for NES Function: The NES has an inherent amount of tightness. As shown in FIG. 38, one layer of actuating materials can be used to provide additional tightness to the way the NES fits the user's body. The inherent tightness of the NES and the tightness provided by the actuating materials will be referred to herein as snugness.

When activated, the layer proximal to the surface of the user's body 99 tightens and moves the adjacent layers closer to the user's body as indicated by delta X. As this proximal layer tightens the adjacent layers also tighten. The degree to which the adjacent layers tighten can be controlled in a passive way, meaning that its tightening occurs by the tightening of the proximal layer since it is connected to the proximal layer and any change to the proximal layer will cause changes in the adjacent layers. The tightening of each layer can also be directly controlled by the NES computer. The actuating material within this layer can be oriented in a pattern that is approximately longitudinal to the long axis of a body part, for example, an arm as shown in FIG. 38. Or it can be oriented in other fashions according to the desired characteristics in use. This layer of actuating materials 99, when activated, tightens around the circumference of the arm 100 to pull layers of the NES that lay distal to the surface 101 of the arm closer to it. This feature of the NES provides for a snugger fit to the user's body in a similar way that a swimmer's wetsuit fits snugly on the user's body. The degree to which this layer exhibits snugness can be controlled by the user of the NES, or it can be controlled by the NES computer, or both. The NES computer can adjust the degree of snugness required for particular tasks or other situations that require changes in snugness. As shown in the embodiment of FIG. 39, a layer of actuating materials most distal to the surface of the arm is activated to provide more snugness 102, in addition to the snugness being provided by the layer most proximal to the arm 103. The amount of snugness can vary at different regions on the NES, as well.

The amount of snugness, in regions of the NES whose snugness is being controlled by the NES computer or by the user, can be recalled by the NES computer from the user's previous tasks. The user can indicate that the amount of snugness be repeated for future tasks. The NES computer can also offer suggestions on the amount of snugness, which the user can accept, reject, or modify for a particular task or duration of time.

Figure 40:
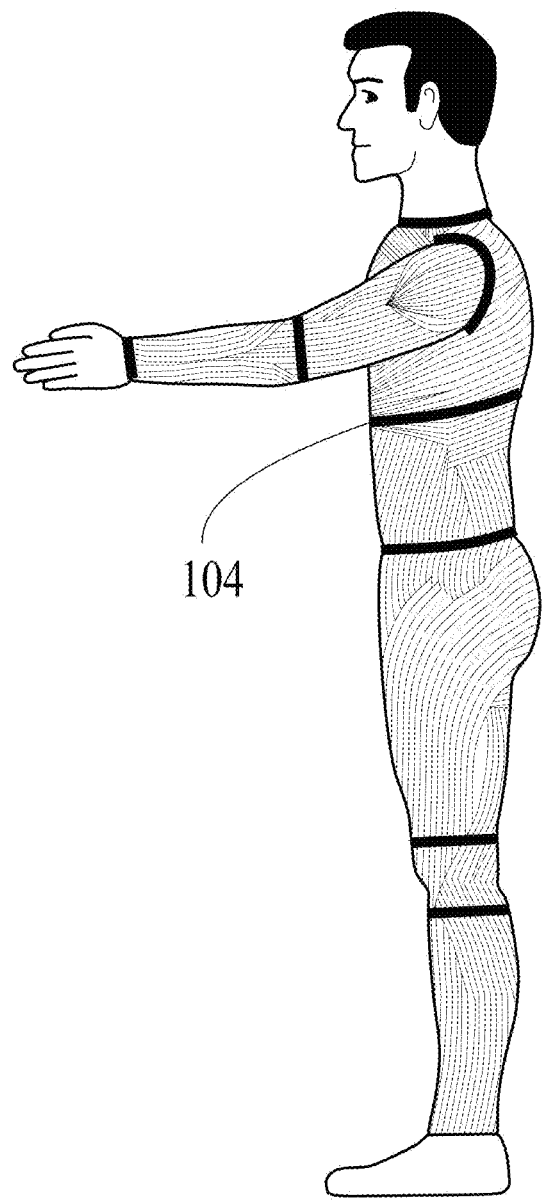

The layer of actuating materials providing for snugness can exist across the entire surface of the NES or in strategic areas only, depending on where they are most likely to be useful. Instead of the layer extending across the whole surface of the user's body or in strategic areas, the layer can exist as a band of actuating material at certain points on the user's body and cross the other layers of the NES. FIG. 40 depicts a band of actuating material that crosses the other layers and provides snugness. It can serve as an anchor point 104 or a fulcrum point for the actuating material layer to connect to and impart forces. This band of actuating material can provide a structure that is anchored to the body for the actuating materials to pull on when they are activated and provide the forces needed for support or for motion assistance. Other fabric layer types can also attach to this band of actuating material. Sensors of any type can be embedded within any of the embodiments of actuating material described here that provide for snugness. The band of actuating material can also provide resistance to the sliding of the NES if actuating materials or other objects are pulling on it. The same is true for material that provides snugness and is nota band.

System Snugness for User Comfort: To maintain maximum comfort, the degree of snugness of the NES can be adjusted to provide comfort to the user. For example, if the user knows he or she will not use the lower section of the NES for a long duration, because he or she will be sitting, then the user can adjust the snugness of the lower section of the NES to fit looser than the torso section of the NES where most of the work will be performed. The degree of snugness can be variable and can be controlled by the NES computer automatically. The user can also make these adjustments through a user input device such as a mouse or a touch-screen, or through audible commands understood by the NES computer, or by other input facilities known in the art.

The NES also has the ability to recall certain snugness comfort level conditions under which a user has determined that he or she works best. The NES can self-adjust to these comfort levels at different times during the surgical procedure. Adjustments to posture or position of the user's limbs can also be made automatically by the NES in a controlled and safe manner. These adjustments can be made to maintain comfort, to increase the circulation of the user, or to create micro movements in parts of the user's body that have not moved in a while but need to move so as not to allow one part of the body to become too sedentary, which can lead to paresthesia and or blood clot formation.

The NES can also provide a feature that cycles the amount of snugness of the NES throughout various areas of the user's body. A focus can be made on areas that are not moving for a long duration of time, such as any area of the body that does not contribute directly to a given task. This feature can provide for increased circulation to these areas of the body. The degree of snugness can cycle in waves, vibrate across a part of the body, or propagate through some other action not described here, again, to prevent paresthesia and or prevent blood clot formation.

System Compatibility with the Ambient Environment: The NES is composed of materials that are biocompatible. This can be important due to the surface contact with the user and the probable contact with a patient and with other individuals.

The NES is compatible with the operating room and operating room equipment in that it does not interfere with radio wave signals.

The NES protects the user against radiation emitted during surgery.

An NES will operate at an audible level that will not disrupt the user or those around the user. Any noise that is produced can be limited and can be at a very low decibel level.

System Compliance for User Comfort

Temperature: The NES can be temperature controlled to maintain maximum user comfort. The internal temperature of the NES can be set by the user to have a constant temperature throughout the system. The system also has the ability to maintain a desired temperature within certain sections of the NES. For example, if the user prefers that the torso section is cooler than other sections of the NES, then the user can set the thermostat of the NES for the torso region to maintain a cooler temperature. The distribution of cool or warm air can be achieved through an additional layer of material at the surface of the user's body that contains channels from which air can travel and be distributed. The cool air can be pumped in through an outside system or through a system that resides on the NES itself. This layer of material can also serve as a means to provide breathability to the system ensuring that the user remains comfortable. In the embodiment where the actuation of the material occurs through the transfer of matter, the matter can be cooled or heated to assist with temperature control while also serving as the means for which the actuating material actuates.

NES Self Containment: An NES can have antimicrobial properties and can be impermeable to materials outside the NES. For example, during surgery, a surgeon can be exposed to biological fluids and typically wears protective clothing to protect against exposure to biological fluids. The surface of an NES can be resistant to any penetration of these fluids and be easily cleaned or sterilized when exposed to them. It can contain properties that make it resistant to odor. The layer of impermeability can also mean that the NES is waterproof and can be used in applications where exposure to water or other fluids would be probable and may involve the NES being completely submerged in the fluid. In another embodiment of the NES, the system contains pores that can expose the outside environment to the surface of the user's skin. These pores can be a permanent opening that allows for breathability and more comfort for the user. In another embodiment of the system the pores are able to close completely, again completely protecting the user from the outside environment or limiting the user's exposure to the outside environment. The pores can open to varying degrees, depending on the user's needs. Opening and closing of the pores is directly controlled by the user or it can be automated and controlled by the NES computer or both. The opening and closing of the pores, and the degree to which they open and close, can be variable for different regions of the NES, depending on need.

IV—Component Embodiments of the NES

As previously mentioned, an NES can be a complete and independent stand-alone system that covers the entire body, most of the body, or portions of the body.

Figure 41:
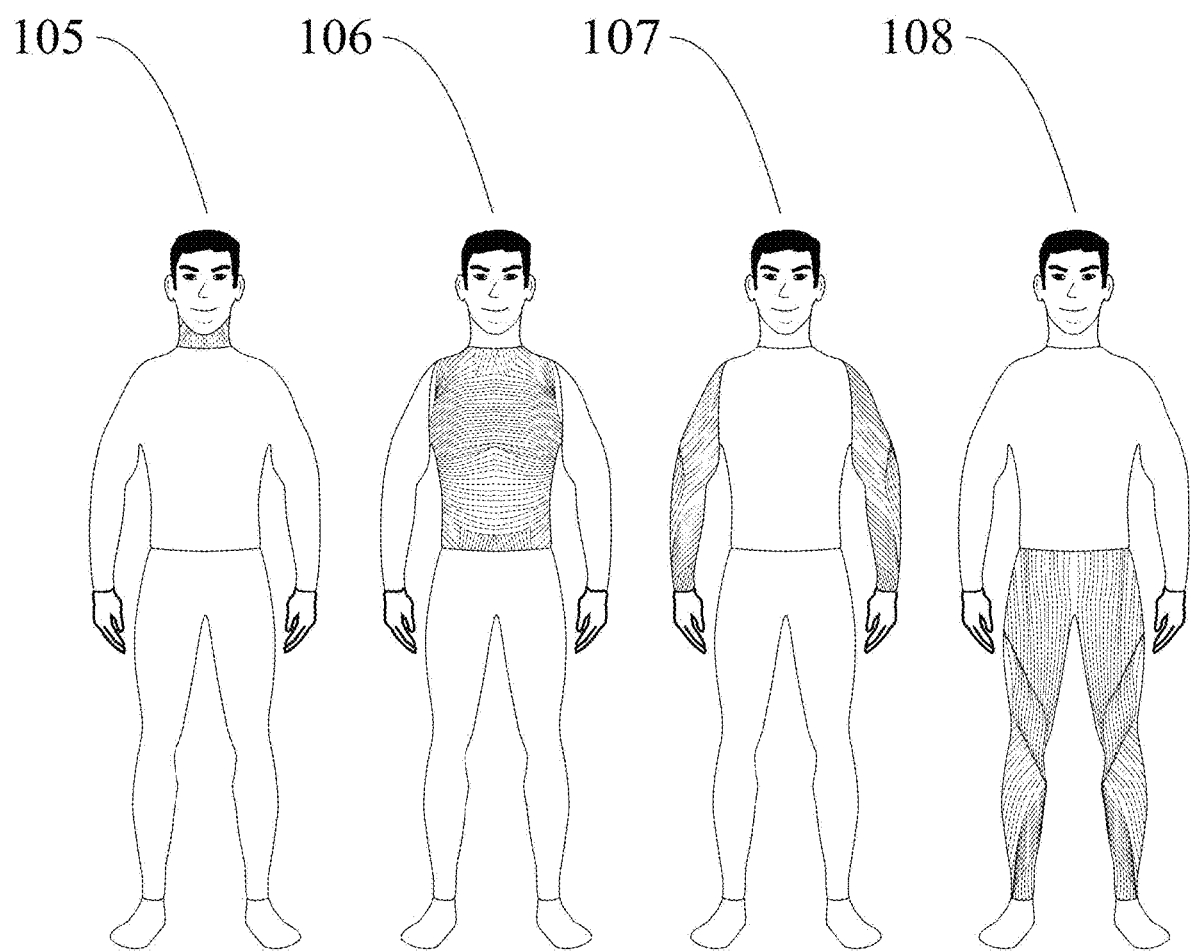
FIGS. 41-47 provide schematic illustration of various embodiments and methods for joining them.
Figure 42:
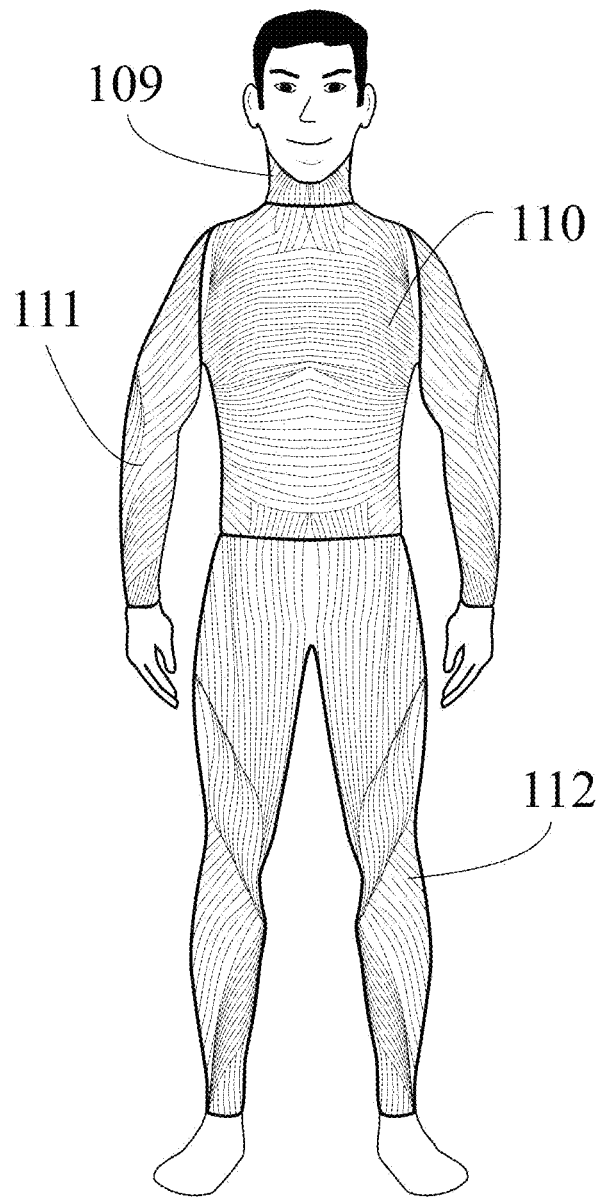

Stand-alone Embodiments: Examples of complete and independent stand-alone NES embodiments are depicted in FIG. 41. This figure shows an embodiment of a stand-alone NES that covers only the neck 105, an NES embodiment that covers only the torso 106, an NES embodiment that covers only the arms 107, an NES embodiment that covers only the lower body 108. Other stand-alone embodiments not depicted by FIG. 41 include embodiments that cover the head, hands, and feet. The user can use any combination of stand-alone embodiments of the NES simultaneously, short of a complete NES that covers the entire body, or wear all stand-alone embodiments of the NES, which when combined total a complete NES that covers the entire body. As shown in FIG. 42, for example, the user can wear a neck embodiment 109, a torso embodiment 110, arm embodiments 111, and an embodiment that covers the lower body 112.

Figure 43:
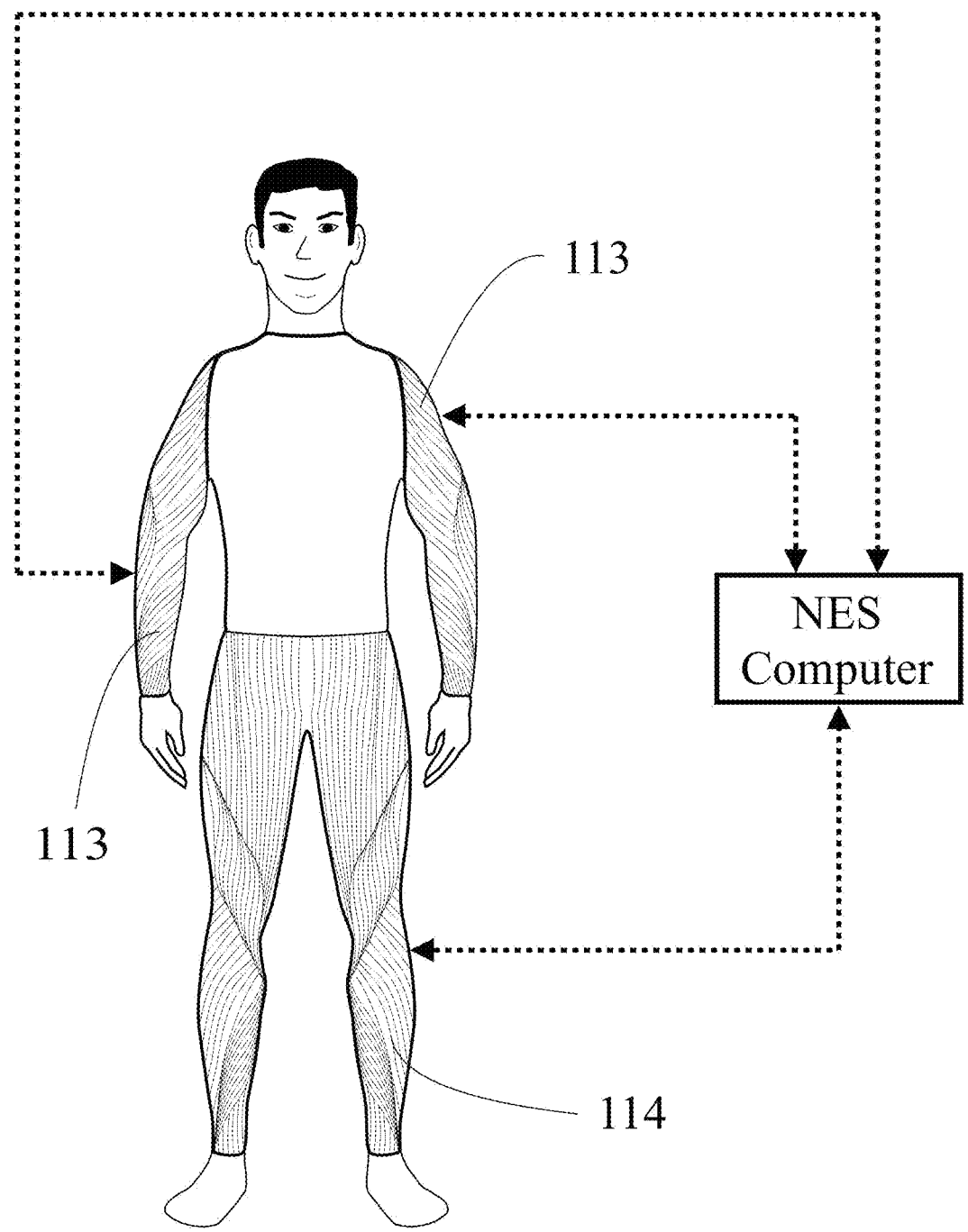

Each embodiment functions independently of the other, if desired by the user, or they can work in unison. As shown in FIG. 43, for example, if the user decides to use just two arm embodiments of the system 113 and just the lower extremity embodiment of the system at the same time 114, then each embodiment can function independently of the other in that they would not need to communicate directly with each other. They would only need to communicate with a single NES computer system, or an NES computer system dedicated to the arm embodiment and another NES computer system dedicated to the lower extremity embodiment.

Figure 44:
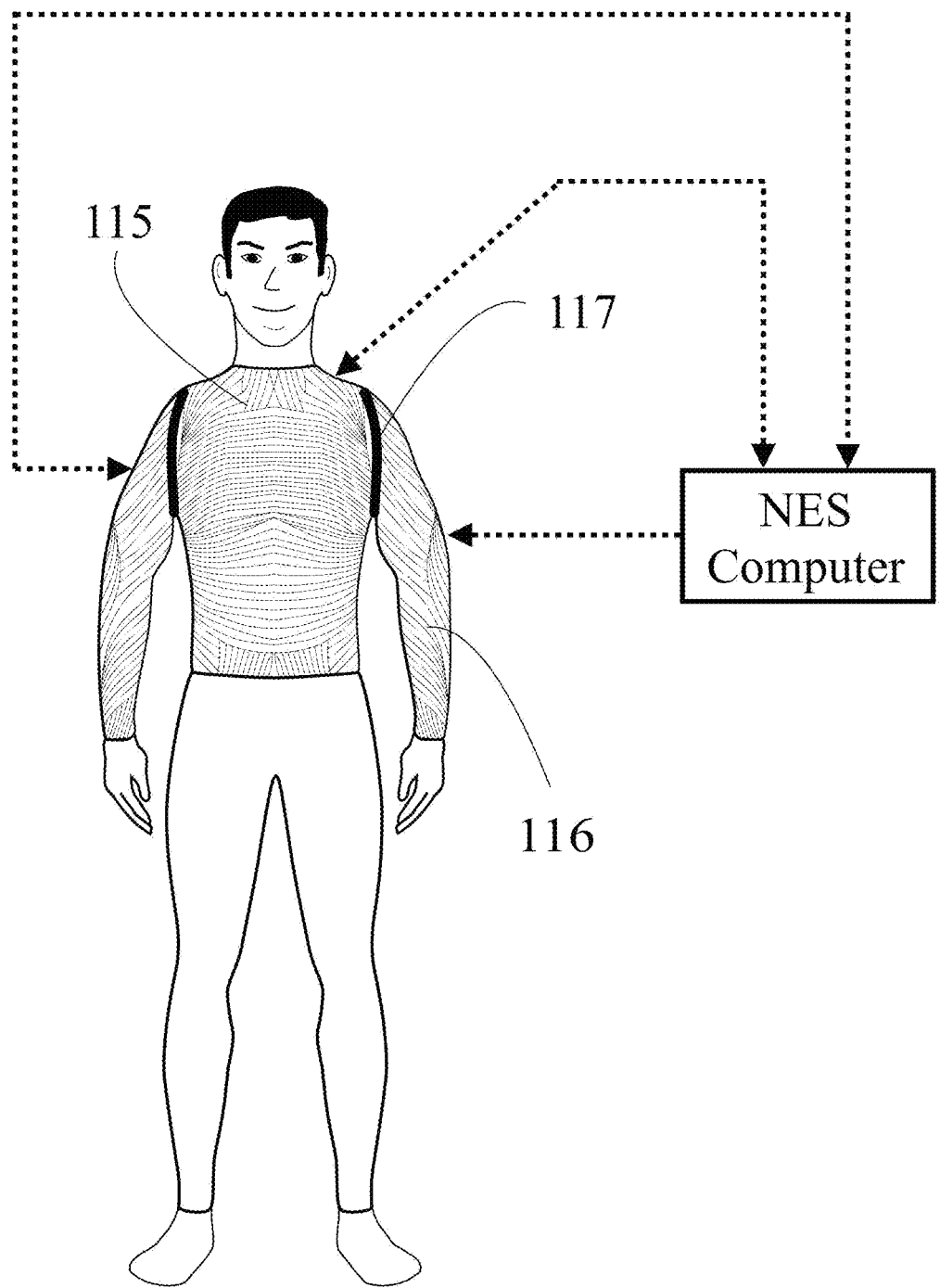
Figure 45:
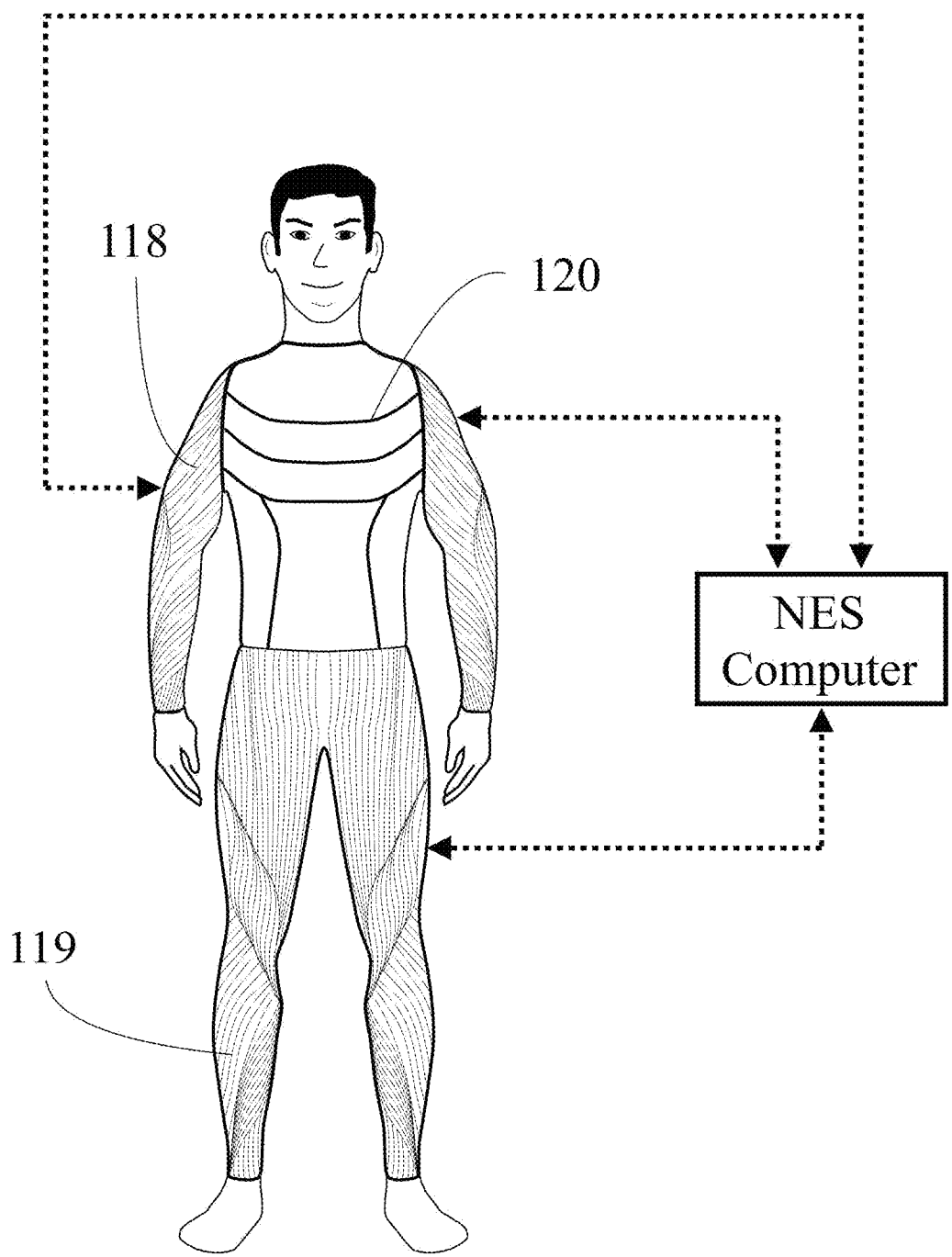

Joining Stand-Alone NES Embodiments: Conversely, if the user wishes to combine the stand-alone embodiment so that they do communicate with each other directly and function together, they can be connected to each other through a communication and power network that allows the embodiments to do so. As shown in FIG. 44, this connection can exist in a contiguous nature, i.e., one embodiment physically connected to the other. For example, a torso embodiment 115 connected to arm embodiments 116 where the embodiments are directly connected to one another and share a common border 117. Or, as in FIG. 45, the connection may be physically discontiguous in that the embodiments do not share a common border but are still linked to each other through communication and power networks. For example, arm embodiments 118 can connect to a lower extremity embodiment 119 through the communication and power networks 120. These communication and power networks can consist of wires, cables, or any other conducting material that link the different embodiments to one another. They can exist as an embedded network within a wearable item whose sole purpose is to provide a communication and a power network to other embodiments, or they can exist embedded within an NES embodiment composed of actuating materials.

When different embodiments are connected in a contiguous manner, the communication system and power system can be physically linked through interlocking connectors that exist at the points where the embodiments physically terminate and have a physical border that can join the physical border of another embodiment. The embodiments can connect in a variety of ways. A user wanting to connect one embodiment to another embodiment can align the two embodiments together and twist and snap the two embodiments together in a manner similar to the way a spacesuit glove connects to a spacesuit. For example, an arm embodiment and a shoulder embodiment can each have threaded ends that can be aligned then twisted and locked using the threads and a locking mechanism. The terminals of the communication and power systems for both embodiments can physically align and link together through the ends where the embodiments terminate or though the locking mechanism.

Figure 46:
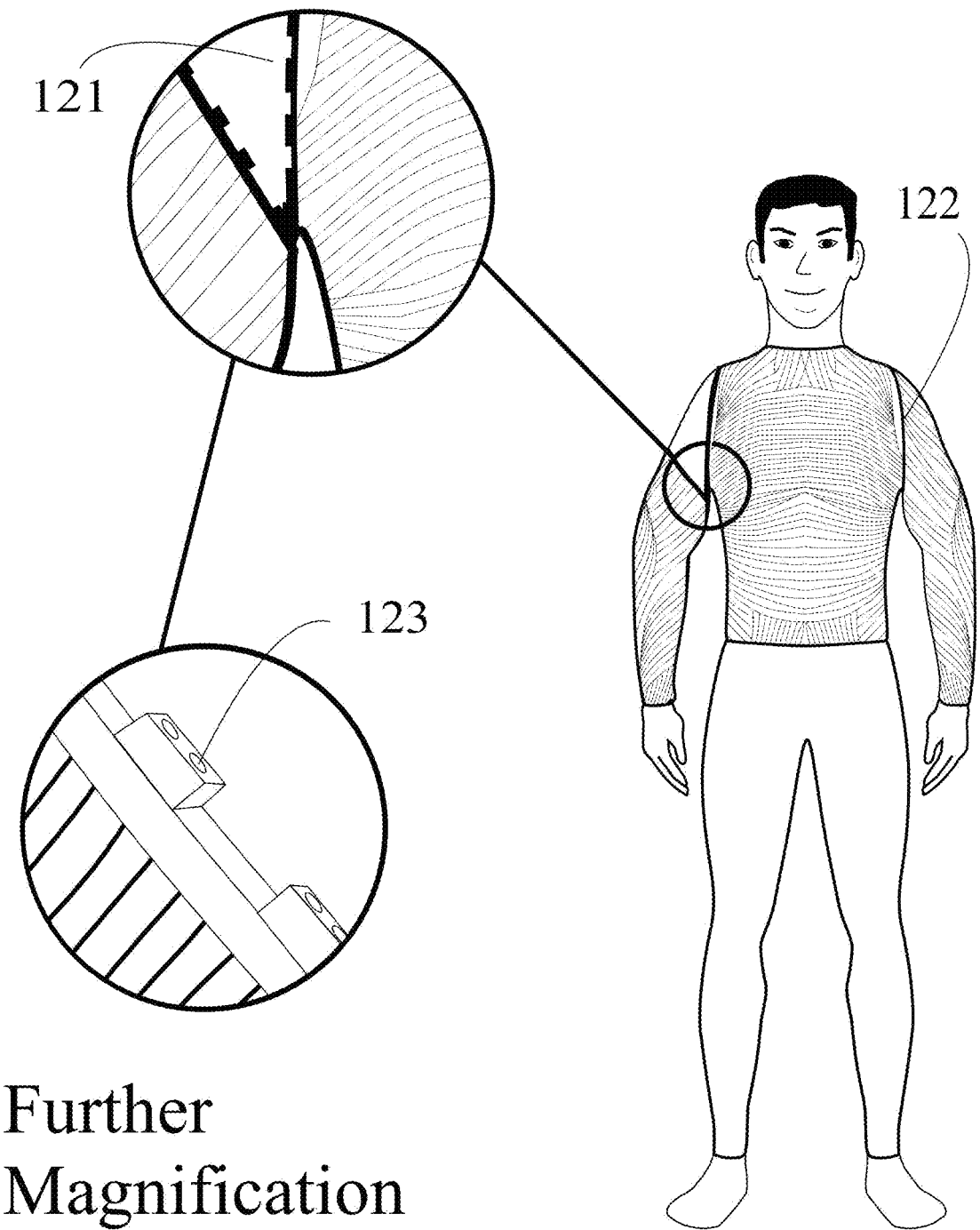

Another embodiment of the interconnecting components is illustrated in FIG. 46. In this embodiment the components have magnetized connectors that when close in proximity self-align and close similar to the way a zipper closes 121. The magnetized system can hold the terminating ends of the components together 122. Communication and power contacts can line the zipper-like surface 123 so that when the two components are joined physically, they are also linked through the communication and power system. The connecting structure can have any geometry and is not limited to a geometry that resembles a zipper. Another embodiment exists as a sheet of NES material that can wrap around any part of the body, seal itself as previously described by having its open ends joined together, conform to the user's body, and perform in the same way that any other embodiment performs.

Figure 47:
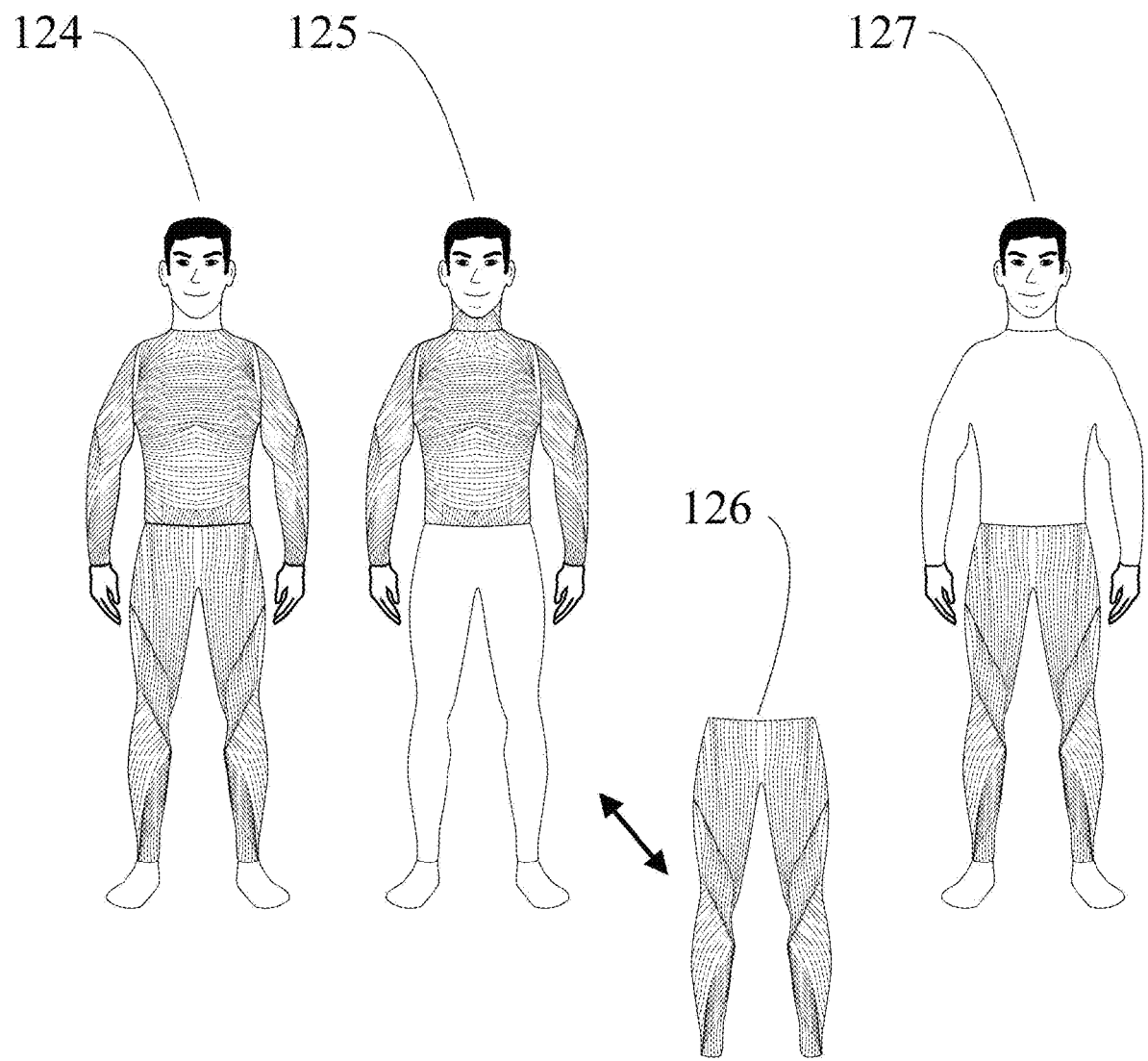

Sectioning of an NES Embodiment: NES embodiments can be customized based on the user's needs. FIG. 47 shows an NES embodiment 124 that can have sections of it removed. This is useful in a situation, for example, where the user wishes to use only the torso, neck, and arm components of the system for a particular task 125. He or she can remove the lower portion of the NES below the torso for that task 126, but connect with the upper portion of the NES for a different task carried out at a later point in time. A user can wear another embodiment consisting of only the leg portion of the NES 127, if the user knows that the tasks he or she will be performing require only physical enhancement of the legs. These various sections of the NES can connect and or link to each other in the ways previously described. An NES can also give the user the ability to turn off, or operate in a reduced power state, certain sections of an NES if he or she wants to use only a particular section of the NES. For example, in order to conserve the energy required to power the system, the user may elect to turn off all sections below the user's waist, if he or she will be sitting and will not need enhancement of the legs. An NES also gives the user the ability to turn off certain regions within any embodiment. For example, a user can turn off the bicep section of an arm embodiment of the NES if he or she will not be using the features of the NES for the bicep.

V—Supplying Power to the NES

An NES requires power for the various components and functions of the system: powering the actuating materials, supplying power for communication between the different layers of actuating materials, supplying power for the interaction between the different actuating materials, supplying power for the communication with various other systems. These various systems, which can consist of systems that are both physically connected to the NES and not physically connected to the NES, can include but are not limited to computers, medical imaging equipment, sensors, surgical tools, and surgical navigation systems.

Figure 48:
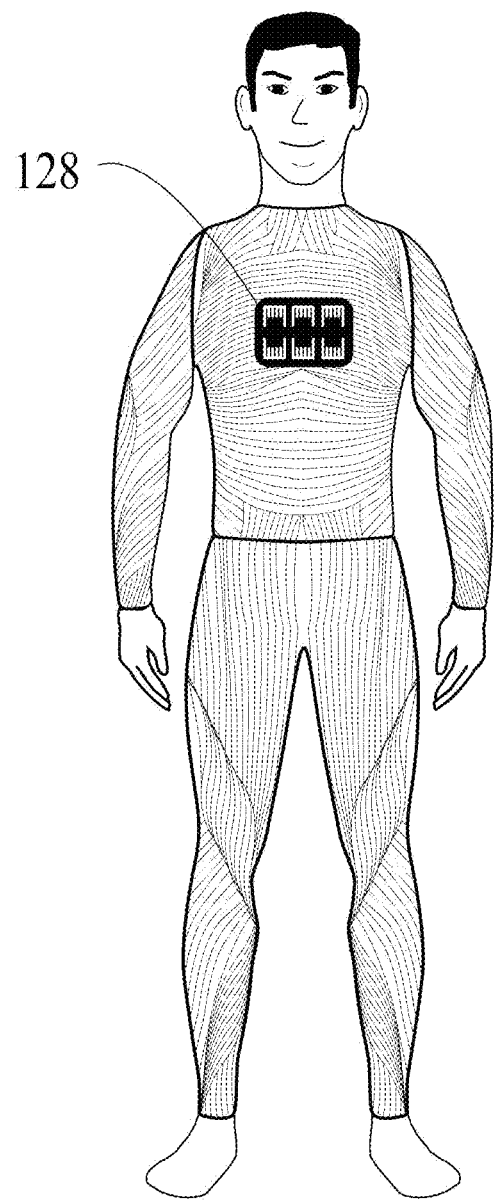

Various embodiments to power the NES exist. FIG. 48 depicts one embodiment that contains one centralized power unit 128 connected to the NES. This centralized power unit can be modular in nature, similar to a battery pack or a canister of air, and can be connected to various parts of the body.

Figure 49:
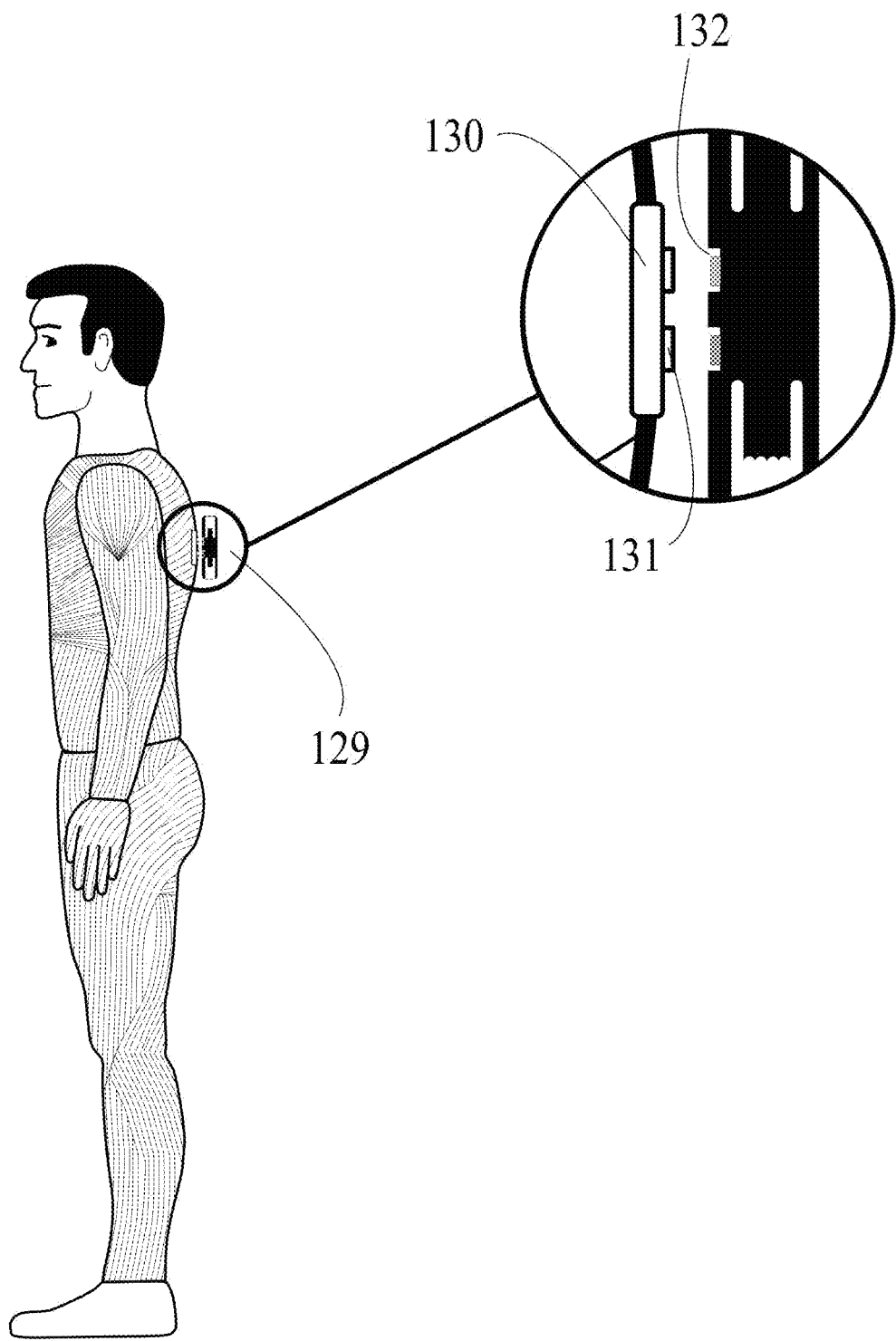

System Terminals: FIG. 49 depicts an embodiment with a terminal used for connecting sources of power. The terminal can be used for mounting mobile power units 129 to supply power to the NES and its various components. The terminals can also be used for connecting the NES and or components of the NES with a communication network and or computer system. These terminals can be woven into the surface of the NES 130. The terminal can serve as both a conduit for the power 131 stored in the power unit, and as a connection point where the power unit attaches and secures to the NES 132.

Figure 50:
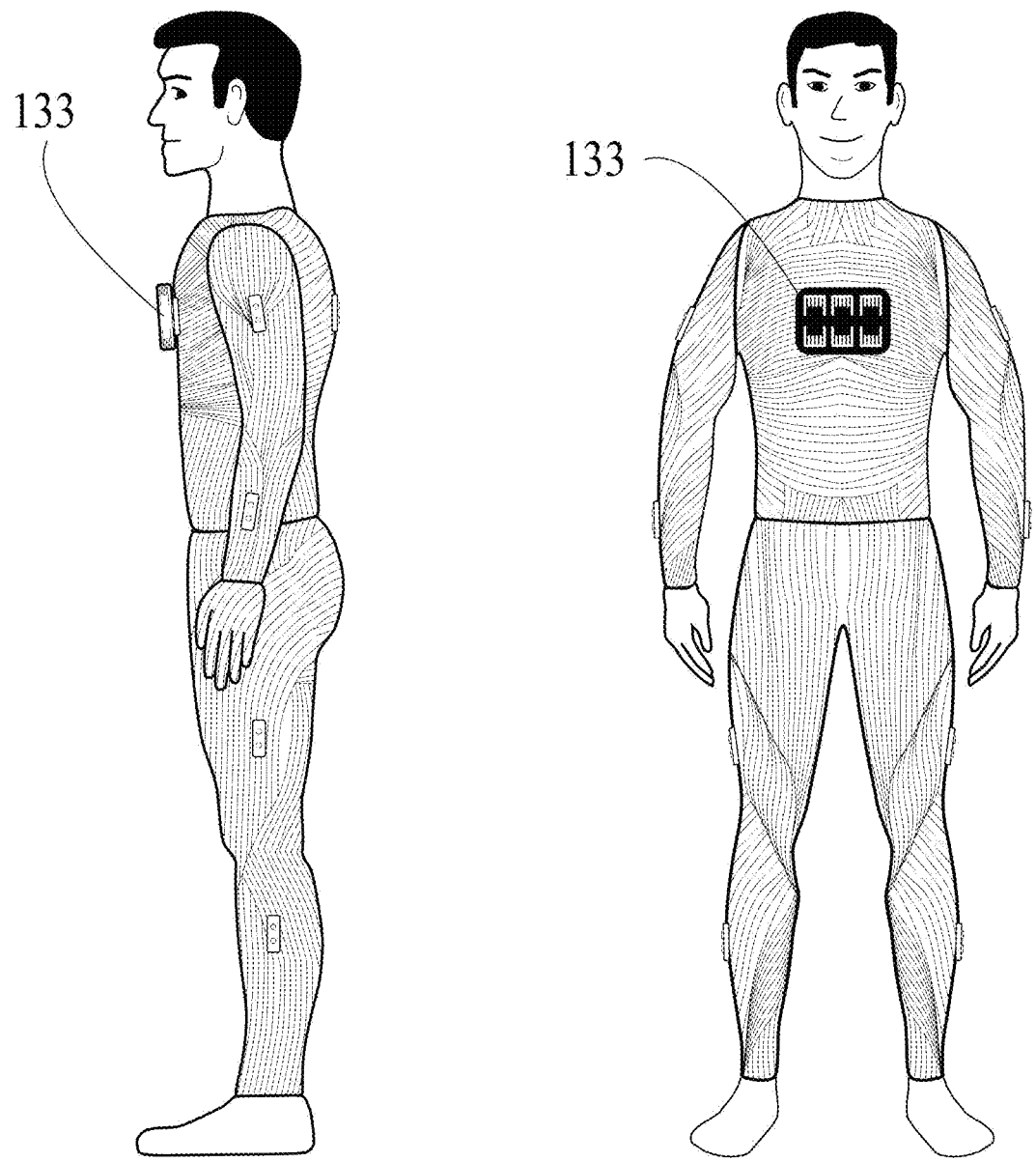
Figure 51:
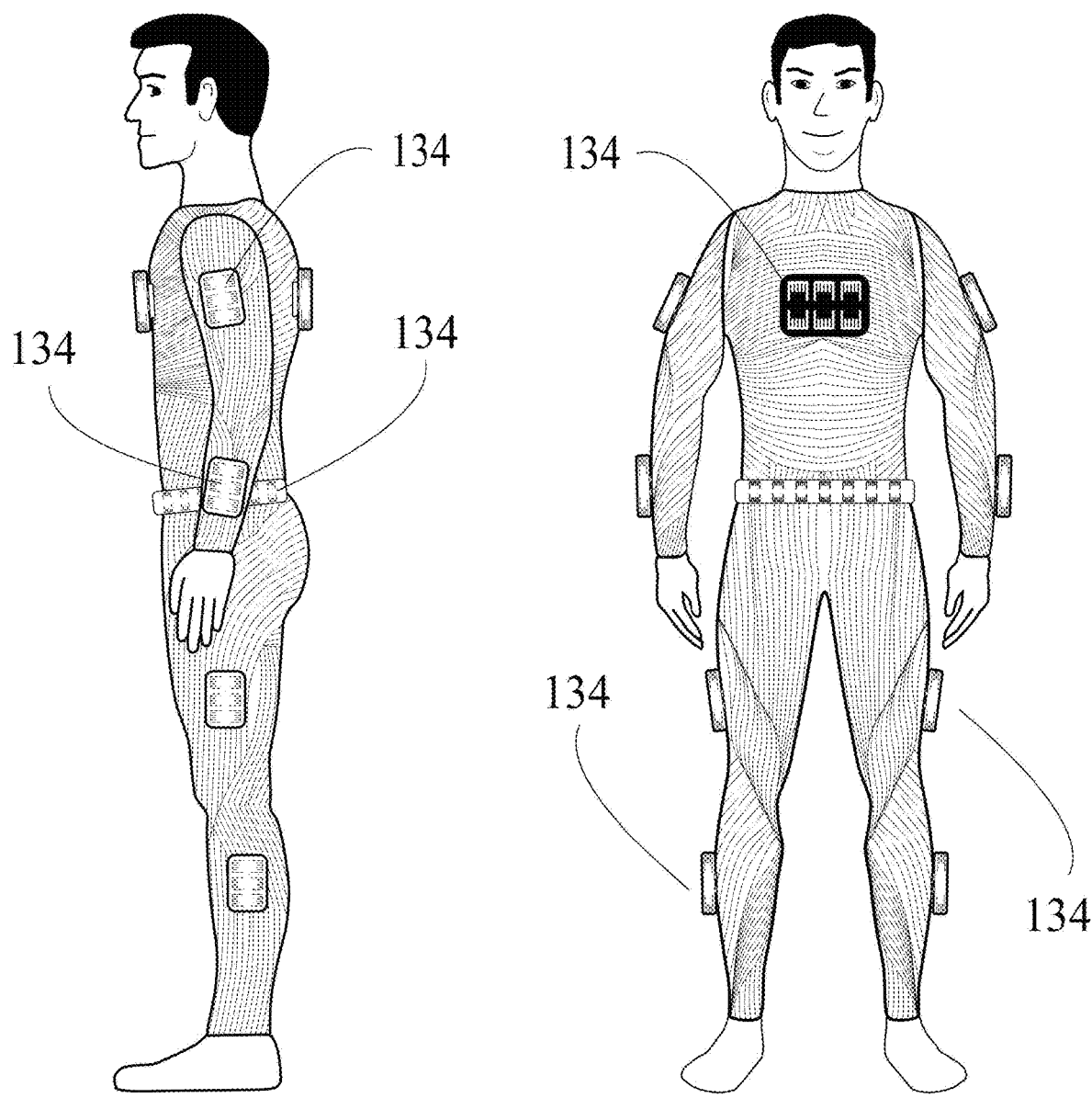

Methods for Supplying Power: Power can be provided to the NES through one power unit or an array of power units. In instances where more than one power unit is used, the units can be connected to different terminals located at different parts of the body. As shown in FIG. 50, a single battery pack 133 can be used to power the entire system for a given amount of time, or, as shown in FIG. 51, multiple battery packs can be used to power the system for a longer duration 134. A different embodiment that uses an air canister or multiple air canisters to supply power instead of a battery pack or packs can also exist. Another embodiment may use a combination of different types of power to supply the NES.

The power unit can be a single-use power unit or it can be replenished, when needed, with the type of energy that it is designed to supply. For example, the unit can be a rechargeable battery or a canister of air that can be removed and replaced with another unit or replenished at any time when more power is needed.

The NES can have indicators that notify the user when power is running low and a new power unit is needed to power the system. The indicators can be audible, visual, or haptic in nature. For example, a vibration in the NES at a specified location can indicate that more power is needed. The indicator signal can emanate from the NES itself or from an outside system. An indicator can specify which particular pack or packs need to be replaced or replenished.

Figure 52:
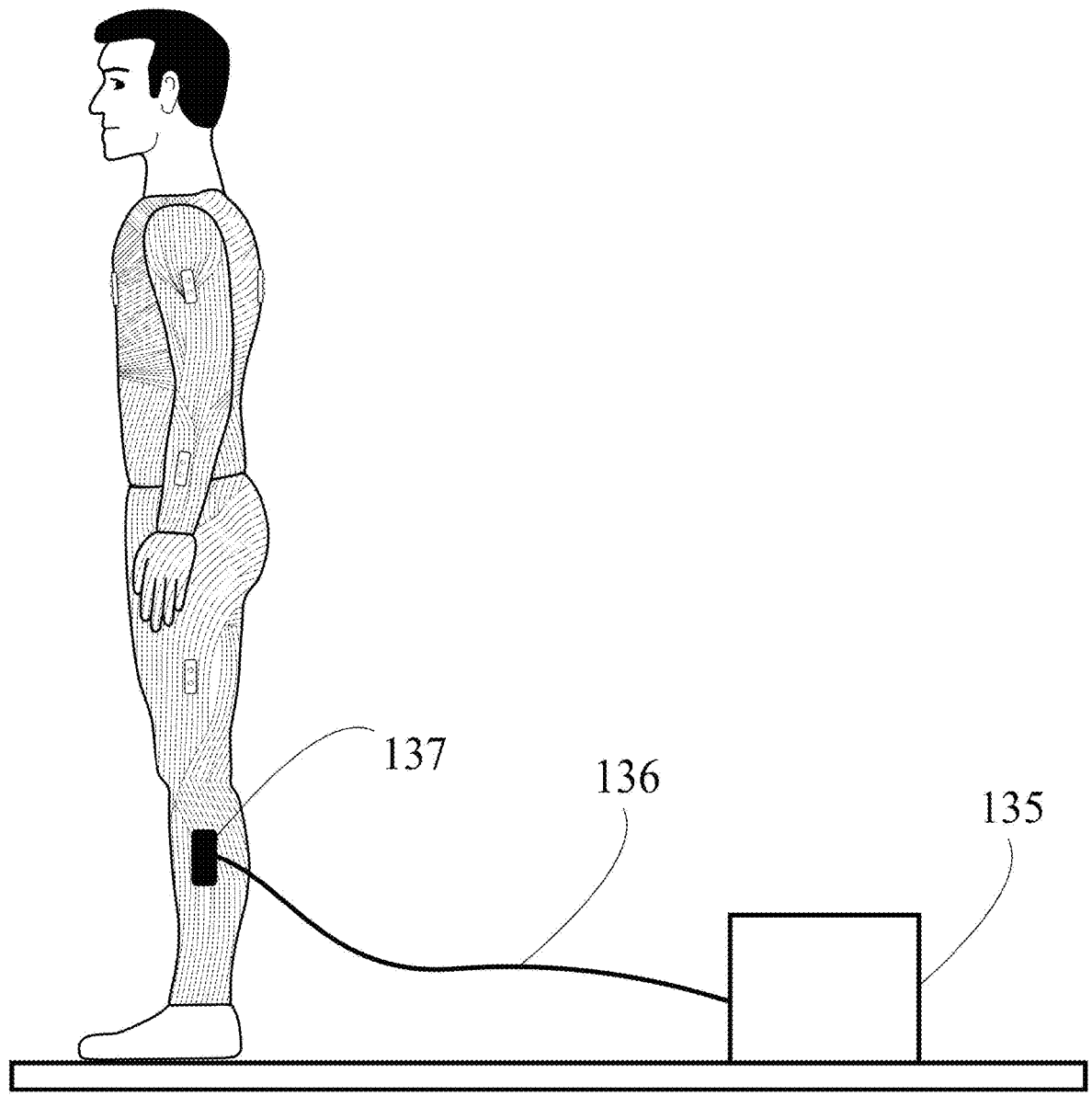

Power can also be provided to the system, as shown in FIG. 52, by a stand-alone power unit 135 separate from the NES. This power unit can be connected to the NES with one or more power cables 136, or any other power transmission mechanism. The power cable can be connected to any of the various terminals on the NES 137. For example, the user may wish to connect the power cable to a terminal on a leg instead of the upper body if he or she will be moving the upper body for a task and wants the upper body to be unconstrained by a power cable.

Figure 53:
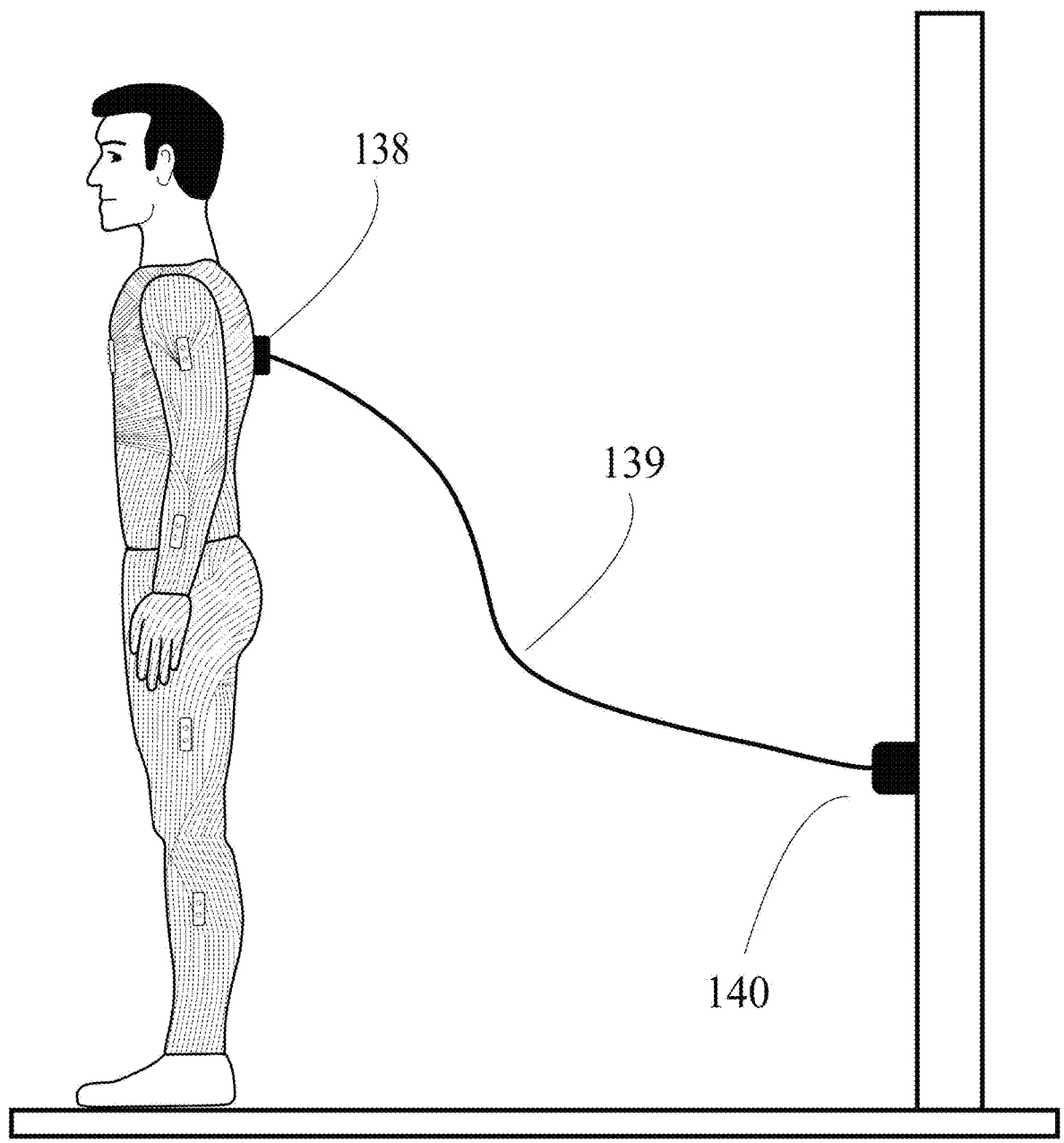

Power can be provided to the entire NES, as shown in FIG. 53, by connecting a power source to just one terminal 138. Power supplied to this terminal can be provided by connecting the terminal with a cable 139 to a standard 120-volt electrical outlet 140. An NES can have the capability of converting the alternating current from the 120-volt electrical outlet to direct current.

An NES can be configured to receive power through a combination of a standard 120-volt electrical power source and a power unit as the ones previously described. Multiple power units can also be connected in this configuration. In other words, the power unit or power units can be connected to the NES at the same time it is connected to the 120-volt electrical power source. The NES will function under normal conditions with these two power sources supplying power to the NES. While connected to the 120-volt source, the NES is able to recharge any power units that are connected to it.

Power can be provided to the NES through a system of induction terminals that the user is in frequent contact with or in close proximity. For example, a chair, the operating room table, or the floor can incorporate these induction terminals. The induction terminals eliminate the need for battery packs to be worn by the surgeon and eliminate the need for the surgeon to stay tethered to an external power source. The induction terminals themselves can be battery powered or can be powered directly with electricity from a 120-volt electrical power source, for example. The induction terminals on the NES that receive power can be located at strategic locations, or the NES can be configured so that induction can occur through terminals woven into the actuating materials throughout the NES. The induction charging frequency can be set so as not to interfere with equipment or with the NES itself.

In another embodiment of the NES, the NES itself can contain a power source within its fabric. This source can be recharged by means previously described.

Figure 54:
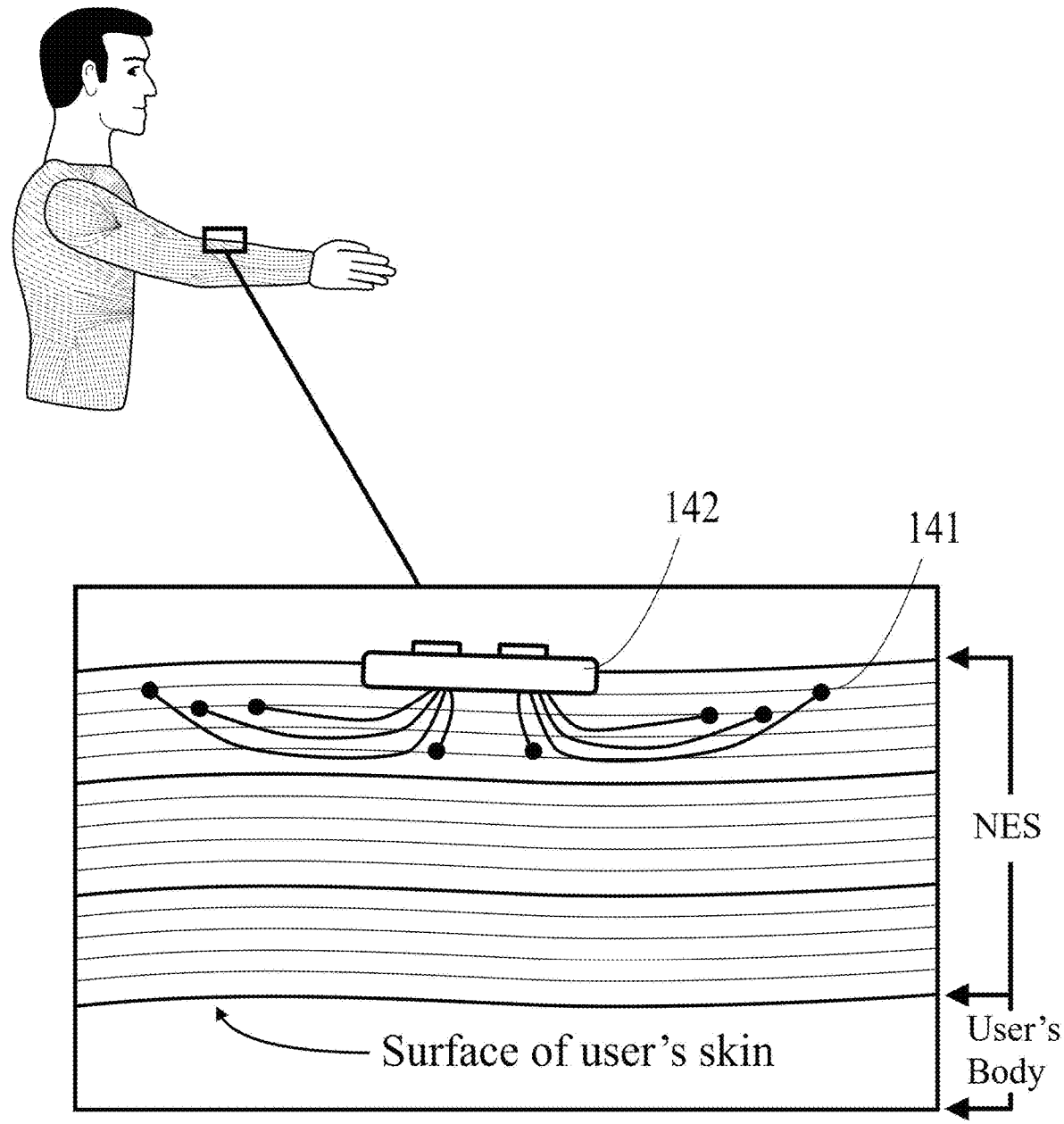
Figure 55:
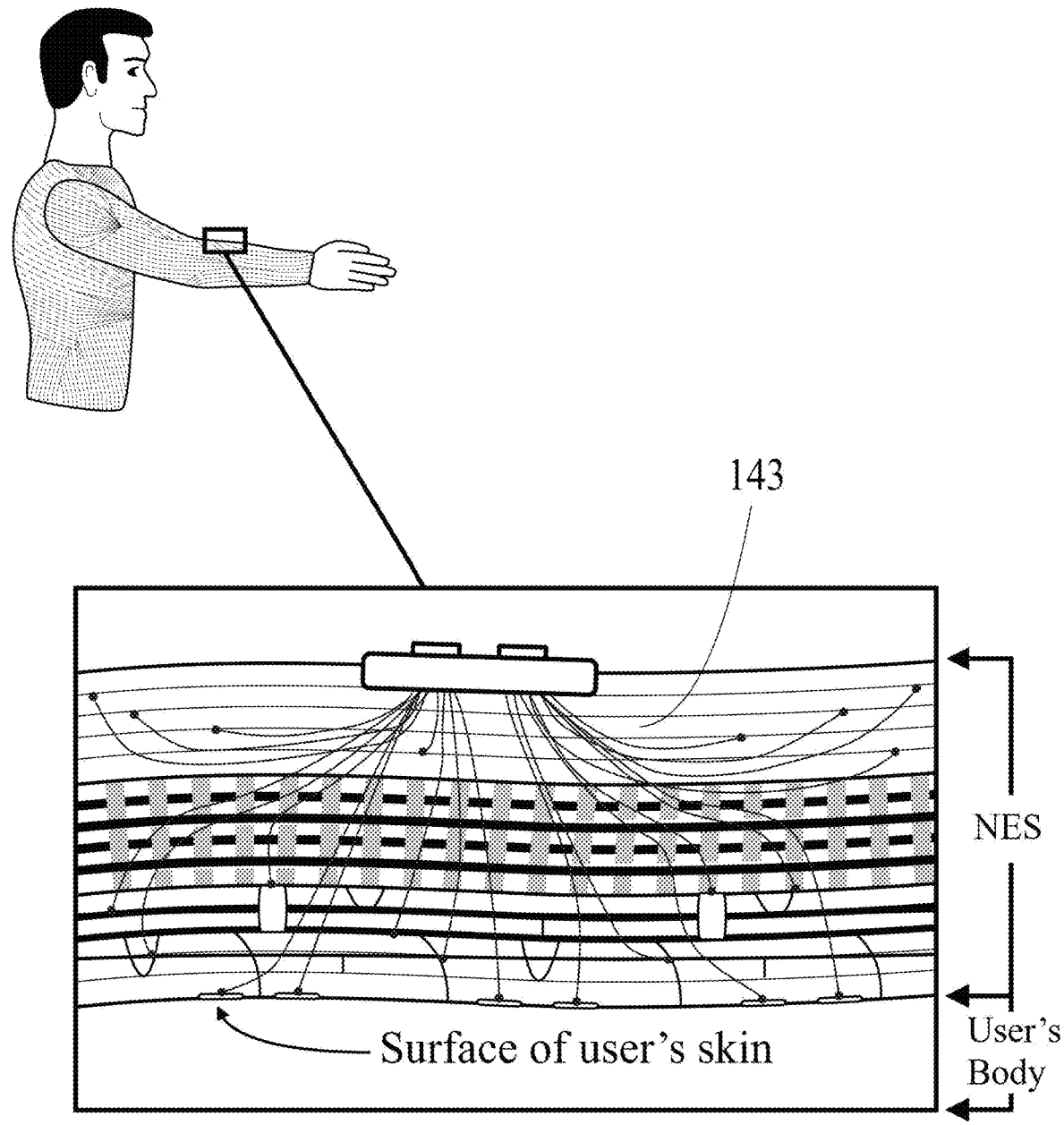

At a local level, as shown in FIG. 54, the power supplied to actuating materials or other elements of the NES can be transmitted through a network of conduits that supply the power 141 and originate at the terminal 142. These conduits can be in the form of flexible wires, cables, or any other conducting material as in the case where electricity is being provided, or they can be in the form of hollow channels or tubes, as in the case where pressure is the source of power being provided. These networks are flexible so that the contourability properties of the NES are not diminished. As shown in FIG. 55, the network 143 can be interwoven within the various layers of actuating material crossing one or multiple layers. As shown in FIG. 56, the group of actuating material can be powered in parallel 144 or in series 145 by these networks that provide power.

In the embodiment where power being supplied is in the form of electricity, the network of electrical conductors can also serve as conduits for power to the various sensors located throughout the NES, in addition to a conduit for the actuating materials. The network of electrical conductors can also be used to provide power to any signaling systems on the NES used to notify the user of events, or any other component that requires power.

VI—Information Processing of the NES

Figure 57:
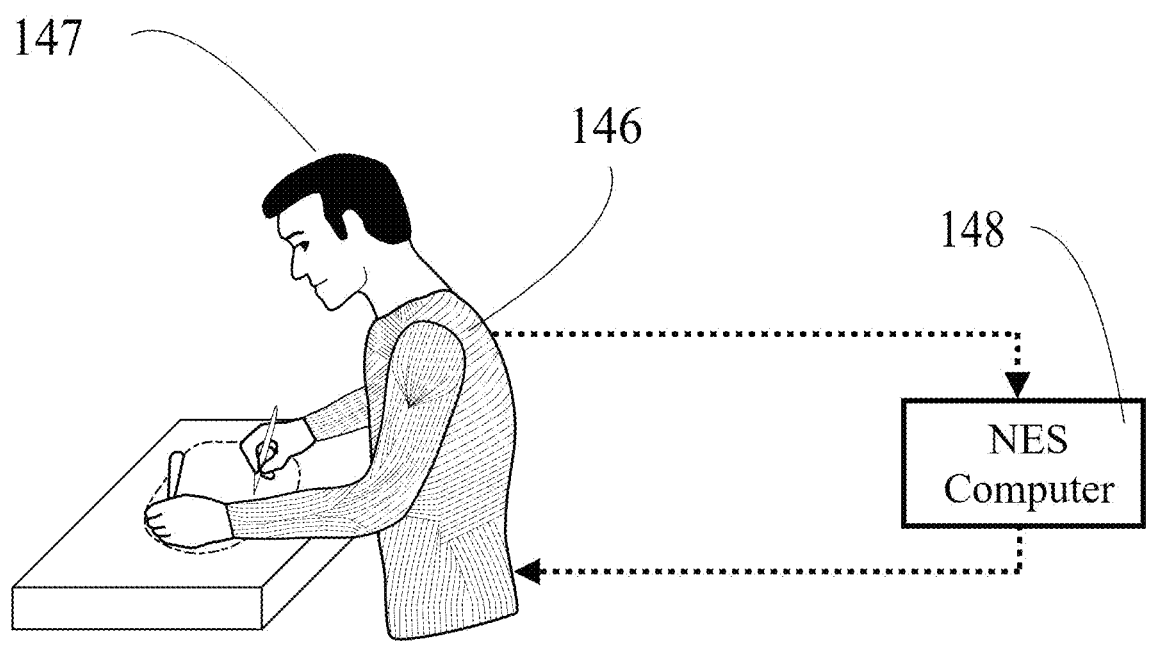
FIGS. 57-63 provide schematic illustrations for methods in which information is processed and computing power is supplied.
Figure 58:
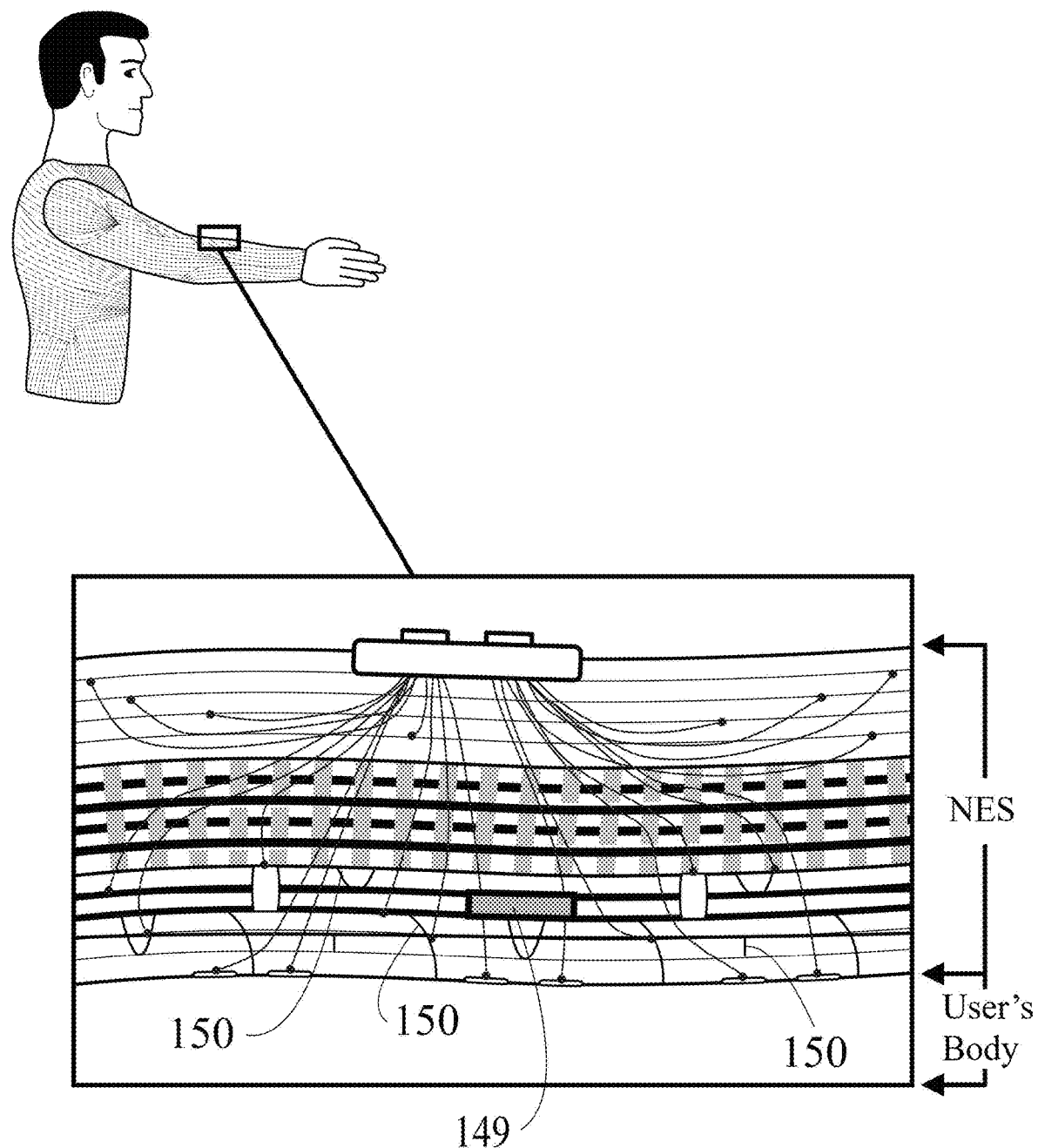
Figure 59:
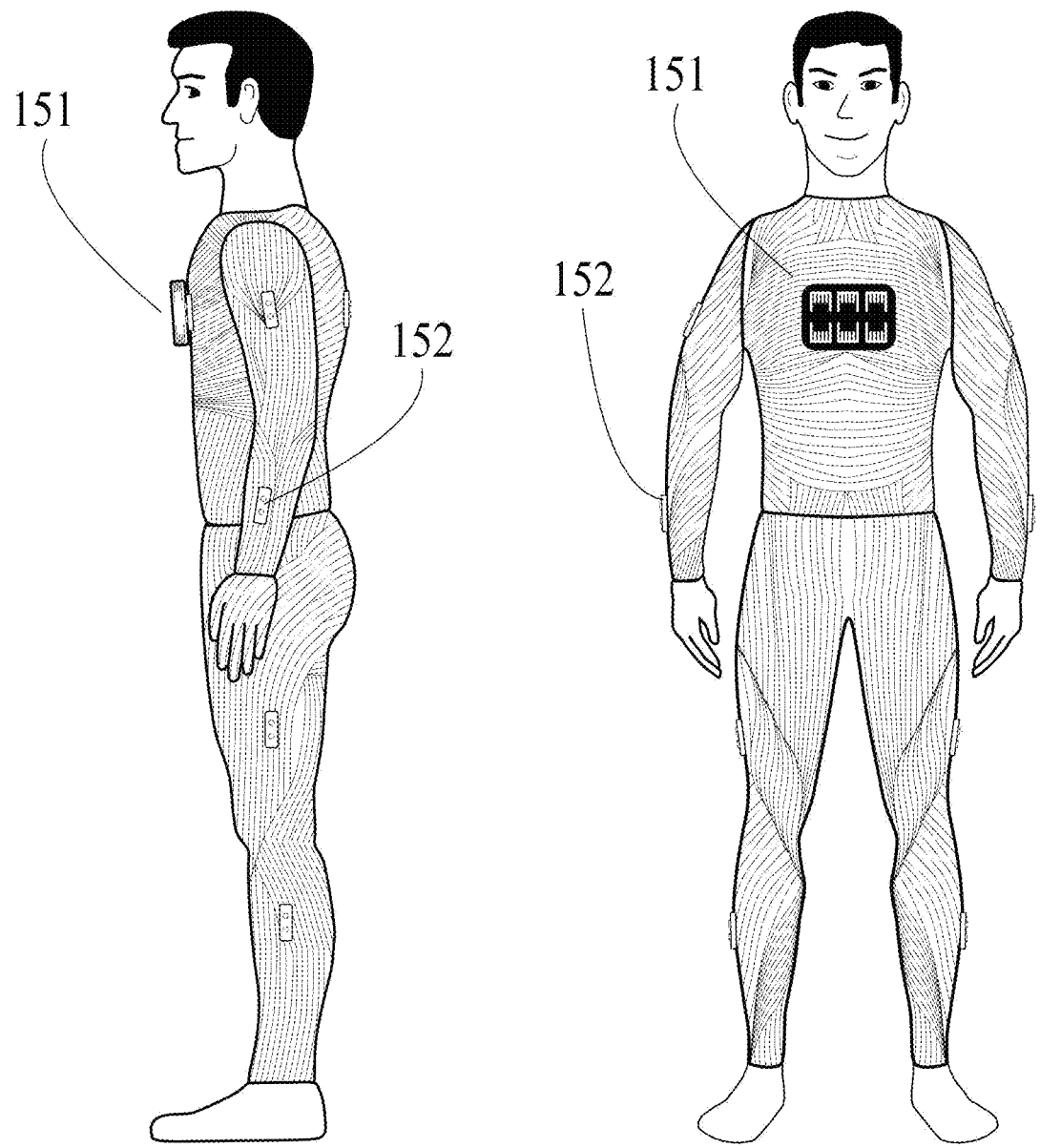
Figure 60:
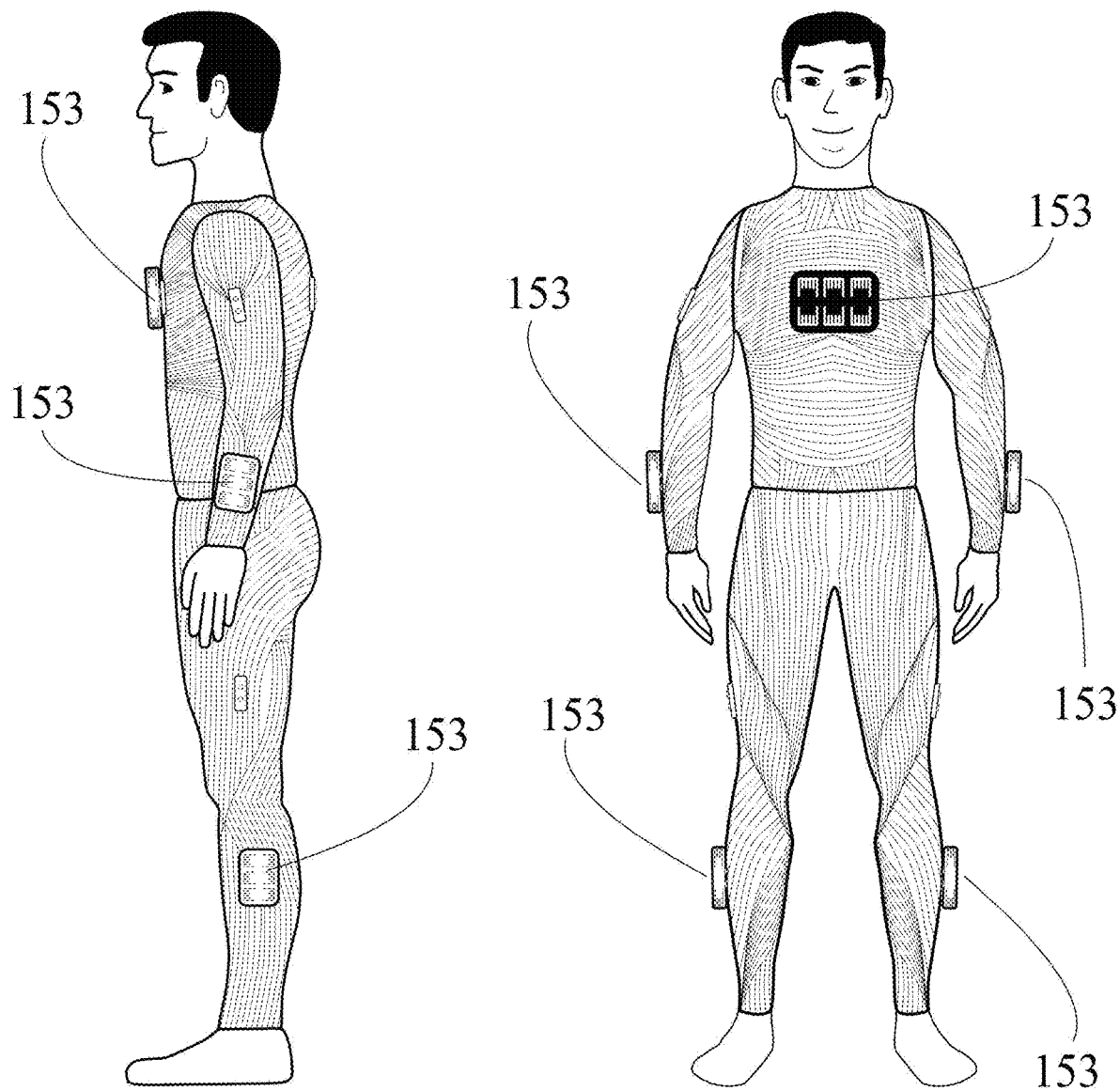
Figure 61:
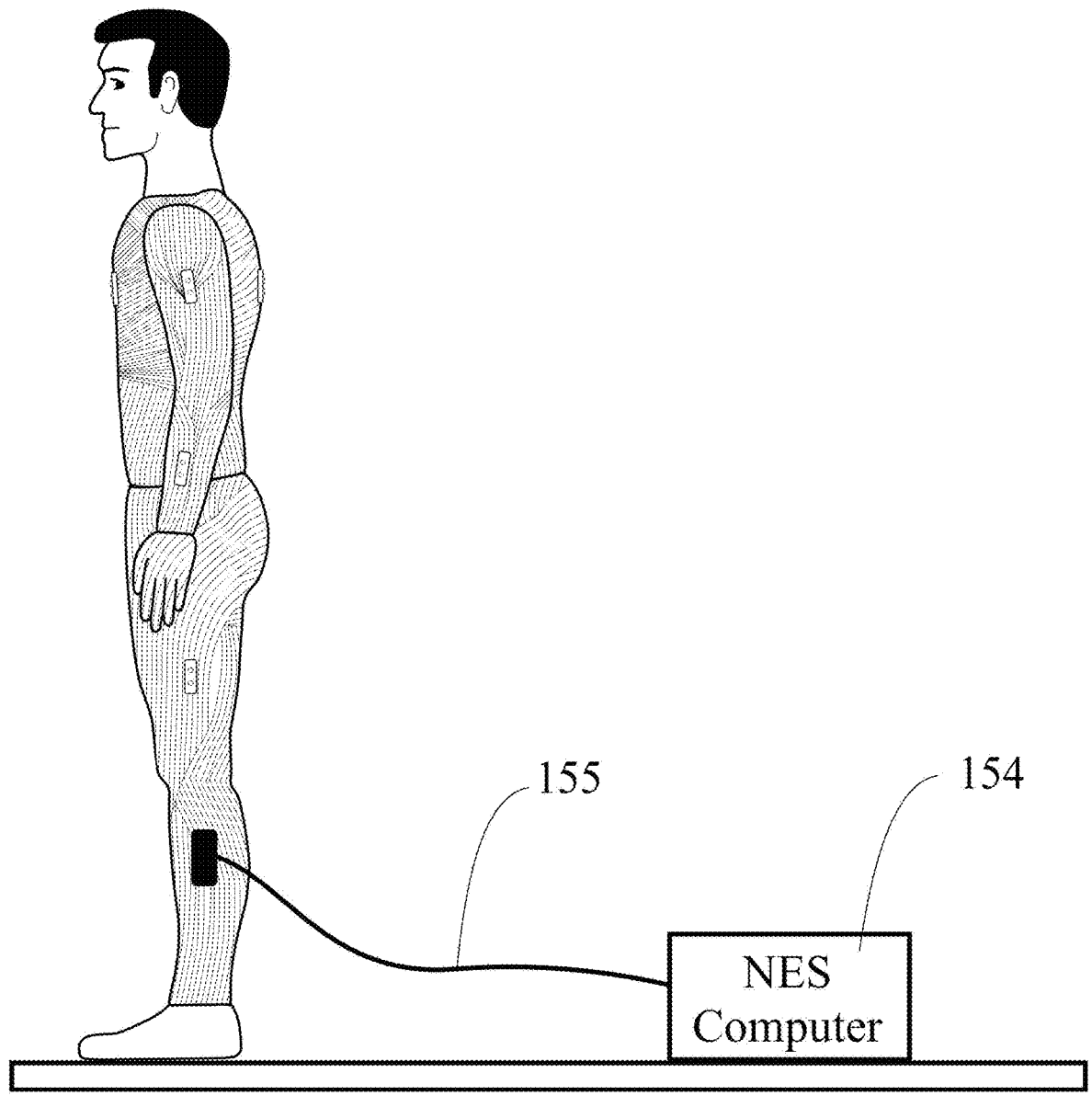
Figure 62:
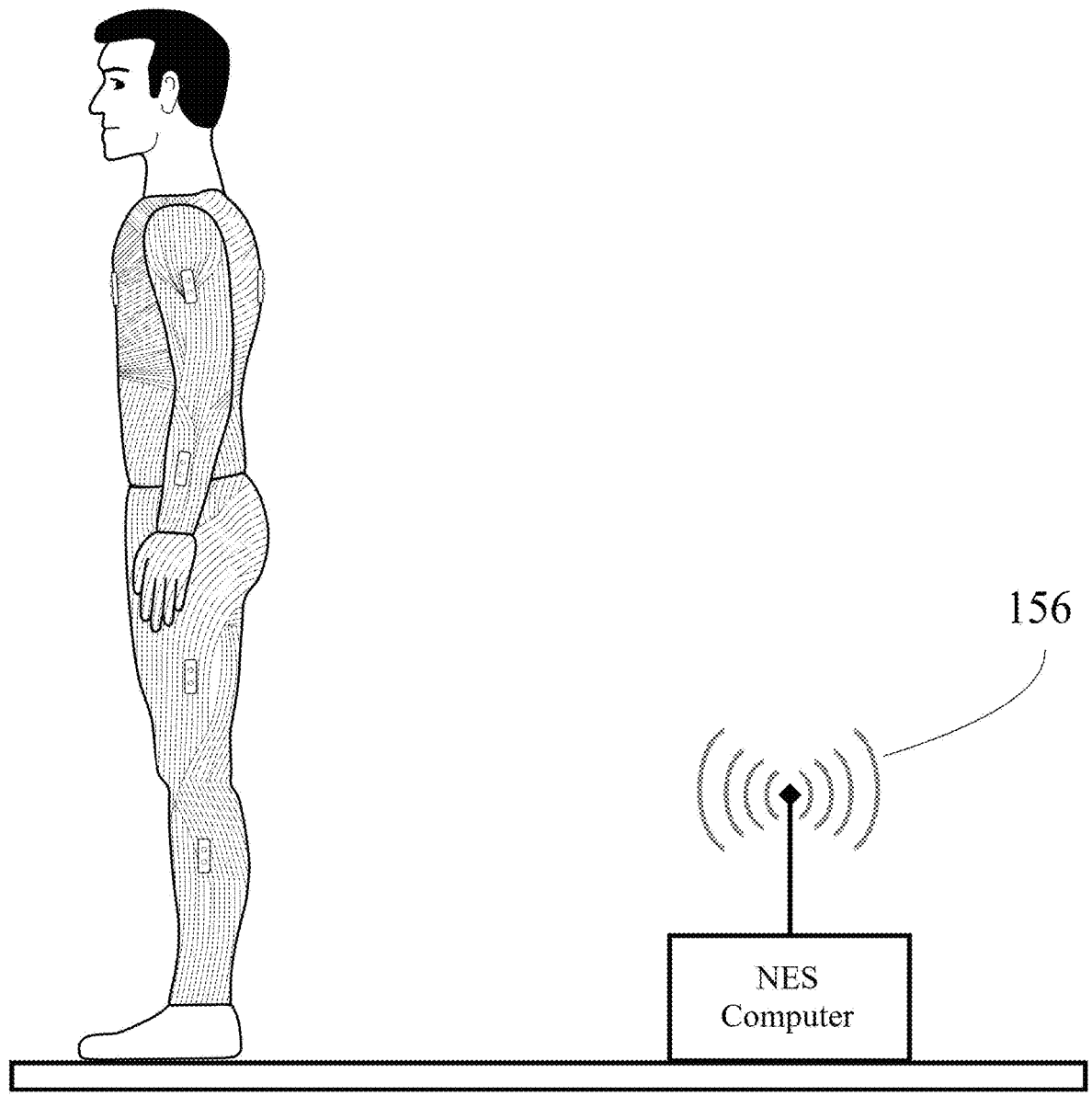
Figure 63:
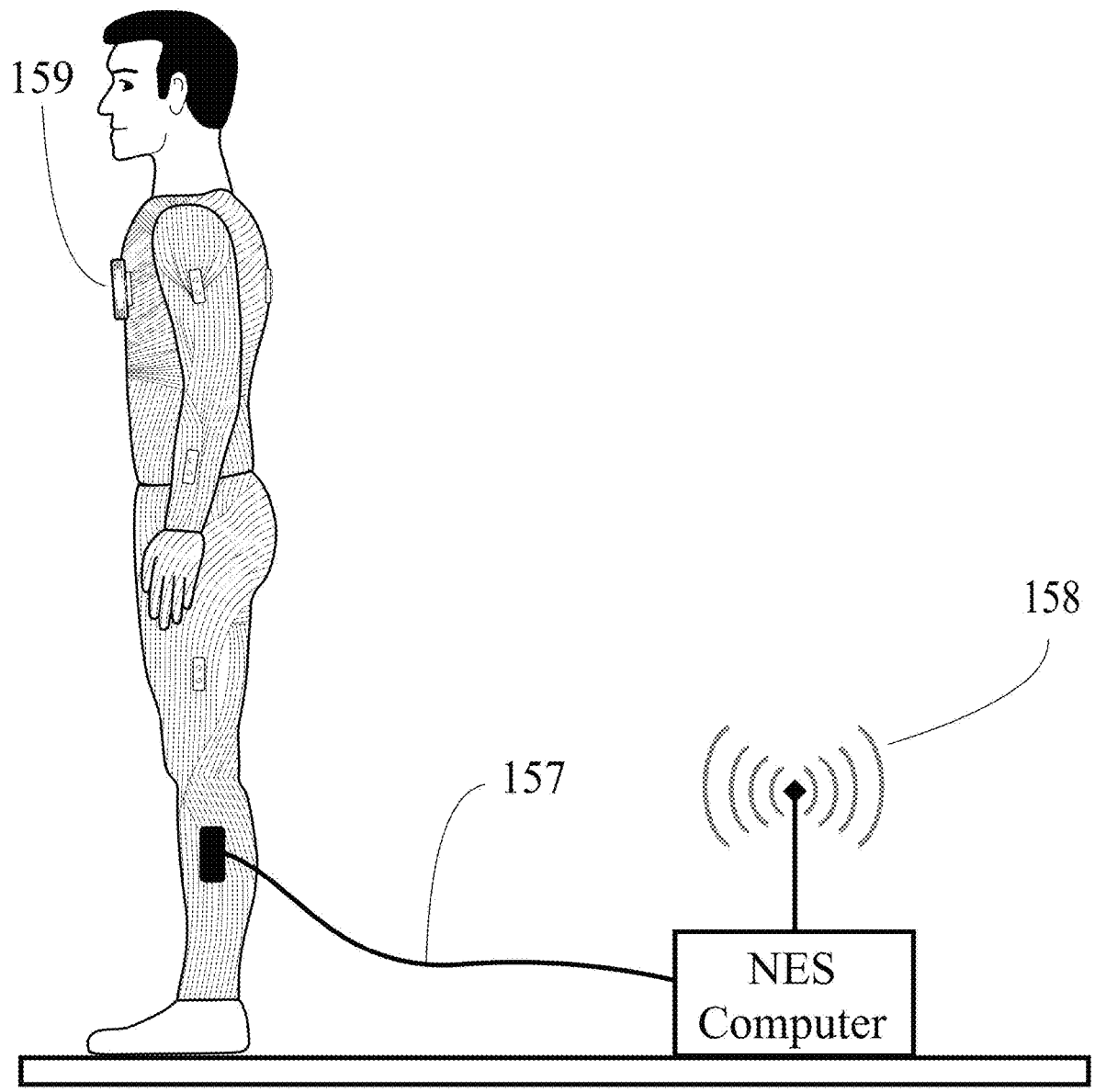

An NES can operate within a feedback loop as shown in FIG. 57 that includes the NES 146, the NES user 147, and the NES computer 148. Other systems can also contribute to the feedback loop, such as a fluoroscope or other medical imaging systems. The NES computer can physically reside entirely inside the NES, interwoven as shown in FIG. 58 with microprocessors 149 and other semiconductor and computer components 150 within the actuating material layers or other non-actuating material layers that comprise the NES. The computer system, as shown in FIG. 59, can also reside on the NES as a modular component CPU 151 that the user can connect to or disconnect from any of the terminals 152 in a similar manner that a power pack, as previously mentioned, can be connected and disconnected. The terminals can act as conduits that supply power to the NES and the various components, they can act as communication terminals for the modular component CPU, or both. As shown in FIG. 60, one or more than one of the modular component CPUs 153 can be connected to different areas of the NES. This can be done to meet additional CPU processing needs that a particular area of the NES requires, although the entire NES can be controlled through a single modular CPU unit connected to any of the terminals. A more powerful modular component CPU with more processing capabilities can be connected to the NES to control the entire NES. Additional modular component CPUs can be added for enhanced computing power. A modular component CPU can also be a combined CPU/power pack providing both computing capabilities and powering capabilities. The NES computer, as shown in FIG. 61, can also reside as a stand-alone unit 154 separate from the NES, but connected to the NES through an electrical conducting material 155 or a plurality of electrical conducting materials, such as cables or wires. The NES and stand-alone computer system, as shown in FIG. 62, can also connect to each other wirelessly 156. The stand-alone computer system and NES, as shown in FIG. 63, can connect to each other through a combination of wired 157 and wireless 158 means and have their processing power enhanced with the connection of a modular component CPU 159 or multiple modular component CPUs. All of these NES computer system embodiments can have the capability to communicate with various pieces of equipment in the operating room, such as medical imaging equipment or other computer systems. This communication can exist either through a wired connection or through wireless technology such as Bluetooth and or Wi-Fi.

Employing Principles of Artificial Intelligence: Artificial Intelligence (AI) has Become Less Science fiction and more of a reality in recent years. It has integrated into everyday tasks, such as predicting the online buying preferences of a shopper, to its integration into complex systems and processes, such as driverless vehicles. An NES can employ concepts of AI for its operation. For example, limited memory AI or Type II AI, recalls events within a system's environment from previous experiences and integrates knowledge about the experiences to make real-time decisions in real-time situations. Future planning can also be done from these previous experiences and from real-time events. In the same way, an NES can integrate knowledge about past experiences to make decisions about current or future situations. The user, however, will reserve an ability to supersede the control of the AI, when and if needed. Previous knowledge can take the form of preoperative information about the patient being operated on. Previous knowledge can also include information about the particular surgeon wearing the NES. For example, data can be gathered from previous surgeries that indicate the surgeon has a tendency to fatigue at a certain time during a procedure or during the day. The NES computer can recall this information and make corrective adjustments to the appropriate regions of the NES to mitigate possible outcomes from this fatigue. It can also enhance fatigued regions of the user's body at the right time or provide additional support and guidance at the time that the data indicates the surgeon will likely fatigue.

NES Activation Through Signal Processing Within a Feedback Loop

An NES can operate in synergy with the user's motion. To achieve this synergistic cooperation, the NES can be in anywhere from occasional to constant communication with the NES computer. Sensors embedded within the NES can occasionally or continuously send information to the NES computer as they detect information about the surrounding environment. Positional sensors can send data to the computer about the position of regions of the NES in relation to the operating room and patient. For example, accelerometers can send data to the NES computer concerning the rate of movement of active regions of the NES. EMG sensors can send information back to the NES computer concerning muscle activity in different regions of the user's body. Once the NES computer receives data from the sensors, it can store the data and determine an appropriate response. For example, if EMG sensors embedded within the NES around the right arm of the surgeon detect muscle activity, or position sensors detect motion, the NES computer can determine the appropriate regions of the NES to activate the actuation of the actuating materials to assist with the user's desired motion. Signal transmission and signal processing response time is instantaneous so as not to delay the response time of the actuating materials, thus making the user and NES interaction with each other as seamless as possible.

Figure 64:
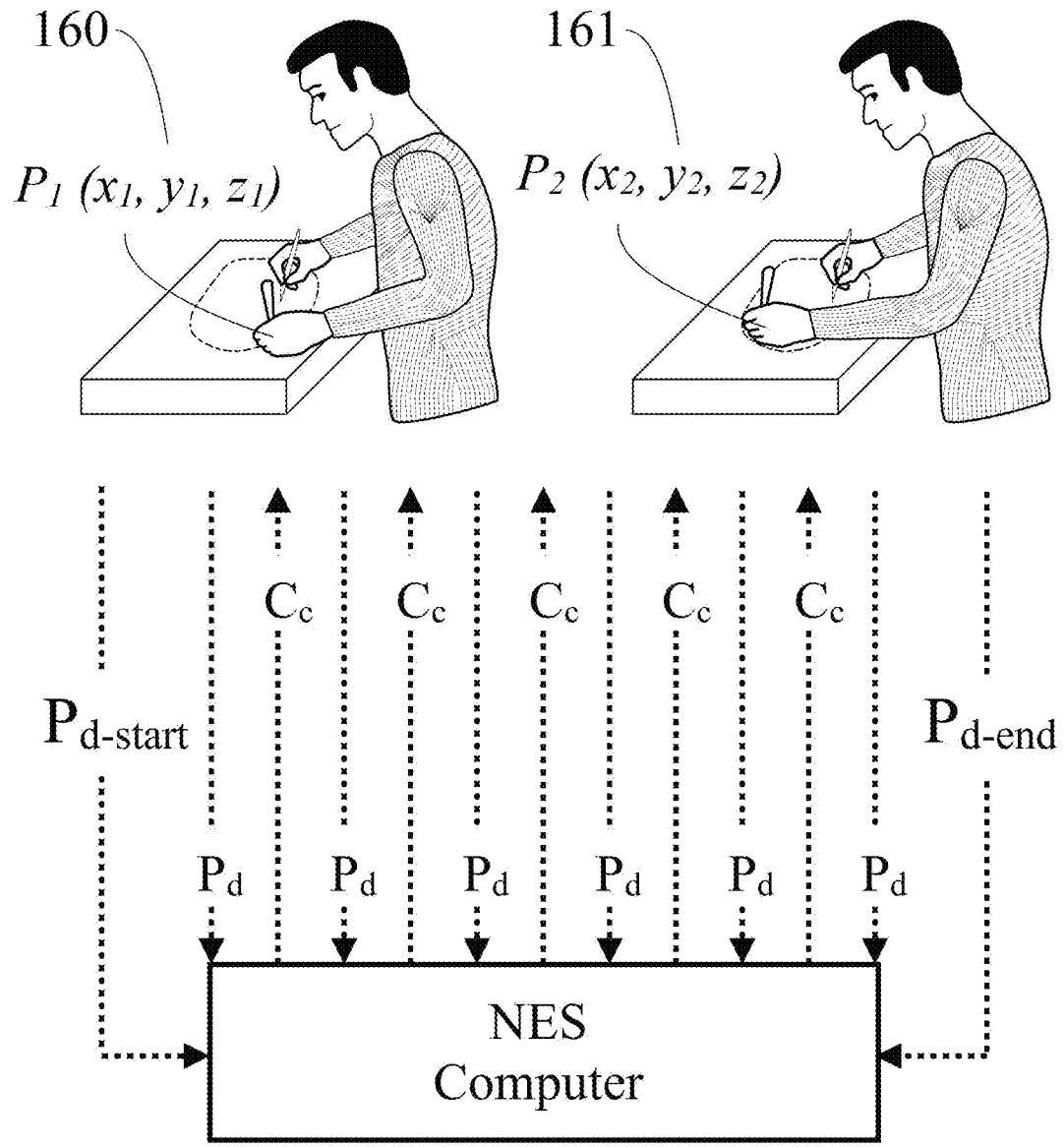
FIGS. 64-65 is a schematic illustration of the embodiment and its computer working in a feedback loop.

User Active/NES Support—UANS: The NES computer can monitor the motion of the user and store the position of different regions of the NES at different points in time. The back and forth data transmitted between the NES and the NES computer can be occasional or constant: The data that is sent and received in this back and forth exchange can be used to assist the surgeon with a desired task. For example, as shown in FIG. 64, a surgeon might begin a series of movements with his or her left arm at an initial position, P1, with spatial coordinates (x1, y1, z1) 160. He or she might then wish to move his or her left arm to a new position, P2, with spatial coordinates (x2, y2, z2) 161. Positional data represented by Pd are sent from the NES to the NES computer, while commands from the NES computer represented by Cc are sent back to the NES. Positional data (Pd-start) from P1 can be sent from the NES to the NES computer in a packet of information where it can then be stored on the NES computer. The surgeon can then initiate movement to a new position, P2. Throughout the path of motion that the arm takes moving from P1 to P2, the NES can send updates on the position of the left arm (Pd) to the NES computer while the NES computer can send back commands (Cc) to the NES to make adjustments in actuating material to assist with the motion of the left arm to reach P2. These updates can be occasional or constant. The final coordinates (Pd-end) can be sent back to the NES computer to be stored. These instantaneous iterations of occasional or constant communication between the NES and the NES computer can be carried out with any task where the user is in complete control of his or her motions but still receiving assistance from the NES with stability control and limb support. This type of user/system interaction will be referred to as the following: User Active/NES Support or UANS.

User Passive/NES Support—UPNS: In a different scenario, the user might command the NES computer to recall a stored coordinate and to assist in the guidance to return to that particularly stored coordinate. In this scenario, the NES and user, together, are functioning as a guided surgical system much like a surgical robot. The surgeon can simply relax his or her left arm while the NES moves the surgeon's left arm to the recalled position, P1. This type of user/system interaction will be referred to as the following: User Passive/NES Support or UPNS.

User Active Only—UAO: The surgeon can override the support from the NES at any time during this motion back to P1, if he or she wishes, and return to UANS mode or a mode that is completely without the assistance of the NES. Such a mode will be referred to as the following: User Active Only or UAO.

Figure 65:
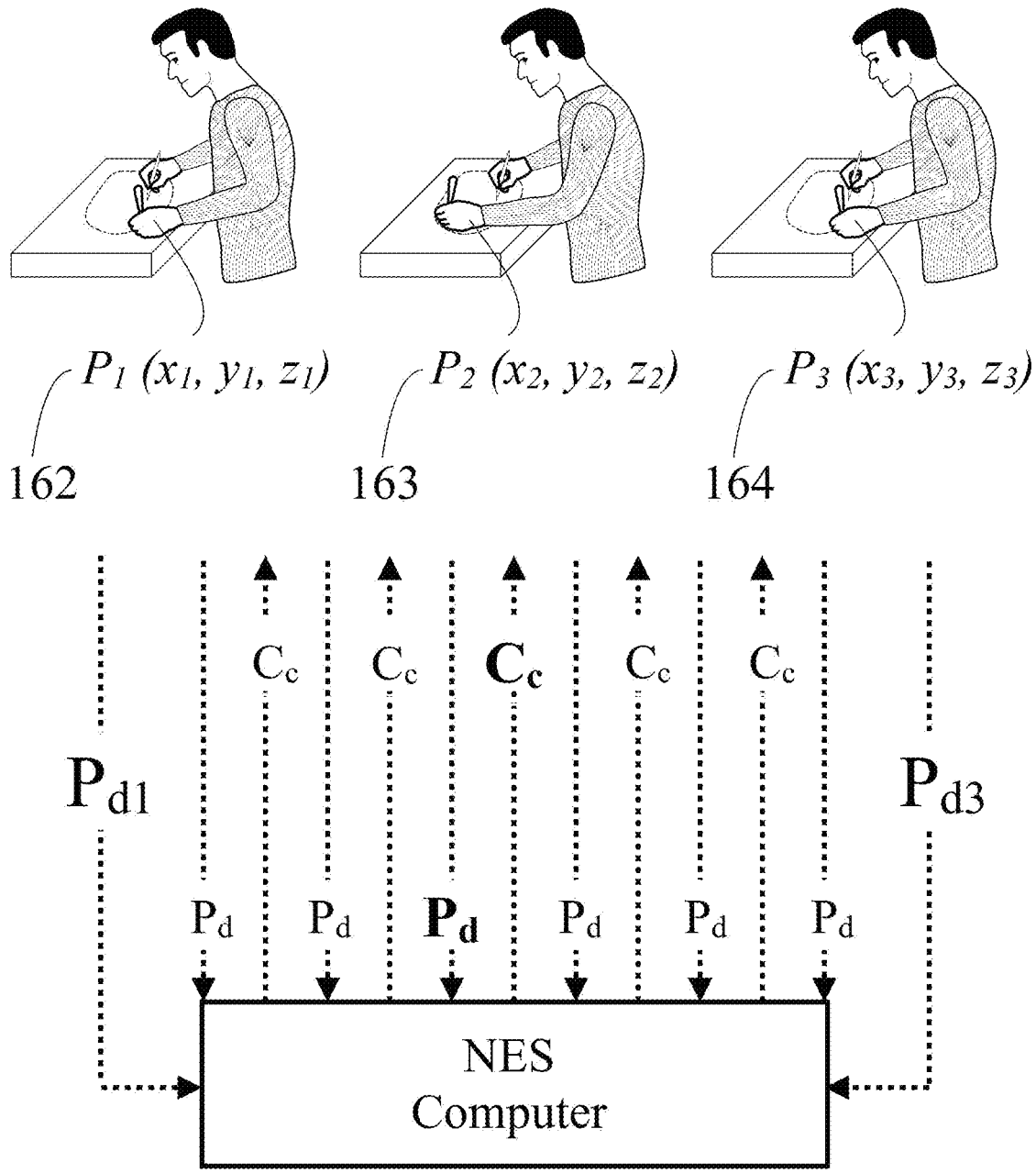

Combination of Modes: A UPNS scenario is depicted in FIG. 65 where the surgeon has moved his or her left arm from P1 162 to P2 163 in a UANS mode, but wishes to move back to P1 164 in a UPNS mode. Pd1 represents the first data packet of positional coordinates from position P1 sent from the NES to the NES computer. Pd2 represents the positional coordinates from position P2 sent from the NES to the NES computer achieved while in the UANS mode. Pd3 are the final positional coordinates achieved during this sequence of motion and is the same as Pd1, the positional coordinates recalled by the surgeon while in UANS mode. Pd represents data transmissions of positional coordinates from the NES to the NES computer, and Cc represents data transmissions of commands from the NES computer to the NES. These transmissions can be occasional or constant.

Commands and Signals

Commands transmitted to the NES for specific tasks to be carried out by the NES computer can be sent by the user through several means, for example, the user can speak commands that the NES will recognize. The NES computer can be configured to listen for spoken commands for specific tasks to be carried out. An embedded microphone can detect these commands and send them to the NES computer for processing.

A touch screen can attach to the NES or be embedded within the NES that allows the user to input commands to the NES computer. A flexible touch screen, for example, can reside on the non-dominant arm of the user, and with his or her dominant hand, he or she can enter commands on the flexible touch screen.

Commands can also be entered through visual cues made by the movement of the eyes of the NES user. These cues can be detected by goggles that monitor eye movement and visual cues and can output signals based on these movements and cues. They can serve as both a user input device and protective eye gear. The goggles can also have the capability to display images of the operating room, patient images, or other information to the user.

The user can use haptic and motion signals to enter commands into the system. For example, the user can tap his or her left arm at a specific location to begin motion of the left arm or to increase the snugness in the left arm. Two taps on a specific location of the left arm, for example, can indicate a need to decrease the temperature of the NES. These tap-sensitive locations can be located at various parts on the NES to interpret different numbers of taps or amount of pressure applied by the user. The various taps and amount of pressure can correspond to different commands. Motion commands can also be performed and understood by the NES. For example, a camera system can capture the user raising a hand or waving a hand that is recognized by the NES as a command.

Signals can be sent to the NES user a number of ways. One such way is through light indicators located throughout the operating room. For example, a flashing yellow light can indicate that the NES is moving at a speed that is approaching danger and a flashing red light can indicate that the system is moving at a dangerous speed which might cause harm to the patient. Other visual signals can be displayed for the user to see on a flexible touch screen monitor that the user can wear, or they can be displayed on a monitor located within the vicinity of the user.

Signals can also be sent to the user through a vibration initiated by the NES at various locations on the NES. For example, a vibration in the right calf area of the NES might indicate that the user should move his or her right leg because it has been sedentary for an extended period of time.

Audible signals can also be employed to indicate a message to the user. The audible signals can either be simple sounds or they can be pre-recorded or synthesized statements. For example, a speaker embedded within the NES, or a speaker located somewhere within the vicinity of the user, can tell the user through said speaker, in a spoken statement, that he or she is nearing a critical part of the surgery.

VII—Hybrid Embodiments

Figure 66:
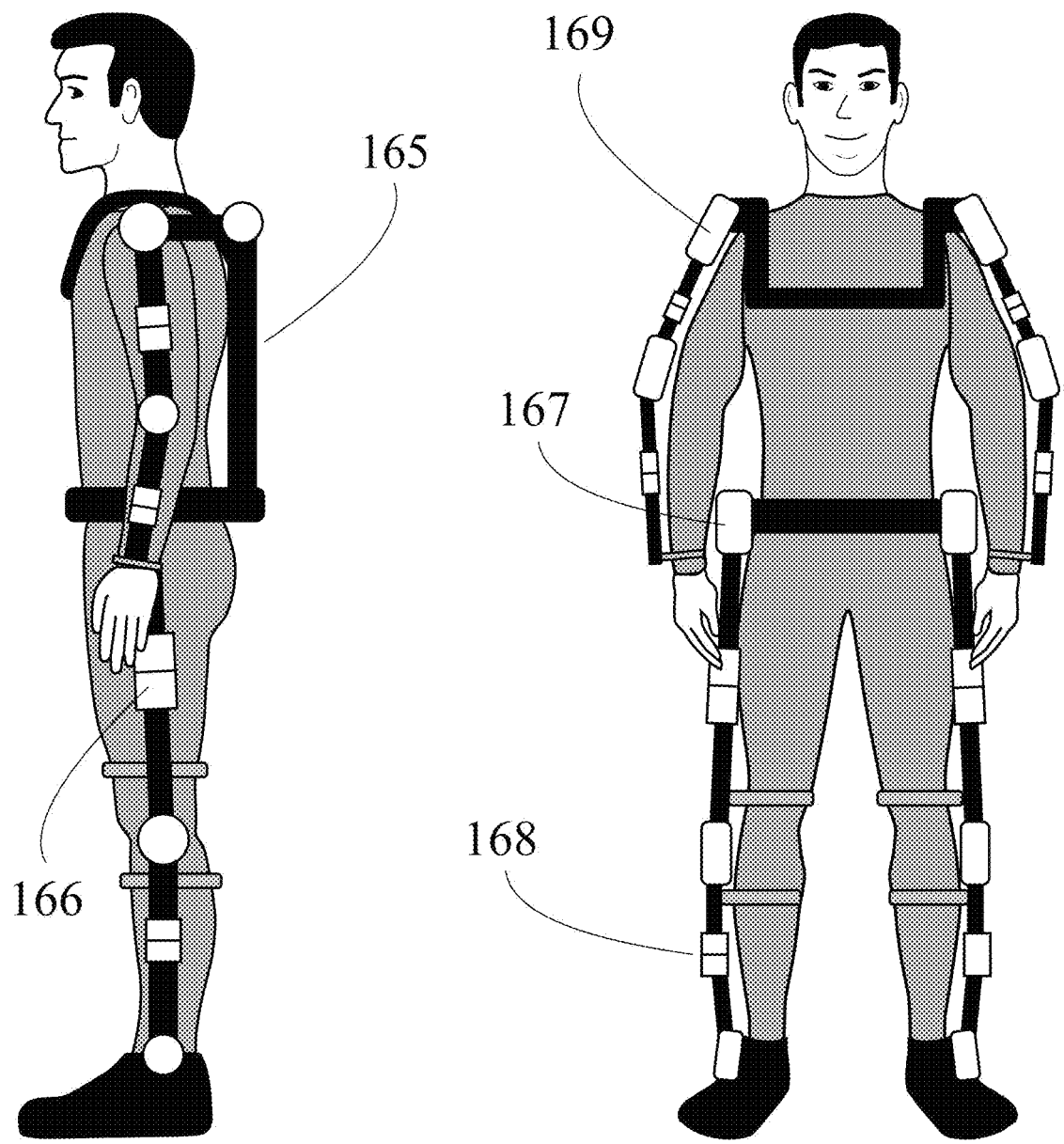
FIGS. 66-68 provide schematic illustrations of example hybrid technology embodiments.

Material components of an NES, as shown in FIG. 66, can comprise rigid support materials 165 composed, for example, out of polymers, metals, or alloys. They can comprise motion instruments such as linear actuators 166, motors 167, and pneumatic equipment 168 to provide forces required to move parts of the system and, therefore, the user. They can also comprise mechanical joints 169, such as the ones that are used in exoskeletal systems that link the rigid support materials and motion instruments to provide degrees of freedom. In these example embodiments, an NES appears and functions in a manner similar to that of current exoskeletal systems and can carry out the same motion-assist and enhancement features that were previously described here for surgery or for other applications.

Figure 67:
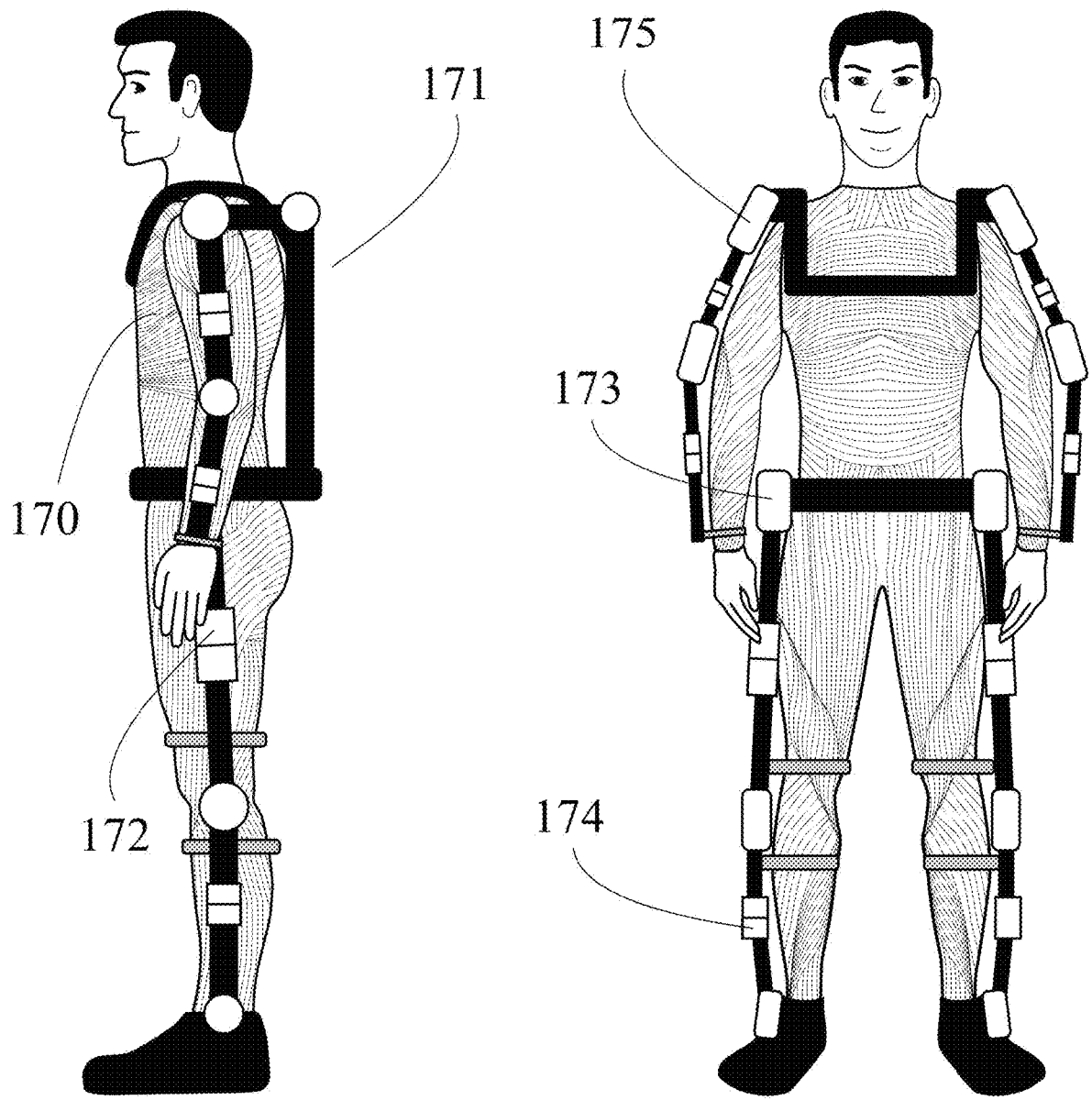

An NES can also be a hybrid system, as shown in FIG. 67, comprising actuating materials 170, as well as rigid support materials 171, linear actuators 172, motors 173, pneumatic equipment 174, and joints 175. These additional materials can be connected to the actuating materials and carry out the same motion-assist and enhancement features that were previously described for surgery or for other applications. This system is advantageous over current exoskeletal technology because of the reduction in the system's physical profile and weight due to the reliance on the actuating materials used in place of exoskeletal materials. Another advantage is that it can provide more force support due to the strength inherent in the rigid support materials.

Figure 68:
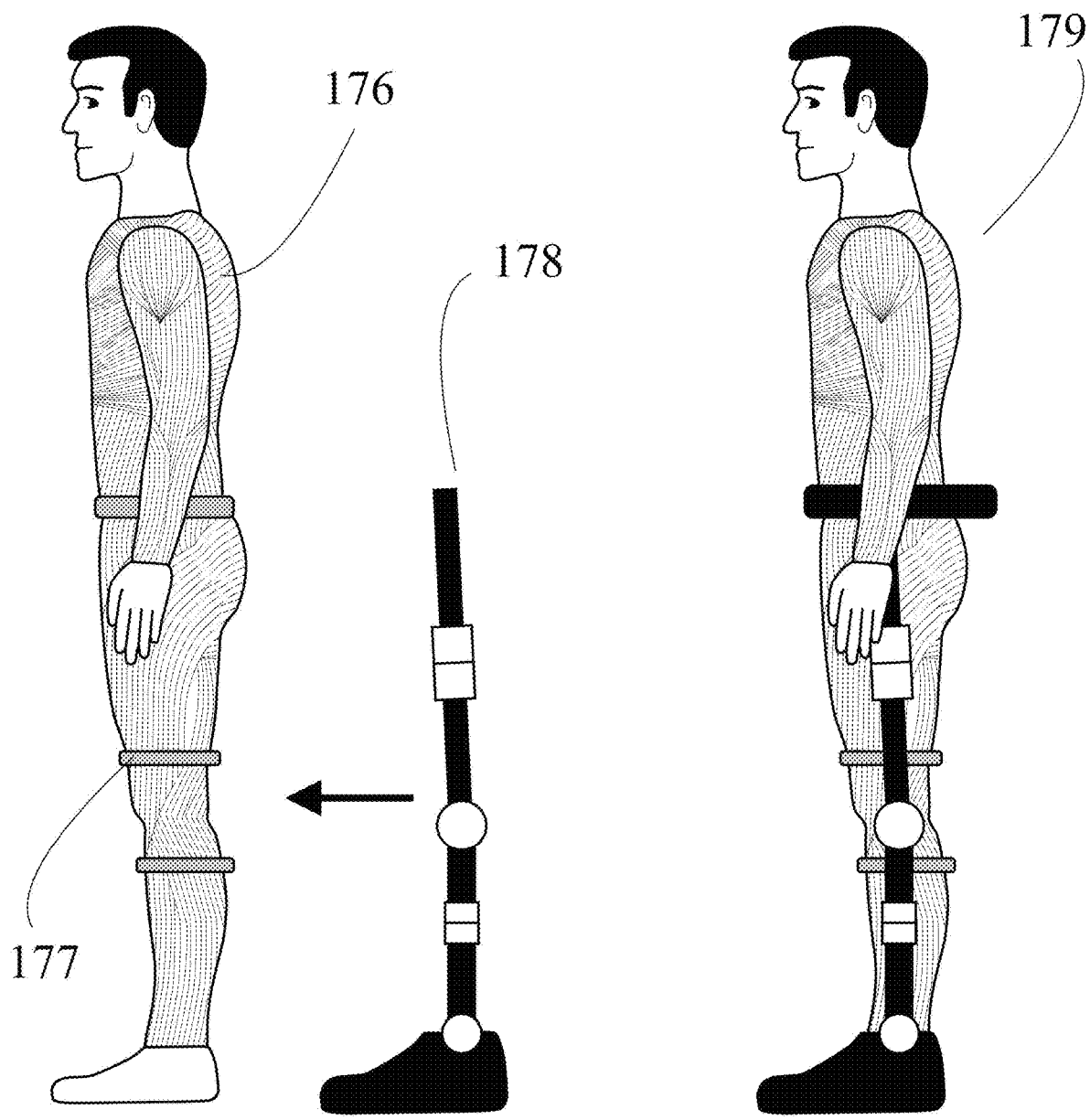

Another embodiment of the NES, depicted in FIG. 68, is a system with actuating materials 176 that have insertion points 177 located throughout the NES where exoskeletal materials can be connected to the NES to provide additional stabilization and strength enhancement. The exoskeletal materials can be disconnected when they are not needed. The use of these materials is optional and can be temporary, depending on the needs of the user. For example, if the user needs leg support and enhancement greater than what the actuating materials provide, the user can attach an exoskeletal leg structure 178 to the NES 179. These structures can contain actuators or other materials that can communicate seamlessly with the NES computer and work in conjunction with the actuating materials.

VIII—the NES Used in Surgery

An NES can have the capability of being interfaced with operating room equipment through physical connections such as wires and cables, or through radio waves such as Bluetooth and Wi-Fi. It can also be interfaced through a combination of wires, cables, and radio waves. The NES and the entire operating room become instantly linked the moment the NES user walks into the operating room, therefore, establishing a digital ecosystem that is under the surgeon's complete control. This matrix of interconnectivity can be used in any location where the NES is located. For example, a hospital, a triage center, or a patient's recovery room can all be equipped with technology that allows a user wearing an NES to instantly be connected to a network of equipment, computers, sensors, etc., when he or she walks into the equipped area.

Figure 69:
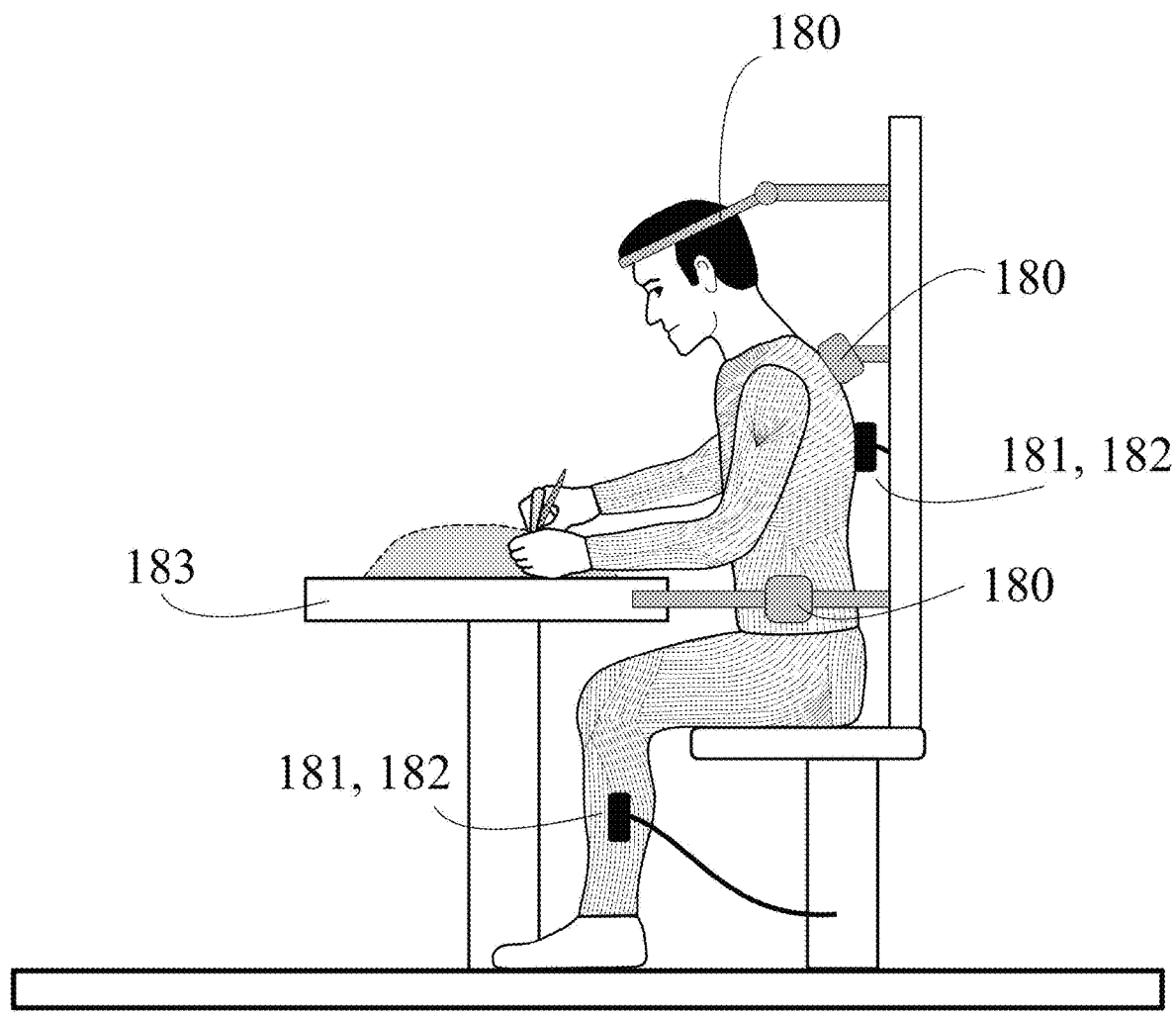
FIGS. 69-70 provide schematic illustrations of embodiments that include scaffolding systems for use in the operating room.

Scaffolding Support: A scaffolding system as shown in FIG. 69 can provide additional physical support, it can provide modes for communicating with the NES, and it can provide power to the NES. An NES, for example, can physically connect to an operating room table and surgical chair through its terminals. The connection with the scaffolding support can provide additional physical support 180, communication capabilities 181, and power 182 to the NES. These connections can slide along the scaffold according to the position of the surgeon and readjust according to the space available, allowing the surgeon to freely perform the surgery. The operating room table 183 can be embedded with sensors that provide feedback to the surgeon and information about the patient in real time through these connections 181, 182. The position of the table, chair portion of the scaffold, and back support of the scaffold can move according to the needs of the surgeon. For example, the height of the table and or chair can easily be adjusted.

Figure 70:
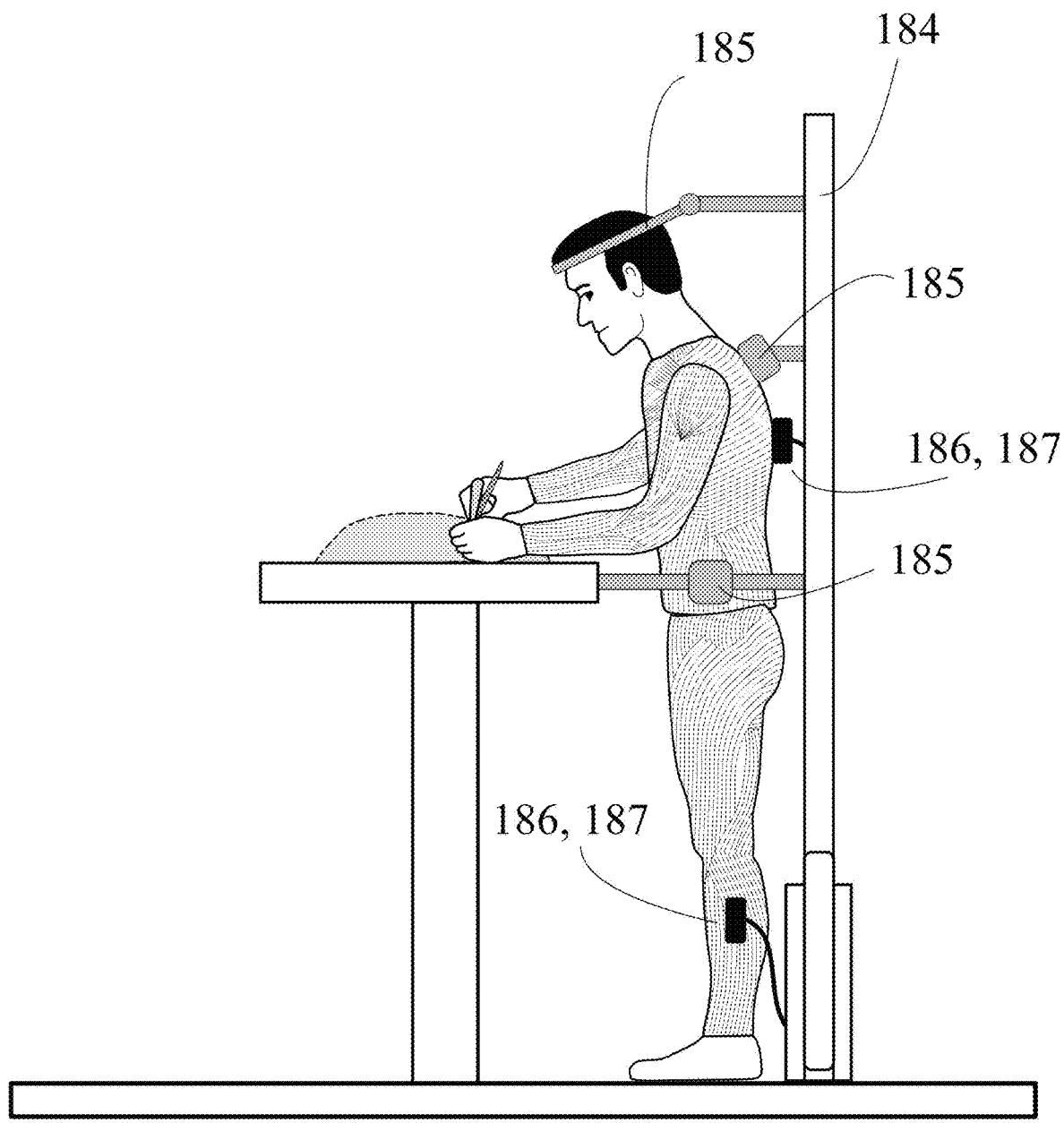

The chair can adapt to the needs of the surgeon, as shown in FIG. 70, so that the surgeon can stand during surgery, if he or she would like to stand. The chair can be folded away and the scaffold 184 converted to support a standing posture and still provide the same physical support 185, communication 186, and power 187 features to the NES that this embodiment provides when the surgeon is sitting.

Figure 71:
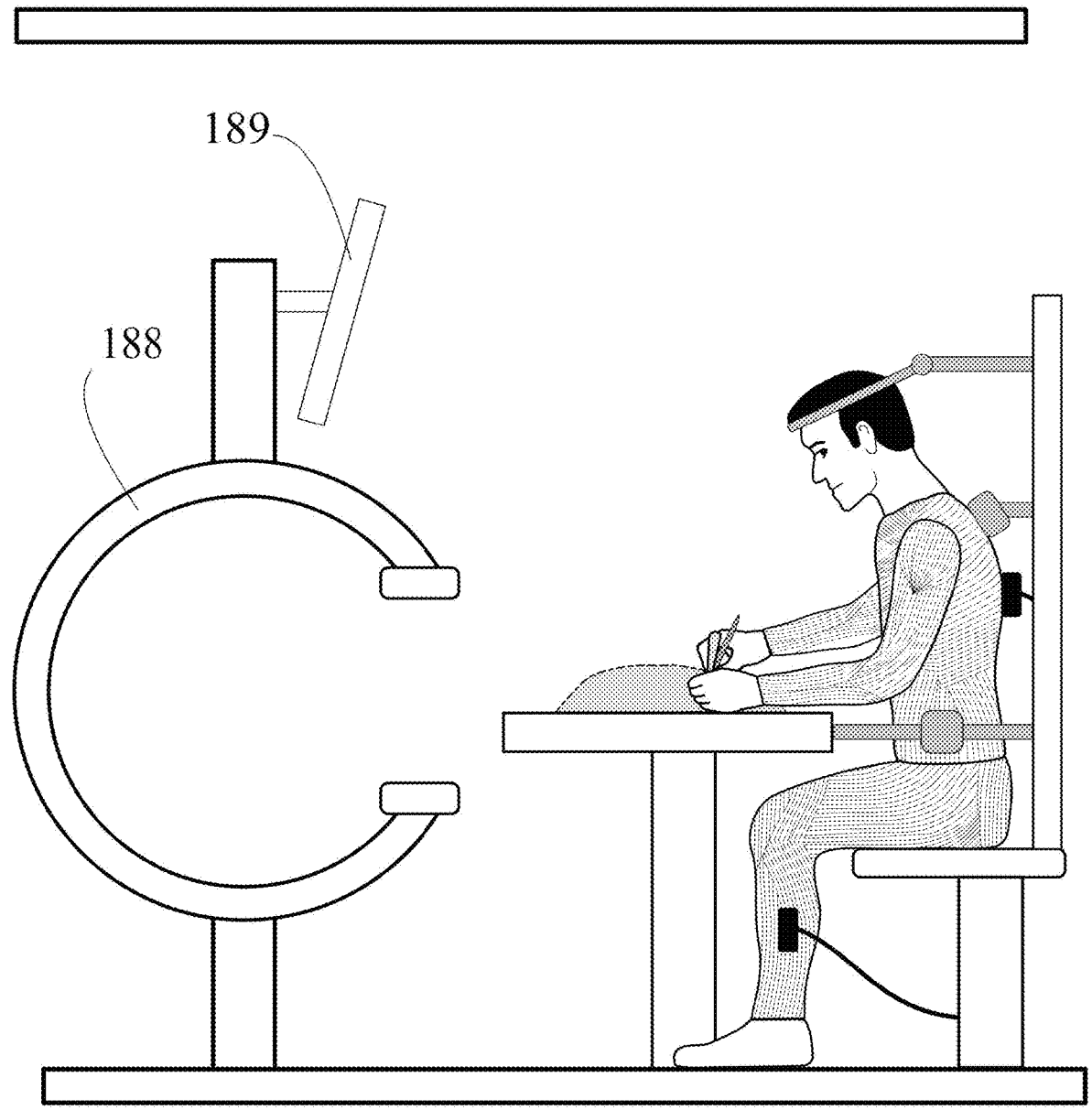
FIGS. 71-72 provide schematic illustrations of embodiments interfacing with the operating room.

Interfacing the NES with External Systems: An NES can act as an interface between the surgeon and the operating room in a more encompassing manner as shown in FIG. 71. The operating room and all the equipment within it, along with the NES, can become one combined system in which imaging equipment, surgical navigation systems, vision systems, microscopes, etc., function in unison with the surgeon and under complete or partial control of the surgeon. The surgeon, through voice commands or optical cues with the vision system, can command components of the operating room to function in a particular manner. For example, the surgeon can have direct control of the operation and position of a C-arm 188 during surgery due to the NES being interfaced with the equipment. As another example, the surgeon can control the position of the monitor and the monitor display 189. For example, a surgeon can command that a monitor displays a patient's vitals on a split screen along with recent images taken using the C-arm during surgery. Pre-operative images of the patient's anatomy can also be displayed as well as pre-surgical planning information. The screen can be a touch screen and as such can serve as a type of input device connected to the NES to send information or commands to the NES. The screen can be connected to a microscope or enhanced-vision goggles that the surgeon uses for vision enhancement, so that whatever is being viewed through the microscope or goggles is displayed on the screen. All of these functions can be controlled with the NES.

Figure 72:
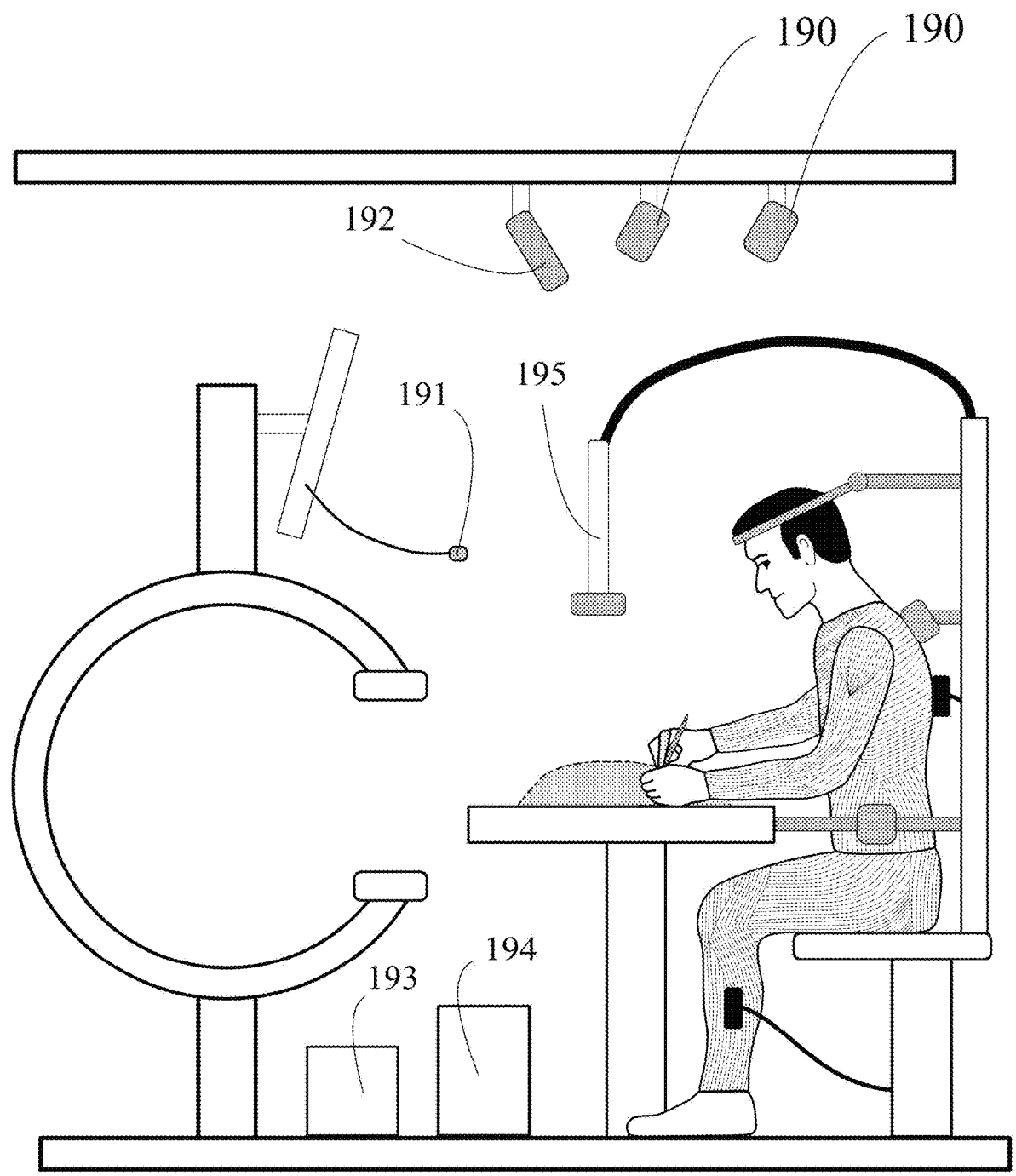

As shown in FIG. 72, a subsystem of the operating room can comprise of a lighting system 190 that the surgeon can control. The intensity and position of the light can be controlled by the NES/surgeon. This lighting subsystem can serve the purpose of illuminating the operative field, and it can also provide a beam of light that would serve as a guide for the surgeon by highlighting where an incision should be made or where to move an instrument. The beam of light can be controlled by the NES computer or the user.

Another example of subsystems are audio and microphone systems 191 that allow the surgeon to control equipment within the operating room. They can also be used for the control of features within the digital ecosystem, and for communication with people outside the operating room. Another example subsystem comprises a temperature-controlling system 192 that can direct a stream of cool or hot air onto the surgeon for his or her comfort during surgery. The position of each of these systems can be controlled by the NES computer system or by the surgeon. Additional computing 193 and power sources 194 can be added to the operating room system. These computing and power sources can be used for more complicated tasks that the NES computer and NES power system are not capable of handling, due to the additional operating room equipment.

A microscope 195 can be interfaced with the NES and operating room system. The position of the microscope can be positioned by the user with his or her hands or positioned remotely by voice command, a control console, visual cues, or by other means.

Figure 73:
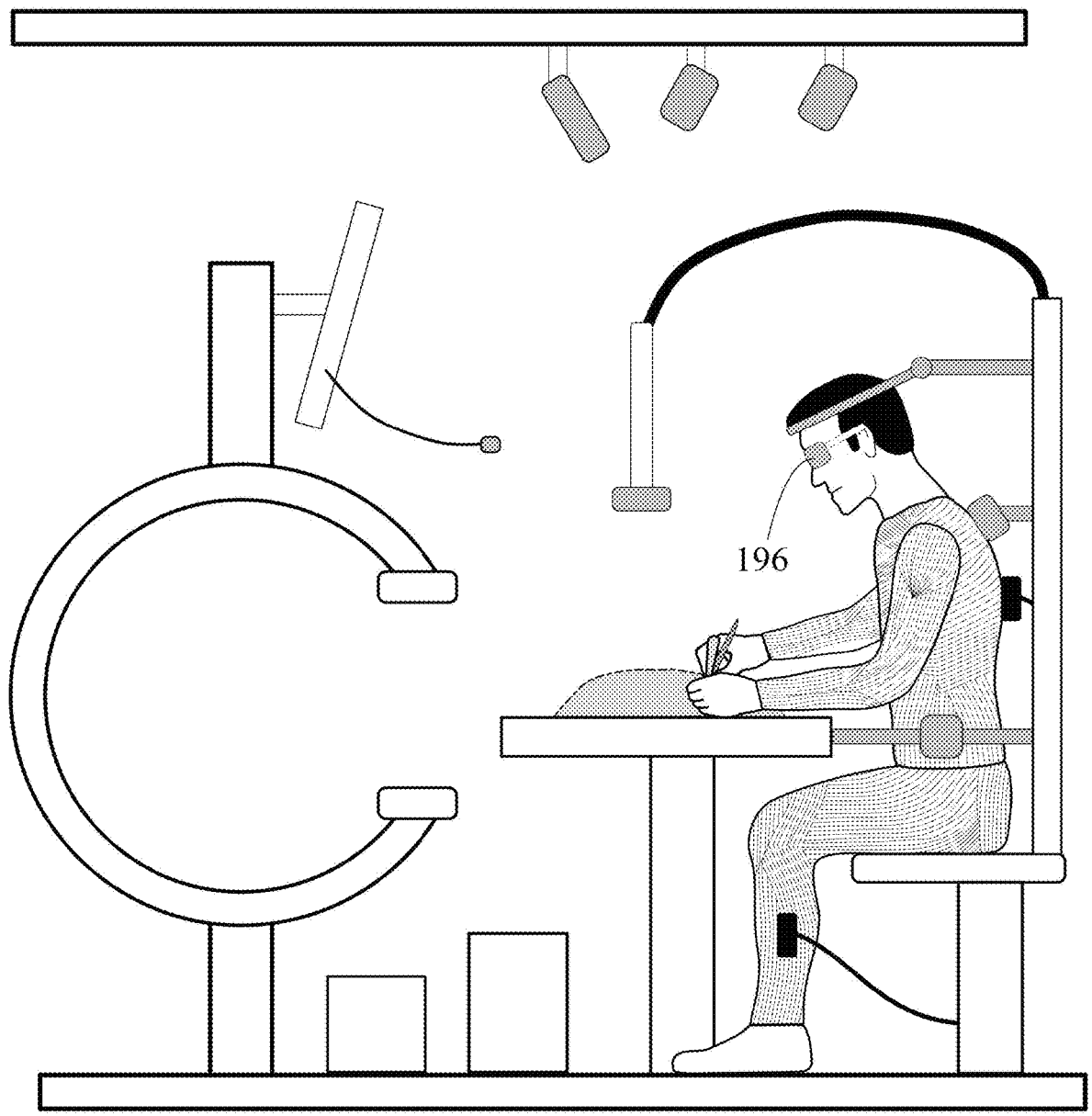
FIGS. 73-76 provide schematic illustrations of a vision system embodiment being used in the operating room.
Figure 74:
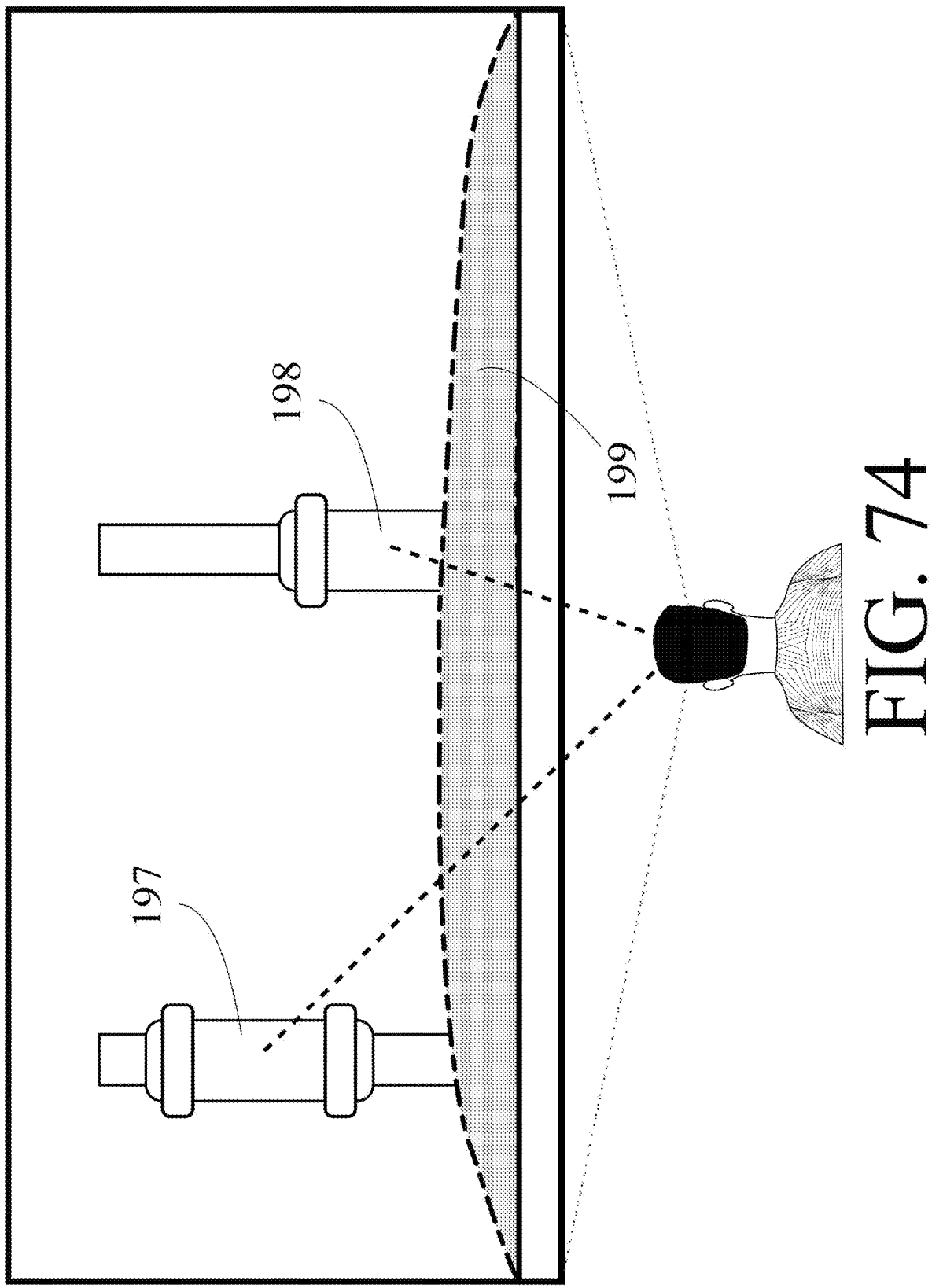
Figure 75:
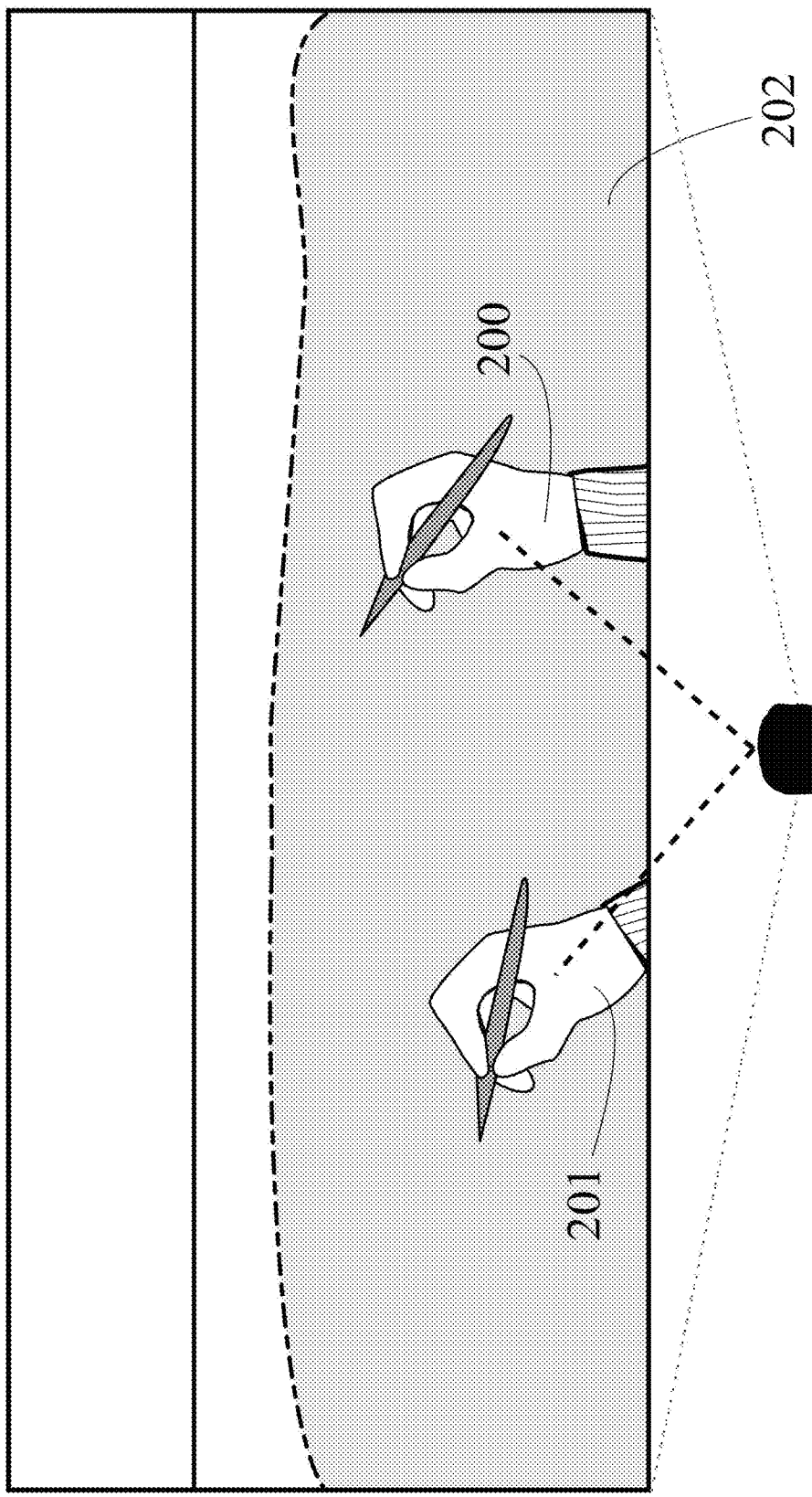

Enhanced Vision Goggle System: The user can view the output of the microscope, as shown in FIG. 73, through a monitor or an enhanced-vision goggle system 196. The vision goggles have the ability to allow for the user to send commands through the goggles, as shown in FIG. 74. The display that the user sees is a holographic projection onto the user's field of vision. The user can see the operative field and holographic projections of interactive items; the user can select and transmit commands through eye movements. For example, objects that are interfaced with the operating room system can be moved from an original position to a new position with visual cues that are detected by the enhanced-vision goggles. Through the movement of the user's eyes, the user can control certain equipment or features within the operating room such as the C-arm. The position of the C-arm 197 can be lowered and moved to the right 198, in relation to the patient 199, through visual cues initiated by the user and detected by the goggles. The position of the user's right arm, as shown in FIG. 75, can be moved from an original lateral position 200 to a new medial position 201, in relation to the patient 202, with these visual cues. These visual cues can be read by sensors or cameras inside the goggles or mounted on the outside of the goggles. The information can be interpreted by the NES computer and sent as a command to the NES to initiate a desired outcome.

Figure 76:
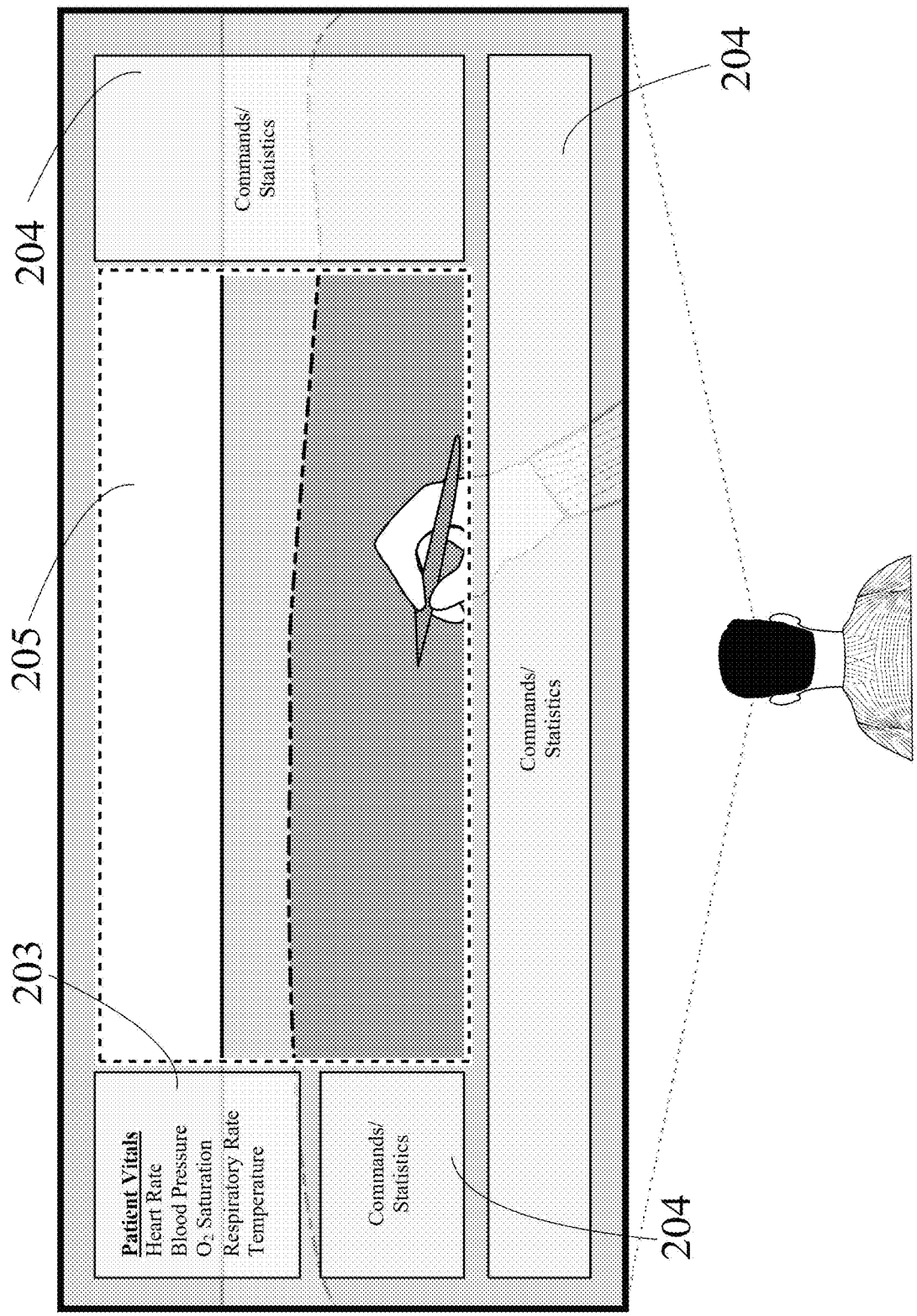

A goggle vision system, as shown in FIG. 76, can display on a digital screen embedded within the goggles or through a holographic projection, patient vitals 203, areas where the user can select commands and view statistics 204, and a view of the operative field 205.

Commands can also be sent to the NES through a computer console that resides near the NES computer. This console can comprise of a mouse, keyboard, joystick, touch screen, or any other type of input devices. The input device or devices can be connected directly to the NES either wirelessly or with a cable. It can also be connected to an external computer connected to the NES in the embodiment of the NES previously described where the NES computer resides separate from the NES. A monitor can also be connected in this arrangement to display the commands that the user is making, or other information that can be of use to the user or others.

Other visual signals can be displayed to the user on a flexible touch screen monitor that the user can wear. Visual signals can also be displayed on a monitor located within the vicinity of the user, or on vision enhanced goggles.

Connectivity Through Magnetic Resonance Imaging: In an embodiment of the NES, the NES connects directly to the patient's magnetic resonance images and the electromagnetic fields. With the information that is established through this connection, the NES can traverse the patient's anatomy and transfer forces to instrumentation through layers of soft tissue without resection of normal tissues. The system automatically recognizes nerves and critical tissue by monitoring the surgeon's vision of the magnetic resonance imaging, therefore, not invading critical aspects of organ tissue. The NES respects pathology in the same manner that it recognizes its abnormal border directly from the magnetic resonance properties.

Indicators to User: Indicator lights can be employed to notify the surgeon when he or she is in danger of approaching critical anatomy, such as a nerve or artery, or when he or she is moving at a velocity that has been predetermined to be dangerous. They can also serve to signal to the surgeon that he or she is nearing a critical level of fatigue. This critical level of fatigue threshold can be programmed within the NES computer and be based on clinical data about surgical fatigue. It can also be based on data that has been collected from previous surgeries by other surgeons who have used an NES or by the surgeon currently using the NES. Fatigue indicators located throughout the entire NES, certain areas of the NES, or on equipment connected to the NES, can signal to the surgeon his or her level of fatigue. For example, if the surgeon's vision is fatiguing, the enhanced-vision goggles can detect fatigue in the eyes through eye movement or the sagging of eyelids. The vision goggles can then send a signal to the NES computer and back to the surgeon through indicator lights that he or she is showing signs of fatiguing. Indicator lights can also be used to notify the surgeon that he or she should eat or hydrate to maintain maximum performance. This can be based on the surgeon's normal eating patterns or it can be calculated based on the amount of metabolic activity that has been exerted by the surgeon during the surgery. This metabolic activity can be detected by the biosensors and motion sensors embedded within the NES. The timing of these signals can be programmed so that they occur before the surgeon actually becomes hungry or thirsty, so that there is sufficient time for the surgeon to momentarily stop an activity and take a break, or to plan for the appropriate time to have a meal or rehydrate before he or she becomes too hungry or thirsty. Audio cues can be used instead of indicator lights or in conjunction with indicator lights for the same purposes.

Enhanced Headgear: As part of the NES, enhanced headgear can be worn to provide additional support and strength to the surgeon. The headgear can be connected to the NES, as any other stand-alone embodiment as previously described, such as an arm embodiment or torso embodiment. Within the headgear is an audio system and microphone that the surgeon can use to communicate with his or her environment. The headgear has enough space for the enhanced-vision goggles to be worn inside the enhanced headgear, or the user can use an enhanced-vision system that is a part of the enhanced headgear. For example, an enhanced-vision shield that drops over the eyes of the surgeon, similar to a motorcycle helmet and face shield, has the same vision enhancement features of the enhanced goggles. Embedded within this shield is technology that allows the surgeon all the vision system capabilities of the enhanced-vision goggles previously mentioned. Additional lighting is located on the outside and on the inside of the headgear to assist with illuminating the operative field or highlighting certain anatomical areas on the patient to assist with the surgery. This headgear also provides protection from debris that the surgeon might encounter during a surgery such as bodily fluids, bone fragments, and other biological substances.

Connectivity with Medical Equipment: The NES can connect to medical imaging equipment such as computed tomography (CT), magnetic resonance imaging (MRI), fluoroscopy, x-ray, etc. This connection can be made inside an imaging room, imaging center, OR, ER, or anywhere else the equipment may reside. The connection can also be made inside the operating room during, before, or after surgery. When the connection is made outside the operating room, the user of the NES can connect with the imaging equipment either wirelessly or through a cable while the images of the patient are being taken or after the images are taken. The transfer of the image data can be made through a series of commands initiated on the imaging equipment computer system or through an NES input device. Or the transfer of data can happen automatically through a wireless method when the user is within range of the imaging equipment's wireless signal.

Figure 77:
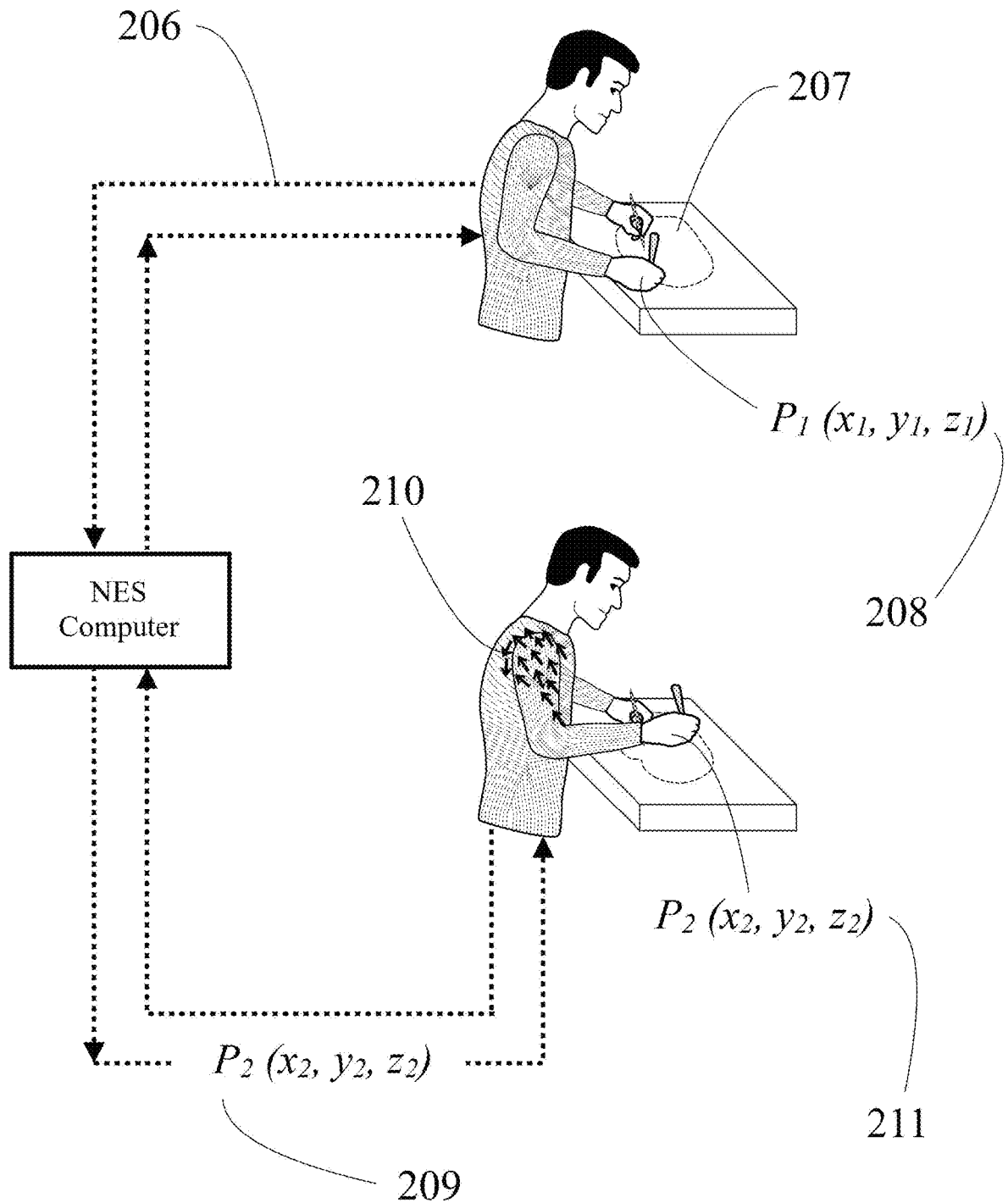
FIGS. 77-78 provide schematic illustrations of embodiments incorporating feedback loops using preoperative data and real time patient data with operating room equipment.

Imaging Systems and Surgical Navigation: A User Passive/NES Support (UPNS) scenario was previously described where the user relies on stored coordinate information of his or her left arm to return to a previously positioned point in space. The same UPNS mode can be activated for surgical guidance based on imaging of the patient's anatomy that was taken prior to surgery or that is taken during surgery. FIG. 57 depicted a feedback loop in which the NES, the NES user, and the NES computer system transmit and receive signals between each other. Within this feedback loop can reside imaging equipment, as depicted in FIG. 77, that can transmit and receive signals with the other systems. For example, during spine surgery the surgeon might be ready, at a certain point in the surgery, to place a pedicle screw into the right pedicle of the fourth lumbar vertebral body (L4) for spinal fixation. The surgeon will switch from UANS mode to UPNS mode and signal to the NES computer 206 that he or she wants to begin the insertion of the pedicle screw into the right pedicle of L4. A CT scan of the patient's lumbar anatomy, taken prior to surgery and stored in the NES computer, can be used to guide the current position of the surgeon's right arm to the appropriate position for the screw insertion. With this CT scan, the NES computer calculates the correct coordinates that the surgeon's right hand needs to be moved to for the precise placement of the screw. These coordinates can be based on the location of the L4 right pedicle as indicated by the preoperative images. The coordinates are correlated with the current anatomical position of the L4 right pedicle in relation to the operating room 207, and the present location of the surgeon's right arm 208. After recalling the image and calculating the new coordinate and NES materials that are needed to move the surgeon's right arm, the NES computer sends these signals to the NES 209. Through the actuation of the appropriate actuating materials 210, the surgeon's right arm is moved into the correct position for the placement of the screw 211.

Figure 78:
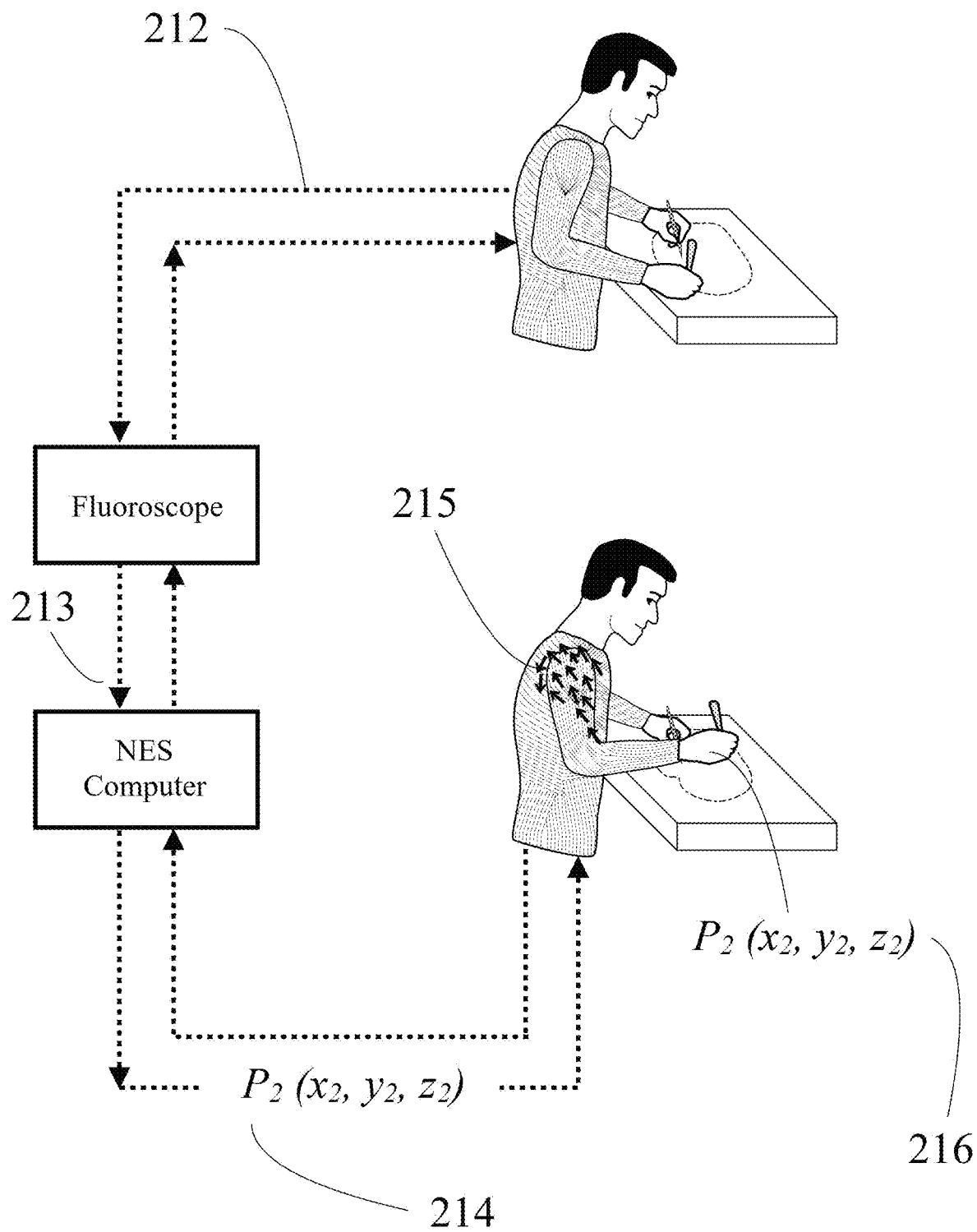

The imaging equipment can also reside within this feedback loop in a direct way as shown in FIG. 78 and provide real-time information to the surgeon. For example, if the surgeon prefers to rely on fluoroscopic images, instead of using CT scans, he or she can send a command to the fluoroscope 212 to take an image of the patient in the patient's current state. The image is then sent to the NES computer 213 for processing. The NES computer processes this current image and calculates the new coordinate to which the surgeon desires to move his or her hand for the insertion of the pedicle screw. This new coordinate and instruction for the NES is sent to the NES 214 to actuate the appropriate actuating materials 215 for the movement of the arm to the new position 216.

NES Glove and Instrument Connectivity: Another embodiment of the NES are gloves designed out of NES material which can be worn during surgery for enhancement of the hands. These gloves have the same features that the NES has and can be connected to the NES as an additional embodiment, as previously described. Haptic technology embedded in the gloves can help the surgeon carry out more delicate processes and carry out finer motor movements than the ones carried out in other areas of the body.

Surgical instruments specially designed to connect to the NES in a modular fashion can also be used by the surgeon. These instruments connect or disconnect from the NES gloves or other portions of the NES when needed by the surgeon. The instruments contain sensors that transmit signals from the operative field through the instrument and to the NES for the surgeon to interpret. For example, the instruments can detect when the surgeon is cutting through soft tissue and differentiate between the different types of tissue, such as a blood vessel, nerve tissue, fat, or muscle. They can also differentiate between healthy tissue and pathological tissue. The instruments also contain haptic technology to provide additional haptic feedback, in addition to the feedback the NES provides. These instruments can also provide additional guidance capabilities with any surgical navigation systems used during surgery.

Modules can be connected to instruments that are not specifically designed to integrate with the NES. For example, a module can snap together with a standard medical instrument and the module can then snap together with the NES gloves. As with the instruments designed to connect with the NES, the modules also provide additional surgical navigation capabilities with any surgical navigation guidance systems used during surgery.

Calibration and Syncing of the NES with External Systems: Calibration of the NES with respect to the patient can be performed by the surgeon by carrying out simple tasks such as touching certain landmarks on the patient or by touching landmarks in the operating room with his or her hand. These landmarks can be anatomical landmarks on the patient that register with the already saved imaging data of the patient, or the landmark can be operating room equipment or other registration points in the room. If additional areas of the NES require calibration, other tasks can be performed by the surgeon to calibrate these other areas. Position sensors embedded within the NES can communicate with one another to identify the relative location of other parts of the NES which can be used in place of a calibration routine. Calibration can also be carried out through the use of a camera system in the operating room that can identify the different areas of the NES and register these areas in relation to other equipment or the patient's anatomy. Calibration can require the user to consciously perform tasks to register the NES, or it can be done automatically. For example, the calibration can be done automatically as the user walks into the room with calibration technology that recognizes the NES and can register and track its location within a coordinate space.

IX—Other Applications for Neuromuscular Enhancement Systems and or Technologies

Embodiments of the present invention provide apparatuses that the user wears as an article of clothing and that wraps around the contours of the user's body. The user wears it to enhance his or her ability and longevity to perform desired tasks. The user moves seamlessly with the technology and is in control of all actions but receives assistance from the technology through a seamless control-loop feedback system. Embodiments of the present invention are streamlined, as compared to current physical enhancement systems. The base technology described above for surgery can be configured to provide the same strength-enhancing, support-enhancing, and accurate homing of the system's moving parts for other applications across various fields. The following are some examples where embodiments of the invention can be applied.

Healthcare: A geriatric patient can benefit from wearing an NES through the assistance it can provide during activities requiring the patient's legs, arms, or other parts of the body. The actions of sitting and or standing can be difficult due to musculature atrophy in elderly patients. The NES can assist with these actions or with rehabilitation therapy to rebuild the atrophied muscles through the regular use of the NES by the patient. Rehabilitation can occur through a programmed strength-enhancing regimen that the NES induces upon the user's command. The system can learn about the patient and where his or her weaknesses are and provide additional support to mitigate those weaknesses. An NES can also assist a patient by detecting when the patient may lose balance and initiate algorithms that move the patient in a particular way to prevent a fall or that help soften the fall.

A person suffering from arthritis who has little to no cartilage in a joint can wear an embodiment of the NES that assists with motion and stability. It can massage areas that are experiencing pain and deliver medicine to these painful areas. The NES can be programmed to optimize movement at the joint by providing additional support to the joint to reduce the amount of bone-on-bone contact in the joint.

A patient undergoing physical rehabilitation can wear an NES to help with strengthening exercises. The amount of assistance that the NES provides can be slowly decreased as the patient progresses in his or her therapy. The exercise regimen can be pre-programmed by the patient or healthcare provider. The NES can learn about the patient and determine deficiencies that the patient needs assistance with and develop an exercise regimen to strengthen the patient's muscles.

NES material technology can be used as an implantable graft for people needing a skin graft, a person who has received an amputation, or a person who has received any other type of procedure that can benefit from the features provided by the NES technology.

The NES technology can be used in place of an implantable device or as an organ transplant. In one embodiment it can make up the entirety of the materials for such devices or transplants, or it can be one of the many materials used in such devices or transplants. It can serve as both an enhancement material and serve to make the device or transplant a smart material through the capabilities previously described.

The NES can be used to immobilize a patient after an accident or trauma to reduce the risk of further injury while the patient is waiting for additional medical care or while the patient is being transported.

In one embodiment, the NES has coagulation properties that can be used to help someone who is suffering from a wound.

The NES can perform Heimlich maneuvers through the actuation of its materials and provide cardiac defibrillation if someone is in need of emergency care.

The NES can be worn long term by patients who suffer from neuromuscular disorders and need biomechanical assistance. For instance, a person who uses a wheelchair can use the NES to ambulate, therefore no longer requiring a wheelchair or other ambulatory assist devices. The NES can also be worn by someone who relies on the use of a mobility walker.

In one embodiment, the NES is configured to act as a prosthetic for the region or regions of the body the user needs. It can also be worn over an existing prosthetic as an overlay to provide additional force and remains on the body as a support structure. The NES can also be used to help connect the user to the prosthetic.

The massage and tissue activation technology of the NES used to comfort the surgeon during surgery can be employed for patients who are immobilized and are bedridden. It can be used to prevent bed sores or other related conditions due to inactivity and relieve pressure points.

The NES can be used to reduce or prevent the effects of venous disorders, blood clots, and edema. It can be worn to facilitate circulation in the same way that compression textiles, such as compression socks facilitate circulation. The NES can provide additional benefits that current compression textile technology does not provide.

Any healthcare provider that can benefit from motion and or ergonomic assistance can wear the NES. The healthcare provider wearing the NES can also provide care to a patient remotely by guiding another provider, or someone not medically trained, wearing another NES.

A person with little or no training in surgery can wear the NES to perform surgery while a trained surgeon controls the NES remotely.

A user that is undergoing medical training can wear the NES to receive training feedback and guidance from someone medically trained.

A healthcare provider or healthcare provider in training can wear an NES to assist in their education of anatomy, surgery, and or delivery of medical care.

In addition to the enhancement and guidance features that the NES offers, the NES can also improve the ergonomic conditions of a user. For example, the NES can assist a worker on an assembly line or someone who has to work at a desk for several hours at a time by ensuring the user maintains proper posture.

Automobile Safety: An NES can be worn to provide a driver or passenger physical constraint if an accident were to occur while in a vehicle. In this embodiment, the NES can connect to safety constraints in a car in lieu of a seatbelt. The NES can exist in its pliable state without any force application until the NES computer detects that the user is about to come into contact with another object at a dangerous speed. The actuating materials become rigid and encapsulate regions of the user's body preventing injury upon impact.

Manufacturing Industries: A user wearing the NES in a manufacturing setting can benefit from increased strength, increased longevity, improved ergonomics, and improved accuracy and speed in performing tasks.

Military Applications: Military personnel can also benefit from increased strength, increased longevity, and improved accuracy and speed by wearing an NES. Coordination with other military personnel can also be done using the communication system in the NES. The NES can be embedded with Kevlar or other types of body armor materials for further protection.

Search and Rescue: A user wearing the NES in a search and rescue setting can benefit from increased strength, increased longevity, and improved accuracy and speed in performing tasks. The temperature control of the NES can also benefit the user in extreme temperature conditions. Remote assistance provided by someone with training in medicine can be transmitted to the user of the NES. The NES can also be embedded with protective materials that would be useful in search and rescue situations.

Space Exploration: An embodiment of the NES has the capability of a spacesuit and protects against the elements in space. A user wearing the NES during space exploration benefits from increased strength, increased longevity, and improved accuracy and speed in performing tasks. Additional sensors are embedded on the NES to analyze minerals on other planets or damage to the exterior of a space craft. The NES can also assist with prolonged space missions to slow or prevent the atrophy of astronauts. The haptic feedback of the NES is an improvement over current space suit technology.

Athletic Training: The NES can help an athlete improve performance by providing resistance training. A training regimen can be programmed that increases or decreases resistance over time. It can detect deficiencies in strength and speed and assist the athlete to improve upon these deficiencies. The NES can also improve the performance and recovery of an athlete and can also be used to prevent chafing or rashes.

General Telerobotics: An expert in a technical field can guide the NES and the wearer of the NES through an interface that transmits the expert's motion to the user wirelessly so that the user can carry out a certain task or tasks.

Protective Services and Law Enforcement: A bomb expert can remotely guide a user of the NES if that expert is not available to be on the scene to diffuse a bomb. Sensors on the NES can assist in this work and provide an analysis of the scene and the bomb. The camera systems of the enhanced headgear or vision goggles can further enhance the user's ability to perform certain tasks and communicate with the security team and offer added protection. In this embodiment, the NES is embedded with materials that protect against a bomb blast. The NES is embedded with Kevlar or other types of body armor materials for further protection. A humanoid can also be clothed with the NES to help guide it in performing these tasks, thus eliminating the need for a human to be placed in a dangerous situation. The enhanced headgear previously mentioned can provide additional features and protection.

Fire Protection Services: A user from the fire department wearing the NES can benefit from increased strength, increased longevity, and improved accuracy and speed in performing tasks. The NES can resist and protect against extreme heat for fire situations. The enhanced headgear and or enhanced vision goggles can provide additional features and also provide protection from smoke inhalation.

Kinesthetic Learning: Teaching and learning can be enhanced in a variety of trades by having a teacher and student wearing an NES and interacting in a classroom setting or remotely with each other. For example, a teacher who must teach many dance classes throughout the day, can enhance his or her longevity by wearing an NES and will be able to teach more classes throughout the day and not fatigue as quickly. A difficult dance routine can be taught to the student by having both the teacher and the student wear an NES. The teacher can perform the routine while the student is attempting to perform the routine. The subtle forces provided by the NES to the student and directed by the teacher, who is also wearing the NES, can help the student learn the routine quicker. The system can also provide feedback to the teacher so the teacher knows where the student may need to improve on technique. This teacher-student dynamic can exist for someone learning a musical instrument or any other trade that requires the motion of the body.

General Consumer Product: An NES can be used for everyday use and not any specific industry. A user can keep an NES at home for a variety of uses. One such use is for computer assistance. A technology expert can remotely guide an NES user to make hardware repairs to his or her computer, troubleshoot software, troubleshoot a cell phone, or help with any other consumer electronics. A home user may want to wear an NES to complete certain tasks quicker and with less expenditure of energy. Tasks may include cooking, cleaning, lawn work, roof repairs, etc. The user may want to use the NES at the gym, swimming pool, while hiking, running, or playing a sport where they want enhancement or a programmed routine that will assist to improve their strength and or agility. A user may want to take an NES on a vacation where he or she knows he or she will be spending several hours standing in line at the airport or at an amusement park or doing a lot of walking. The NES can also be worn on a flight to prevent pilot fatigue and enhance passenger comfort.

EXAMPLE EMBODIMENTS

The NES is constructed out of materials that conform to the user's body. These materials are a combination of materials customized to actuate and apply forces in order to provide mechanical enhancement and or support. These materials contain sensors embedded within them that allow for the tracking of the position of any point on the NES. The NES is powered through a single source of energy or through a combination of energy sources. It functions with a computer that collects data about the NES and its environment, sends and receives commands to and from the NES and outside systems, and interfaces with other systems. The computer provides semi-autonomous and fully autonomous control of the NES.

Example Embodiment 1: A plurality of actuating substructure designs exist to cause the actuation of an embodiment. One embodiment of the system is that of a shape consisting of McKibben muscles attached to each other, and each supplied with a type of matter through a system of flexible tubes connected to each muscle. The matter is added to the muscles or removed from them using a pump system. An array of these muscles is attached to a flexible textile. The muscles can be attached to the fabric in a number of ways. For instance, as part of the manufacturing process of the fabric, the mesh structure of the McKibben muscle can be assembled into the fabric. The mesh can be 3-D printed onto the fabric, the mesh can be attached to the fabric by sewing, or the mesh can become a part of the fabric by some means not described here.

The inner tube of the McKibben muscle can consist of a variety of materials that expand when matter is introduced into it. Additionally, an embodiment consisting of an elastomer or another expanding material can be embedded within the mesh to cause the actuation of the muscle.

In place of the McKibben muscle structure can be any other material that exhibits actuation upon the introduction of matter or some other form of energy.

Each of the actuating muscles are independently controlled by a computer system. The muscles are connected to the computer system through a network of conducting materials, such as wire. Software on the computer communicates with the system to actuate each muscle depending on need. The computer and software also communicate with an array of sensors embedded within the fabric of the embodiment that collect data to be processed by the computer system.

Systems not embedded within the embodiment can also communicate with the computer of the embodiment and provide information to it or receive information from it. This communication can occur through a wireless means with the embodiment or through a means in which the systems are physically connected to the embodiment.

Example Embodiment 2: The embodiment consists of the actuating substructures aligned in a parallel fashion. As mentioned in Embodiment 1, the actuating substructures can be composed of any actuating type of materials.

Each of the actuating muscles are independently controlled by a computer system. The muscles are connected to the computer system through a network of conducting materials, such as wire. Software on the computer communicates with the system to actuate each muscle depending on need. The computer and software also communicate with an array of sensors embedded within the fabric of the embodiment that collect data to be processed by the computer system.

Systems not embedded within the embodiment can also communicate with the computer of the embodiment and provide information to it or receive information from it. This communication can occur through a wireless means with the embodiment or through a means in which the systems are physically connected to the embodiment.

Example Embodiment 3: The actuating materials are constructed out of actuating units that are activated through the application of electricity. Sheets of these fabrics are manufactured out of these types of fibers that lie parallel to each other along their length. These fabrics are sewn into a flexible fabric.

A network of electrical wires that are flexible and thin lie side by side the fibers to supply power to the fibers. They are connected to modular terminals that are located throughout the NES. These terminals are manufactured out of a material more rigid than the actuating materials and allow for a battery pack and modular PC to connect to it in order to supply electrical power and computing power. The wires are routed throughout the NES to supply power to position sensors that are used to detect the position of portions of the NES. These sensors are attached to the materials throughout the system so that each major section of the system can have its position tracked by the computer.

Example Embodiment 4: The actuating materials are constructed out of actuating units that are activated through the application of air. Sheets of these fabrics are manufactured out of these types of fibers encased in an expandable mesh as to form a McKibben type muscle. These muscles lie parallel to each other along their length. These fabrics are sewn into a wearable item of clothing that in this embodiment covers the user's upper body and lower body except for the head, hands, and feet. Upon activation, the actuating substructure expands and applies a tensile force to adjacent fabric or to the body of the user inducing a desired outcome.

A network of conducting materials, such as wires, lie side by side the actuating materials to supply power. They are connected to modular terminals that are located throughout the embodiment. These terminals are manufactured out of a material more rigid than the actuating materials and allow for a battery pack and modular PC to connect to it in order to supply electrical power and computing power. The wires are routed throughout the NES to supply power to position sensors that are used to detect the position of portions of the NES. These sensors are attached to the materials throughout the system so that each major section of the system can have its position tracked by the computer.

Example Embodiment 5: In this embodiment, the fabric is manufactured with a network of hollow channels allowing for matter to flow. The matter flows to different nodes, that when pressurized expand and produce a tensile force on adjacent material. The control of expansion and contraction of these nodes is controlled by a computer system on the embodiment.

The system, as is in the case of the previously described embodiment, is able to connect with equipment and systems not residing on the embodiment. The system is also embedded, in the fabric, with an array of sensors that facilitate the operation of the embodiment.

The present invention has been described as set forth herein in relation to various example embodiments and design considerations. It will be understood that the above description is merely illustrative of the applications of the principles of the present invention, the scope of which is to be determined by the claims viewed in light of the specification. Other variants and modifications of the invention will be apparent to those of skill in the art.

We claim:

1. An assistive system comprising:
   (a) an article configured to be worn by a user, comprising one or more sheets of actuating elements that change properties responsive to the supply of energy, which sheet or sheets are mounted with each other and shaped to substantially conform to at least a portion of the user's body;
   (b) a control system in communication with the article, and configured to supply energy to sheet or sheets such that the responsive change in the properties of the sheet or sheets augment, resist, or a combination thereof, motion or force of the user;
   (c) further comprising one or more sensors embedded in or mounted to the article, wherein the control system is responsive to the sensors; and
   (d) further comprising an imaging system configured to capture images of a workspace in which the user is moving, and
   wherein the control system is configured to encourage motion of the user to a predetermined location in the workspace; wherein the workspace comprises a surgical field, and
   wherein the imaging system is further configured to determine the predetermined location as a location in the surgical field correlated with images of a patient previously acquired.

2. The assistive system of claim 1, further comprising an exoskeletal system mounted with the article.

3. The assistive system of claim 1, wherein the control system is configured to supply energy to the one or more sheets such that the responsive change in the properties of the one or more sheets augments a first set of motions or forces of the user and resists a second set of motions or forces of the user.

4. The assistive system of claim 1, wherein the one or more sheets comprise a multilayer textile, comprising an actuating layer, a sensor layer, and a substrate layer.

5. The assistive system of claim 4, wherein the actuating layer comprises a plurality of strips of actuating material configured parallel to the long axis of a portion of the user's body, a plurality of strips perpendicular to the long axis of a portion of the user's body, or a plurality of strips configured in crossing pattern along the length of a portion of the user's body.

6. The assistive system of claim 1, wherein the one or more sheets comprise one or more McKibben muscles.

7. The assistive system of claim 1, wherein the one or more sheets comprise piezoelectric material, shape-memory polymer, magnetostrictive material, magnetic shape-memory alloy, smart inorganic polymer, temperature-responsive polymer, ferrofluid material, dielectric elastomer, magnetocaloric material, thermoelectric material, hydraulic response material, pneumatic response material, soft robotics material, or combinations thereof.

8. The assistive system of claim 1, further comprising a scaffold mounted with the article.

9. The assistive system of claim 1, further comprising an augmented reality display presented to the user that provides images of the real-world environment combined with previously captured images of the anatomy of a patient, with the images of the anatomy registered with the patient's real-world position.

10. The assistive system of claim 1, wherein the sheets comprise a material that provides shielding from radiation encountered in medical procedures.

11. The assistive system of claim 1, wherein the control system is configured to augment, resist, or both, motions, forces, or both, of a user performing surgery, wherein the article defines a plurality of pores that can selectively place the skin of the user in communication with ambient air.

12. The assistive system of claim 11, wherein the pores open and close responsive to the control system.

13. The assistive system of claim 1, further comprising an input device configured to mount with the body of the user, and wherein the control system is responsive to input from the user via the input device, wherein the input device is configured to mount near the eyes of the user, and wherein the input device accepts as inputs motion of one or both eyes of the user.

14. The assistive system of claim 1, further comprising one or more sensors embedded in or mounted to the article, wherein the control system is responsive to the sensors, wherein the one or more sheets comprise three or more McKibben muscles attached to each other, and comprising a pump in communication with the muscles and communicating matter to the muscles responsive to the control system.

15. The assistive system of claim 1, further comprising one or more sensors embedded in or mounted to the article, wherein the control system is responsive to the sensors, wherein the one or more sheets comprise a plurality of actuating fibers disposed parallel to each other and a plurality of flexible electrical wires disposed near fibers such that the electrical wires communicate electrical energy to the fibers responsive to the control system.

16. The assistive system of claim 1, further comprising one or more sensors embedded in or mounted to the article, wherein the control system is responsive to the sensors, wherein the one or more sheets comprise a plurality of hollow tubes disposed next to each other, and comprising a pump that communicates matter to the hollow tubes responsive to the control system.

17. The assistive system of claim 1, further comprising one or more sensors embedded in or mounted to the article, wherein the control system is responsive to the sensors, wherein the sensors are configured to supply a signal indicative of myoelectric signals, and wherein the one or more sheets comprise multilayer textile responsive to electrical energy, and further comprising one or more electrical energy storage device mounted with the article and in electrical communication with the one or more sheets responsive to the control system.

18. The assistive system of claim 17, further comprising an augmented reality display presented to the user that provides images of the real-world environment combined with previously captured images of the anatomy of a patient, with the images of the anatomy registered with the patient's real-world position.

19. The assistive system of claim 1, wherein the responsive change in the properties of the one or more sheets provides tensile forces to the user to augment, resist, or a combination thereof, motion or force of the user.

* * * * *